US006979724B2

(12) United States Patent
Lerman et al.

(10) Patent No.: US 6,979,724 B2
(45) Date of Patent: Dec. 27, 2005

(54) CALCIUM CHANNEL PROTEINS

(75) Inventors: Michael Isaac Lerman, Rockville, MD (US); Farida Latif, Birmingham (GB); Ming-Hui Wei, Germantown, MD (US); Fuh-Mei Duh, Ellicot City, MD (US); John Dorrance Minna, Dallas, TX (US); Yoshitaka Sekido, Aichi (JP); Boning Gao, Dallas, TX (US)

(73) Assignees: The United States of America as represented by the Secretary of the Department of Health and Human Services, Washington, DC (US); The Board of Regents of the University of Texas System, Austin, TX (US)

( * ) Notice: Subject to any disclaimer, the term of this patent is extended or adjusted under 35 U.S.C. 154(b) by 216 days.

(21) Appl. No.: 10/116,949

(22) Filed: Apr. 5, 2002

(65) Prior Publication Data

US 2003/0044911 A1 Mar. 6, 2003

Related U.S. Application Data

(62) Division of application No. 09/470,443, filed on Dec. 22, 1999, now Pat. No. 6,441,156.
(60) Provisional application No. 60/114,359, filed on Dec. 30, 1998.

(51) Int. Cl.[7] .................. C07K 14/435; C07H 21/04; A61K 38/17
(52) U.S. Cl. .................. 530/350; 536/23.5; 514/12; 424/185.1
(58) Field of Search ............ 530/350; 514/2, 514/12; 424/185.1, 192.1, 193.1; 536/23.1, 23.5

(56) References Cited

U.S. PATENT DOCUMENTS

| 4,650,764 A | 3/1987 | Temin et al. |
| 4,683,195 A | 7/1987 | Mullis et al. |
| 4,683,202 A | 7/1987 | Mullis |
| 4,797,368 A | 1/1989 | Carter et al. |
| 4,861,719 A | 8/1989 | Miller |
| 4,946,778 A | 8/1990 | Ladner et al. |
| 4,965,188 A | 10/1990 | Mullis et al. |
| 4,980,289 A | 12/1990 | Temin et al. |
| 5,124,263 A | 6/1992 | Temin et al. |
| 5,139,941 A | 8/1992 | Muzyczka et al. |
| 5,312,928 A | 5/1994 | Goldin et al. |
| 5,399,346 A | 3/1995 | Anderson et al. |
| 5,407,820 A | 4/1995 | Ellis et al. |
| 5,429,921 A | 7/1995 | Harpold et al. |
| 5,459,127 A | 10/1995 | Felgner et al. |
| 5,559,004 A | 9/1996 | Steinhardt et al. |
| 5,569,825 A | 10/1996 | Lonberg et al. |
| 5,580,859 A | 12/1996 | Felgner et al. |
| 5,589,466 A | 12/1996 | Felgner et al. |
| 5,618,720 A | 4/1997 | Ellis et al. |
| 5,625,126 A | 4/1997 | Lonberg et al. |
| 5,686,241 A | 11/1997 | Ellis et al. |
| 5,710,250 A | 1/1998 | Ellis et al. |
| 5,792,846 A | 8/1998 | Harpold et al. |
| 5,843,742 A | 12/1998 | Natsoulis et al. |

FOREIGN PATENT DOCUMENTS

| EP | 453243 | | 10/1991 |
| EP | 178220 | | 1/1992 |
| EP | 185573 | | 5/1992 |
| EP | 488528 | | 11/1995 |
| WO | 89/07150 | | 8/1989 |
| WO | 90/02806 | | 3/1990 |
| WO | 90/13678 | | 11/1990 |
| WO | 91/18088 | | 11/1991 |
| WO | 92/05263 | * | 4/1992 |
| WO | 93/09239 | * | 5/1993 |
| WO | 94/12649 | * | 6/1994 |
| WO | 94/21807 | * | 9/1994 |
| WO | 94/26914 | * | 11/1994 |
| WO | 94/28152 | * | 12/1994 |
| WO | 94/28938 | * | 12/1994 |
| WO | 95/02697 | * | 1/1995 |
| WO | 95/18863 | * | 7/1995 |
| WO | 95/21931 | * | 8/1995 |
| WO | 95/07358 | * | 3/1996 |
| WO | 96/15244 | * | 5/1996 |
| WO | 96/17823 | * | 6/1996 |
| WO | 96/22378 | * | 7/1996 |
| WO | 96/25508 | * | 8/1996 |

OTHER PUBLICATIONS

Barclay et al. Ducky mouse phenotype of epilepsy and ataxia is associated with mutations in the Cacna2d2 gene and decreased calcium channel current in cerebellar purkinje cells. J Neurosci 21(16):6095–6104, 2001.*

Carboni et al. CACNA2D2–mediated apoptosis in NSCLC cells is associated with alterations of the intracellular calcium singaling and distruption of mitochondria membrane integrity. Oncogene 22:615–626, 2003.*

Felix, R. Channelopathies: ion channel defects linked to heritable clinical disorders. J Med Genet 37:729–740, 2000.*

Gao et al. Functional properties of a new voltage–dependent calcium channel alpha(2)delta auxiliary subunit gene (CACNA2D2). J Biol Chem 276(16):12237–12242, 2000.*

Wells. J.A. Additivity of mutational effects in proteins. Biochemistry 29(37): 8509–8517, 1990.*

Ngo et al. Computational complexity, protein structure prediction, and the Levinthal paradox. The Protein Folding Problem and Tertiary Structure Prediction, pp. 492–495, 1994.*

(Continued)

*Primary Examiner*—Elizabeth Kemmerer
*Assistant Examiner*—Bridget E. Bunner
(74) *Attorney, Agent, or Firm*—Klarquist Sparkman, LLP

(57) ABSTRACT

The present invention relates to calcium channel compositions and methods of making and using same. In particular, the invention relates to calcium channel alpha2delta ($\alpha_2\delta$) subunits and nucleic acid sequences encoding them. These compositions are useful in methods for identifying compounds that modulate the activity of calcium channels and for identifying compounds as therapeutic for disease.

6 Claims, 4 Drawing Sheets

OTHER PUBLICATIONS

Hering et al. Molecular determinants of inactivation in voltage–gated Ca2+ channels. J Physiol 528(2): 237–240, 2000.*

Genbank Accession No. AF040709, direct submission, Nov. 5, 1998.*

Genbank Accession No. AAC70914, direct submission, Nov. 4, 1998.*

McFadzean et al. The developing relationship between receptor–operated and store–operated calcium channels in smooth muscle. Brit J pharmcol 135: 1–13, 2002.*

Genbank Accession No. AAB96913, Wei et al., direct submission, Jan. 17, 1998.*

Genbank Accession No. AF042792, Wei et al., direct submission, Jan. 17, 1998.*

Skolnick et al. From genes to protein structure and function: novel applications of computational approaches in the genomic era. Trends in Biotech 18(1): 34–39, 2000.*

Bork, A. Powers and pitfalls in sequence analysis: the 70% hurdle. Genome Res 10: 398–400, 2000.*

Doerks et al. Protein annotation: detective work for function prediction. Trends in Genetics 14(6): 248–250, 1998.*

Smith et al. The challenges of genome sequence annotation or "The devil is in the details". Nature Biotech 15: 1222–1223, 1997.*

Brenner, S.E. Errors in genome function. Trends in Genetics 15(4): 132–133, 1999.*

Bork et al. Go hunting in sequence databases but watch out for the traps. Trends in Genetics. 12(10): 425–427, 1996.*

Research Disclosure 37105, "Recombinant Herpesvirus Lacking Gene for Glycoprotein L," 1995, p. 124–130.*

Alton et al., "Non–Invasive Liposome–Mediated Gene Delivery Can Correct the Ion Transport Defect in Cystic Fibrosis Mutant Mice," *Nature Genet.* 5:135–142, 1993.

Angelotti and Hofmann, "Tissue–Specific Expression of Splice Variants of the Mouse Voltage–Gated Calcium Channel $\alpha_2/\delta$ Subunit," *FEBS* 397:331–337, 1996.

Ausubel et al., *Current Protocols in Molecular Biology,* John Wiley & Sons, New York NY, 1989.

Bangalore et al., "Influence of L–Type Ca Channel $\alpha_2/\delta$–Subunit on Ionic and Gating Current in Transiently Transfected HEK 293 Cells," *Am. J. Physiol.* 270 (5 Pt. 2):H1521–1528, 1996.

Barclay et al., "Mouse Models of Spike–Wave Epilepsy," *Epilepsia* 40 (Supp.) 3:17–22, 1999.

Bateman et al., "Pfam 3.1: 1313 Multiple Alignments and Profile HMMs Match the Majority of Proteins," *Nucleic Acids Research* 27(1):260–262, 1999.

Baylin et al., "Alterations in DNA Methylation: A Fundamental Aspect of Neoplasia," *Adv. Cancer Res.* 72:141–196, 1998.

Becker et al., *In Protein Expression in Animal Cells,* Roth et al. (eds.), 1994.

Bender et al., "Evidence that the Packaging Signal of Moloney Murine Leukemia Virus Extends into the gag Region," *J. Virol.* 61:1639–1646, 1987.

Bernstein et al., "Gene Transfer with Retrovirus Vectors," *Genet. Eng.* 7:235–261, 1985.

Berridge et al., "Calcium—a Life and Death Signal," *Nature* 395:645–648, 1998.

Biel et al., "Primary Structure and Functional Expression of a High Voltage Activated Calcium Channel from Rabbit Lung," *FEBS* 269:409–412, 1990.

Black et al., "Identification and Cloning of Putative Human Neuronal Voltage–Gated Calcium Channel $\alpha$–2 and $\alpha$–3 Subunits: Neurologic Implications," *Mayo Clin. Proc.* 74(4):357–361, 1999.

Bork et al., "More von Willebrand Factor Type A Domains? Sequence Similarities with Malaria Thrombospondin–Related Anonymous Protein, Dihydropyridine–Sensitive Calcium Channel and Inter–$\alpha$ Trypsin Inhibitor," *Biochem. J.* 279:908–10, 1991.

Bowie et al., "Deciphering the Message in Protein Sequences: Tolerance to Amino Acid Substitutions," *Science* 247:1306–1310, 1990.

Brown and Gee, "Cloning and Deletion Mutagenesis of the $\alpha_2/\delta$ Calcium Channel Subunit from Porcine Cerebral Cortex. Expression of a Soluble Form of the Protein that Retains [$^3$H] Gabapentin Binding Activity," *J. Biol. Chem.* 273:25458–25465, 1998.

Brust et al., "Human Neuronal Voltage–Dependent Calcium Channels: Studies on Subunit Structure and Role in Channel Assembly," *Neuropharmacol.* 32:1089–1102, 1993.

Burgess et al., "Mutation of the $Ca^{2+}$ Channel $\beta$ Subunit Gene Cchb4 is Associated with Ataxia and Seizures in the Lethargic (1h) Mouse," *Cell* 88:385–392, 1997.

Burgess et al., "Possible Dissociation of the Heparin–Binding and Mitogenic Activities of Heparin–Binding (Acidic Fibroblast) Growth Factor–1 From Its Receptor–Binding Activities by Site–Directed Mutagenesis of a Single Lysine Residue," *The Journal of Cell Biology* 111:2129–2138, 1990.

Caplen et al., "Gene Therapy for Cystic Fibrosis in Humans by Liposome–Mediated DNA Transfer: The Production of Resources and the Regulatory Process," *Gene Ther.* 1:139–147, 1994.

Castellano and Perez–Reyes, "Molecular Diversity of $Ca^{2+}$ Channel $\beta$ Subunits," *Biochem. Soc. Trans.* 22:483–488, 1994.

Chiorini et al., "Cloning of Adeno–Associated Virus Type 4 (AAV4) and Generation of Recombinant AAV4 Particles," *J. Virol.* 71:6823–6833, 1997.

Chiorini et al., "Cloning and Characterization of Adeno–Associated Virus Type 5," *J. Virol.* 73:1309–1319, 1999.

Cole et al., "The EBV–Hybridoma Technique and its Application to Human Lung Cancer," in *Monoclonal Antibodies and Cancer Therapy,* Reisfeld et al. (eds.), pp. 77–96, Alan R. Liss, Inc., 1985.

Coombs, *Dictionary of Biotechnology,* Stockton Press, New York NY, 1994.

Cote et al., "Generation of Human Monoclonal Antibodies Reactive with Cellular Antigens," *Proc. Natl. Acad. Sci. USA* 80:2026–2030, 1983.

Curiel et al., "High–Efficiency Gene Transfer Mediated by Adenovirus Coupled to DNA–Polylysine Complexes," *Hum. Gene Ther.* 3:147–154, 1992.

Davidson et al., "A Model System for In Vivo Gene Transfer into the Central Nervous System Using an Adenoviral Vector," *Nature Genet.* 3:219–223, 1993.

De Jongh et al., "Subunits of Purified Calcium Channels $\alpha$2 and $\delta$ are Encoded by the Same Gene," *J. Biol. Chem.* 265:14738–14741, 1990.

De Koninck and Schulman, "Sensitivity of CaM Kinase II to the Frequency of $Ca^{2+}$ Oscillations," *Science* 279:227–230, 1998.

Dolphin et al., "The Effect of a α2–δ and Other Accessory Subunits on Expression and Properties of the Calcium Channel α1G," *J. Physiol.* 519.1:35–45, 1999.

Doyle and Stubbs, "Ataxia, Arrhythmia and Ion–Channel Gene Defects," *TIG* 14(3):92–97, 1998.

Ellis et al., "Sequence and Expression of mRNAs Encoding the $\alpha_1$ and $\alpha_2$ Subunits of a DHP–Sensitive Calcium Channel," *Science* 241:1661–1664, 1988.

Engelhardt et al., "Ablation of E2A, in Recombinant Adenoviruses Improves Transgene Persistence and Decreases Inflammatory in Mouse Liver," *Proc. Natl. Acad. Sci. USA* 91:6196–6200, 1994.

Estacion and Mordan, "PDGF–Stimulated Calcium Influx Changes During In Vitro Cell Transformation," *Cell Signal* 9:363–365, 1997.

Felgner and Ringold, "Cationic Liposome–Mediated Transfection," *Nature* 337:387–388, 1989.

Felgner et al., "Lipofection: A Highly Efficient, Lipid–Mediated DNA–Transfection Procedure," *Proc. Natl. Acad. Sci. USA* 84:7413–7417, 1987.

Felgner, "Particulate Systems and Polymers for In Vitro and In Vivo Delivery of Polynucleotides," *Adv. Drug Del. Rev.* 5:163–187, 1990.

Felgner, "Prospects for Synthetic Self–Assembling Systems in Gene Delivery," *J. Gene Med.* 1:290–292, 1999.

Graham, "Covalently Closed Circles of Human Adenovirus DNA are Infections," *EMBO J.* 3:2917–2922, 1984.

Graham et al., "Characteristics of a Human Cell Line Transformed by DNA from Human Adenovirus Type 5," *J. Gen. Virol.* 36:59–74, 1977.

Graham and Prevec, "Adenovirus–Based Expression Vectors and Recombinant Vaccines," pp. 363–390, in *Biotechnology*, vol. 20, 1992.

Graham and Prevec, "Manipulation of Adenovirus Vectors," *Meth. Molec. Biol.* 7:109–128, 1991.

Gurnett et al., "Dual Function of the Voltage–Dependent $Ca^{2+}$ Channel $\alpha_2\delta$ Subunit in Current Stimulation and Subunit Interaction," *Neuron* 16:431–400, 1996.

Gurnett and Campbell, "Transmembrane Auxiliary Subunits of Voltage–Dependent Ion Channels," *J. Biol. Chem.*, 271(45):27975–27978, 1996.

Hardingham et al., "Mechanisms Controlling Gene Expression by Nuclear Calcium Signals," *Cell Calcium* 23(2/3):131–134, 1998.

Hermonat et al., "Use of Adeno–Associated Virus as a Mammalian DNA Cloning Vector: Transduction of Neomycin Resistance into Mammalian Tissue Culture Cells," *Proc. Natl. Acad. Sci. USA* 81:6466–6470, 1984.

Huse et al., "Generation of a Large Combinatorial Library of the Immunoglobulin Repertoire in Phage Lambda," *Science* 246:1275–1281, 1989.

Jones et al., "Mechanism of Auxiliary Subunit Modulation of Neuronal 1E Calcium Channels," *J. Gen. Physiol.* 112:125–143, 1998.

Jones, "Overview of Voltage–Dependent Calcium Channels," *J. Bioenergetics and Biomembranes* 30(4):299–312, 1998.

Juretic and Lucin, "The Preference Functions Method for Predicting Protein Helical Turns with Membrane Propensity," *J. Chem. Inf. Comput. Sci.* 38:575–585, 1998.

Kaplitt et al., "Expression of a Functional Foreign Gene in Adult Mammalian Brain Following In Vivo Transfer via a Herpes Simplex Virus Type 1 Defective Viral Vector," *Mol. Cell. Neurosci.* 2:320–330, 1991.

Klugbauer et al., "Molecular Diversity of the Calcium Channel $\alpha_2\delta$ Subunit," *J. Neurosci.* 19:684–691, 1999.

Kohler and Milstein, "Continuous Cultures of Fused Cells Secreting Antibody of Predefined Specificity," *Nature* 256:495–497, 1975.

Kozbor et al., "The Production of Monoclonal Antibodies from Human Lymphocytes," *Immun. Today* 4:72–79, 1983.

Kuo et al., "Efficient Gene Transfer Into Primary Murine Lymphocytes Obviating the Need for Drug Selection," *Blood* 82:845–852, 1993.

La Salle et al., "An Adenovirus Vector for Gene Transfer Into Neurons and Glia in the Brain," *Science* 259:988–990, 1993.

Lazar et al., "Transforming Growth Factor α: Mutation of Aspartic Acid 47 and Leucine 48 Results in Different Biological Activities," *Molecular and Cellular Biology* 8(3):1247–1252, 1988.

Lebkowski et al., "Adeno–Associated Virus: A Vector System for Efficient Introduction and Integration of DNA into a Variety of Mammalian Cell Types," *Mol. Cell. Biol.* 8:3988–3996, 1988.

Ledley, "Nonviral Gene Therapy: The Promise of Genes as Pharmaceutical Products," *Hum. Gene Ther.* 6:1129–1144, 1995.

Lehmann–Horn and Jurkatt–Roth, "Voltage–Gated Ion Channels and Hereditary Disease," *Physiol. Rev.* 79:1317–1372, 1999.

Lennon et al., "Calcium–Channel Antibodies in the Lambert–Eaton Syndrome and Other Paraneoplastic Syndromes," *New Engl. J. Med.* 332:1467–1474, 1995.

Lerman and Minna, "The 630–kb Lung Cancer Homozygous Deletion Region on Human Chromosome 3p21.3: Identification and Evaluation of the Resident Candidate Tumor Suppressor Genes," *Cancer Research* 60:6116–6133, 2000.

Letts et al., "The Mouse Stargazer Gene Encodes a Neuronal $Ca^{2+}$ Channel γ Subunit," *Nat. Genet.* 19:340–347, 1998.

Levrero et al., "Defective and Nondefective Adenovirus Vectors for Expressing Foreign Genes In Vitro and In Vivo," *Gene* 101:195–202, 1991.

Lory et al., "Towards a Unified Nomenclature Describing Voltage–Gated Calcium Channel Genes," *Hum. Genet.* 100:149–150, 1997.

Machy et al., "Gene Transfer from Targeted Liposomes to Specific Lymphoid Cells by Electrophoresis," *Proc. Natl. Acad. Sci. USA* 85:8027–8031, 1988.

Mann et al., "Construction of a Retrovirus Packaging Mutant and Its Use to Produce Helper–Free Defective Retrovirus," *Cell* 33:153–159, 1983.

Markowitz et al., "A Safe Packaging Line for Gene Transfer: Separating Viral Genes on Two Different Plasmids," *J Virol.* 62:1120–1124, 1988.

McCormick, "Human Gene Therapy: The First Round," *BioTechnol.* 3:689–693, 1985.

McEnery et al., "Differential Expression and Association of Calcium Channel Subunits in Development and Disease," *J. Bioenerg. Biomembr.* 30:409–418, 1998.

McEnery et al., "Isolation of the Mitochondrial Benzodiazepine Receptor: Association with the Voltage–Dependent Anion Channel and the Adenine Nucleotide Carrier," *Proc. Natl. Acad. Sci. USA* 89:3170–3174, 1992.

McEnery et al., "Purified Omega–Conotoxin GVIA Receptor of Rat Brain Resembles a Dihydropyridine–Sensitive L–Type Calcium Channel," *Proc. Natl. Acad. Sci. USA* 88:11095–11099, 1991.

Miller, "Calcium Channels Prove to be a Real Headache," *Trends Neurosci.* 20:189–192, 1997.

Miller and Rosman, "Improved Retroviral Vectors for Gene Transfer and Expression," *BioTechniques* 7:980–990, 1992.

Morton et al., "$\alpha_1$ and $\alpha_2$ Ca$^{2+}$ Channel Subunit Expression in Human Neuronal and Small Cell Carcinoma," *FASEB J.*, 8(11):884–888, 1994.

Nabel et al., "Direct Gene Transfer with DNA–Liposome Complexes in Melanoma: Expression, Biologic Activity, and Lack of Toxicity in Humans," *Proc. Natl. Acad. Sci. USA* 90:11307–11311, 1993.

Nagase et al., "Prediction of the Coding Sequences of Unidentified Human Genes, IX. The Complete Sequences of 100 New cDNA Clones from Brain Which Can Code for Large Proteins In Vitro," *DNA Res.* 5:31–39, 1998.

Nakaj and Kanehisa, "A Knowledge Base for Predicting Protein Localization Sites in Eukaryotic Cells," *Genomics* 14:897–911, 1992.

O'Neill et al., "The Lambert–Eaton Myasthenic Syndrome. A Review of 50 Cases," *Brain* 111:577–596, 1988.

Ophoff et al., "P/Q–Type Ca$^{2+}$ Channel Defects in Migraine, Ataxia and Epilepsy," *Trends Phys. Sci.*, 19:121–127, 1998.

Perez–Reyes and Schneider, "Molecular Biology of Calcium Channels," *Kidney Int.* 48:1111–1124, 1995.

Prestridge, "Predicting Pol II Promoter Sequences Using Transcription Factor Binding Sites," *J. Mol. Biol.* 249:923–932, 1995.

Qin et al., "Modulation of Human Neuronal $\alpha_{1E}$Type Calcium Channel by $\alpha_{2\delta-Subunit}$," *J. Gen. Physiol.*, 274(5 Pt. 1):C1324–1331, 1998.

Randall, "The Molecular Basis of Voltage–Gated Ca$^{2+}$ Channel Diversity: Is it Time for T?," *J. Membrane Biol.* 161:207–213, 1998.

Raymond et al., "Antibodies Against the $\beta$ Subunit of Voltage–Dependent Calcium Channels in Lambert–Eaton Myasthenic Syndrome," *Neurosci.* 90:269–277, 1999.

Rojas, "Ion Channels and Human Genetic Diseases," *News Physiol Sci.*, 11:36, 1996.

Sambrook et al., *Molecular Cloning, A Laboratory Manual*, Cold Spring Harbor Press, Plainview NY, 1989.

Samulski et al., "A Recombinant Plasmid From Which an Infectious Adeno–Associated Virus Genome Can be Excised In Vitro and its Use to Study Viral Replication," *J. Virol.* 61:3096–3101, 1987.

Samulski et al., "Helper–Free Stocks of Recombinant Adeno–Associated Viruses: Normal Integration Does Not Require Viral Gene Expression," *J. Virol.* 63:3822–3828, 1989.

Sanford et al., "Optimizing the Biolistic Process for Different Biological Applications," *Meth. Enzymol.* 217:483–509, 1993.

Schmid et al., "Immunochemical Analysis of Subunit Structures of 1,4–Dihydropyridine Receptors Associated with Voltage–Dependent Ca$^{2+}$ Channels in Skeletal, Cardiac, and Smooth Muscles," *Biochem.* 25:3492–3495, 1986.

Schmutte and Jones, "Involvement of DNA Methylation in Human Carcinogenesis," *Biol. Chem.* 379:377–388, 1998.

Sekido et al., "Cloning of a Breast Cancer Homozygous Deletion Junction Narrows the Region of Search for a 3p21.3 Tumor Suppressor Gene," *Oncogene* 16:3151–3157, 1998.

Sekido et al., "Neurofibromatosis Type 2 (NF2) Gene is Somatically Mutated in Mesothelioma But Not in Lung Cancer," *Cancer Res.* 55:1227–1231, 1995.

Sekido et al., "Human Semaphorins A(V) and IV Reside in the 3p21.3 Small Cell Lung Cancer Deletion Region and Demonstrate Distinct Expression Patterns," *Proc. Natl. Acad. Sci USA* 93:4120–4125, 1996.

Shaked et al., "Adenovirus–Mediated Gene Transfer in the Transplant Setting II. Successful Expression of Transferred cDNA in Syngeneic Liver Grafts," *Transplant.* 57:1508–1511, 1994.

Sharp and Campbell, "Characterization of the 1,4–Dihydropyridine Receptor Using Subunit–Specific Polyclonoal Antibodies. Evidence for a 32,000–Da Subunit," *J. Biol. Chem.* 264:2816–2825, 1989.

Shirokov et al., "Inactivation of Gating Currents of L–Type Calcium Channels. Specific Role of the $\alpha_2\delta$ Subunit," *J. Gen. Physiol.* 111:807–823, 1998.

Singer et al., "The Roles of the Subunits in the Function of the Calcium Channel," *Science* 253:1553–1557, 1991.

Smith et al., "Liposomes as Agents of DNA Transfer," *Biochim. Biophys. Acta* 1154:327–340, 1993.

Sonnhammer et al., "Pfam: Multiple Sequence Alignments and HMM–Profiles of Protein Domains," *Nucl. Acids Res.* 26:320–322, 1998.

Sonnhammer et al., "Pfam: A Comprehensive Database of Protein Domain Families Based on Seed Alignments," *Proteins: Structure, Function, and Genetics* 28:405–420, 1997.

Stefani et al., "Gabapentin Inhibits Calcium Currents in Isolated Rat Brain Neurons," *Neuropharmacol.* 37:83–91, 1998.

Stratford–Perricaudet et al., "Widespread Long–Term Gene Transfer to Mouse Skeletal Muscles and Heart," *J. Clin. Invest.* 90:626–630, 1992.

Striessnig et al., "Structural Basis of a Drug Binding to L Ca$^{2+}$ Channels," *TiPS* 19:108–115, 1998.

Suh–Kim et al., "Reconstitution of the Skeletal Muscle Dihydropyridine Receptor. Functional Interaction Among $\alpha 1$, $\beta$, $\gamma$ and $\alpha_2\delta$ Subunits," *Recept. Channels* 4:217–225, 1996.

Takamori, "An Autoimmune Channelopathy Associated with Cancer: Lambert–Eaton Myasthenic Syndrome," *Intern. Med.* 38:86–96, 1999.

Takamori et al., "Lambert–Eaton Myasthenic Syndrome as an Autoimmune Calcium–Channelopathy," *Neurosci. Res.* 36:183–191, 2000.

Tang et al., "Genetic Immunization is a Simple Method for Eliciting an Immune Response," *Nature* 356:152–154, 1992.

Toyota et al., "Aberrant Methylation in Gastric Cancer Associated with the CpG Island Methylator Phenotype," *Cancer Res.* 59:5438–5442, 1999.

Ulmer et al., "Heterologous Protection Against Influenza by Injection of DNA Encoding a Viral Protein," *Science* 259:1745–1748, 1993.

Walker and De Waard, "Subunit Interaction Sites in Voltage–Dependent Ca$^{2+}$ Channels: Role in Channel Function," *Trends Neurosci.* 21:148–154, 1998.

Wei et al., "Molecular Determinants of Cardiac Ca$^{2+}$ Channel Pharmacology," *J. Biol. Chem.* 270:27106–27111, 1995.

Lehmann–Horn and Jurkatt–Roth, "Molecular Pathophysiology of Voltage–Gated Ion Channels" pp. 196–268, in *Reviews of Physiology Biochemistry and Pharmacology* vol. 128, Blaustein et al. (eds.), Springer–Verlag, New York, 1999.

Voltz et al., "P/Q–Type Voltage–Gated Calcium Channel Antibodies in Paraneoplastic Disorders of the Central Nervous System," *Muscle & Nerve* 22:119–122, 1999.

Wei et al., "Construction of a 600–Kilobase Cosmid Clone Contig and Generation of a Transcriptional Map Surrounding the Lung Cancer Tumor Suppressor Gene (TSG) Locus on Human Chromosome 3p21.3: Progress Toward the Isolation of a Lung Cancer TSG," *Cancer Res.* 56:1487–1492, 1996.

Welling et al., "Hormonal Regulation of Calcium Current in Freshly Isolated Airway Smooth Muscle Cells," *Am. J. Physiol.* 262:L351–359, 1992.

Williams et al., "Structure and Functional Expression of $\alpha_1$, $\alpha_2$ and $\beta$ Subunits of a Novel Human Neuronal Calcium Channel Subtype," *Neuron* 8:71–84, 1992.

Williams et al., "Introduction of Foreign Genes into Tissues of Living Mice by DNA–Coated Microprojectiles," *Proc. Natl. Acad. Sci. USA* 88:2726–2730, 1991.

Wiser et al., "The $\alpha 2/\delta$ Subunit of Voltage Sensitive $Ca^{2+}$ Channels is a Single Transmembrane Extracellular Protein Which is Involved in Regulated Secretion," *FEBS Letters* 379:15–20, 1996.

Wistuba et al., "Molecular Damage in the Bronchial Epithelium of Current and Former Smokers," *J. Natl. Cancer Instit.* 89(18):1366–1377, 1997.

Wu et al., "Coordinated Leading– and Lagging–Strand Synthesis at the *Escherichia coli* DNA Replication Fork," *J. Biol. Chem.* 267(6):4030–4044, 1992.

Wu and Wu, "Receptor–Mediated Gene Delivery and Expression In Vivo," *J. Biol. Chem.* 263(29):14621–14624, 1988.

Wu and Wu, "Receptor–Mediated In Vitro Gene Transformation by a Soluble DNA Carrier System," *J. Biol. Chem.* 262(10):4429–4432, 1987.

\* cited by examiner

Outline of Positional Cloning of the Alpha2Delta-2 Gene in the Lung Cancer
Critical Region on the Short Arm of Human Chromosome 3

CALCIUM CHANNEL PROTEINS

This application is a divisional of U.S. patent application Ser. No. 09/470,443 filed Dec. 22, 1999, now U.S. Pat. No. 6,441,156, which claims the benefit of U.S. provisional application No. 60/114,359 filed Dec. 30, 1998, both of which are hereby incorporated by reference.

The invention was made with Government support under CA 71618, P50-CA70907, N538691, and NO 1-00-56000, awarded by the National Cancer Institute and the National Institutes of Health. The Government has certain rights in the invention.

FIELD OF THE INVENTION

The present invention relates to calcium channel compositions and methods of making and using same. In particular, the invention relates to calcium channel alpha2delta ($\alpha_2\delta$) subunits and nucleic acid sequences encoding them. These compositions are useful in methods for identifying compounds that modulate the activity of calcium channels and for identifying compounds as therapeutic for disease.

BACKGROUND OF THE INVENTION

Calcium channels are present in various tissues, have a central role in regulating intracellular calcium ion concentrations, and are implicated in several vital processes in animals (e.g., neurotransmitter release, muscle contraction, pacemaker activity, secretion of hormones and other substances, etc.). Thus, changes in calcium influx into cells which are mediated through calcium channels have been implicated in various human diseases such as disorders of the central nervous system and cardiovascular disease.

For example, changes to calcium influx into neuronal cells may be implicated in conditions such as epilepsy, stroke, brain trauma, Alzheimer's disease, multiinfarct dementia, other classes of dementia, Korsakoff's disease, neuropathy caused by a viral infection of the brain or spinal cord (e.g., human immunodeficiency viruses, etc.), amyotrophic lateral sclerosis, convulsions, seizures, Huntington's disease, amnesia, or damage to the nervous system resulting from reduced oxygen supply, poison or other toxic substances (See e.g., Goldin et al., U.S. Pat. No. 5,312,928).

Additionally, changes to calcium influx into cardiovascular cells may be implicated in conditions such as cardiac arrhythmia, angina pectoris, hypoxic damage to the cardiovascular system, ischemic damage to the cardiovascular system, myocardial infarction, and congestive heart failure (Goldin et al., supra). Other pathological conditions associated with elevated intracellular free calcium levels include muscular dystrophy and hypertension (Steinhardt et al., U.S. Pat. No. 5,559,004). While there has been limited success in expressing DNA encoding rabbit and rat calcium channel subunits, little is known about human calcium channel structure, function and gene expression. Additionally, there is limited knowledge in the art of the role of calcium channel types in cell growth control and abnormalities of calcium channels leading to cancer development.

In addition to the implication of calcium channels in animal (including human) diseases, a number of compounds which are currently used for treating various cardiovascular diseases in animals (including humans) are believed to exert their beneficial effects by modulating the functions of voltage-dependent calcium channels present in cells, such as cardiac cells and vascular smooth muscle cells. Nonetheless, there is a paucity of understanding of the pharmacology of compounds which interact with calcium channels. This paucity of understanding, together with the limited knowledge in the art of the human calcium channel types, the molecular nature of the human calcium channel subtypes, and the limited availability of pure preparations of specific calcium channel subtypes to use for evaluating the efficacy of calcium channel-modulating compounds has hampered the rational testing and screening of compounds that interact with the specific subtypes of human calcium channels to have desired therapeutic effects.

SUMMARY OF THE INVENTION

The invention provides calcium channel alpha2delta ($\alpha_2\delta$) subunits, as well as amino and nucleic acids encoding them. In one embodiment, the invention provides a substantially purified nucleic acid sequence consisting of at least a portion of a nucleotide sequence selected from the group consisting of (a) SEQ ID NO:1, the complement thereof, variants thereof, and homologs thereof, (b) SEQ ID NO:3, the complement thereof, variants thereof, and homologs thereof, and (c) SEQ ID NO:5, the complement thereof, variants thereof, and homologs thereof. In a preferred embodiment, the nucleic acid sequence encodes at least a portion of the amino acid sequence selected from the group consisting of SEQ ID NO:2 and variants thereof, SEQ ID NO:4 and variants thereof, and SEQ ID NO:6 and variants thereof. In a more preferred embodiment, the nucleic acid sequence is double-stranded. In an alternative more preferred embodiment, the nucleic acid sequence is single-stranded.

Without intending to limit the nucleic acid sequences of the invention to any particular type of encoded protein, in an alternative preferred embodiment, the nucleic acid sequence encodes a fusion protein. While it is not contemplated that the invention be limited to the type or nature of fusion partner in the fusion protein, in a more preferred embodiment, the fusion protein comprises a polypeptide selected from the group consisting of chloramphenicol acetyltransferase, luciferase, beta-galactosidase, green fluorescent protein, Myc protein, protein A, glutathione-S-transferase, FLAG tag, and polyhistidine.

In another alternative preferred embodiment, the nucleic acid sequence is contained on a recombinant expression vector. In a more preferred embodiment, the expression vector is contained within a host cell. While it is not contemplated that the invention be limited to the type of host cell, in a yet more preferred embodiment, the host cell is eukaryotic. In an even more preferred embodiment, the eukaryotic cell is selected from the group consisting of cancer cells and amphibian oocytes.

Also provided by the invention is a substantially purified amino acid sequence comprising at least a portion of an amino acid sequence selected from the group consisting of SEQ ID NO:2 and variants thereof, SEQ ID NO:4 and variants thereof, and SEQ ID NO:6 and variants thereof. In a preferred embodiment, the portion is part of a fusion protein. While not intending to limit the invention to any particular type or nature of fusion protein, in a more preferred embodiment, the fusion protein comprises a polypeptide selected from the group consisting of chloramphenicol acetyltransferase, luciferase, beta-galactosidase, protein A, glutathione-S-transferase, FlAG tag, and polyhistidine.

The invention further provides substantially purified amino acid sequences encoded by at least a portion of a nucleotide sequence selected from the group consisting of (a) SEQ ID NO:1, the complement thereof, variants thereof, and homologs thereof, (b) SEQ ID NO:3, the complement thereof, variants thereof, and homologs thereof, and (c) SEQ ID NO:5, the complement thereof, variants thereof, and homologs thereof.

The invention additionally provides methods for detecting presence of a nucleic acid sequence encoding at least a portion of a calcium channel protein, comprising: a) providing: i) a sample suspected of containing the nucleic acid sequence; and ii) at least a portion of a nucleotide sequence selected from the group consisting of (1) SEQ ID NO:1, the complement thereof, variants thereof, and homologs thereof, (2) SEQ ID NO:3, the complement thereof, variants thereof, and homologs thereof, and (3) SEQ ID NO:5, the complement thereof, variants thereof, and homologs thereof; b) combining the sample with at least a portion of the nucleotide sequence under conditions such that the nucleic acid hybridizes with at least a portion of the nucleotide sequence; and c) detecting the hybridization. Although it is not contemplated that the invention be limited to the level of stringency of hybridization, in one preferred embodiment, the hybridization is under conditions of low stringency. In another prefer-red embodiment, the hybridization is under conditions of high stringency. Furthermore, it is contemplated that the invention will also be used in various assays to detect mRNA using these sequences (i.e., SEQ ID NOS: 1, 3, and 5) including, but not limited to microassays.

The invention also provides methods for producing at least a portion of a calcium channel protein, comprising: a) providing: i) a recombinant expression vector comprising a nucleic acid sequence encoding at least a portion of an amino acid sequence selected from the group consisting of SEQ ID NO:2 and variants thereof, SEQ ID NO:4 and variants thereof, and SEQ ID NO:6 and variants thereof; and ii) a host cell; and b) introducing the vector into the host cell under conditions such that the host cell expresses the portion of the amino acid sequence. In one preferred embodiment, the method further comprises step c) recovering the expressed amino acid sequence (or portion thereof). While not intending to limit the invention to the type or nature of host cell, in an alternative preferred embodiment, the host cell is eukaryotic. In a more preferred embodiment, the eukaryotic host cell is selected from the group consisting of cancer cells and amphibian oocytes.

The invention also provides methods for screening test compounds for modulating calcium channel activity, comprising: a) providing: i) the test compound; ii) a calcium channel selective ion; iii) a control cell; and iv) a host cell comprising a cell membrane and expressing heterologous nucleic acid sequences encoding: 1) calcium channel $\alpha_1$ subunit; and 2) at least a portion of an amino acid sequence selected from the group consisting of SEQ ID NO:2 and variants thereof, SEQ ID NO:4 and variants thereof, and SEQ ID NO:6 and variants thereof; b) contacting the host cell with the test compound and with the molecule to produce a treated host cell; c) depolarizing the cell membrane of the treated host cell under conditions such that the molecule enters the cell through a functional calcium channel; and d) detecting a difference between current flowing into the treated host cell and current flowing into a control cell, thereby identifying the test compound as a compound capable of modulating calcium channel activity. In one preferred embodiment, the method further comprises, prior to the depolarizing, maintaining the treated host cell at a holding potential that substantially inactivates endogenous calcium channels. In another preferred embodiment, the method further comprises, prior to or simultaneously with the step of contacting the host cell with the test compound, contacting the host cell with a calcium channel agonist, wherein the test compound is tested for activity as an antagonist. In yet another preferred embodiment, the host cell further expresses calcium channel beta ($\beta$) subunit. In another preferred embodiment, the host cell further expresses calcium channel beta ($\beta$) subunit and gamma ($\gamma$) subunit. Without intending to limit the type or source of host cell, in yet another preferred embodiment, the host cell is eukaryotic. In a more preferred embodiment, the eukaryotic host cell is selected from the group consisting of cancer cells and amphibian oocytes.

Also provided herein is a method of generating antibodies directed against at least a portion of a calcium channel protein, comprising: a) providing: i) at least a portion of an amino acid sequence selected from the group consisting of SEQ ID NO:2 and variants thereof, SEQ ID NO:4 and variants thereof, and SEQ ID NO:6 and variants thereof; and ii) a host; b) immunizing the host with at least a portion of the amino acid sequence so as to generate an antibody; and c) collecting the antibody from the host. In one preferred embodiment, the method further comprises step d) purifying the antibody. Without limiting the type of host cell, in another preferred embodiment, the host is a mammal. In yet another preferred embodiment, the mammal is a mouse.

The invention further provides an antibody raised according to the method described in the preceding paragraph, i.e., by a) providing: i) at least a portion of an amino acid sequence selected from the group consisting of SEQ ID NO:2 and variants thereof, SEQ ID NO:4 and variants thereof, and SEQ ID NO:6 and variants thereof; and ii) a host; b) immunizing the host with at least a portion of the amino acid sequence so as to generate antibody; and c) collecting the antibody from the host. In one preferred embodiment, the antibody is monoclonal. In another preferred embodiment, the antibody is polyclonal. In still further embodiments, the present invention provides methods and compositions for genetic immunization for the production of antibodies (e.g., by injecting expression plasmid into an animal).

Also provided herein is an antibody which specifically binds to an amino acid sequence selected from the group consisting of SEQ ID NO:2 and variants thereof, SEQ ID NO:4 and variants thereof, and SEQ ID NO:6 and variants thereof. In a preferred embodiment, the antibody is monoclonal. In another preferred embodiment, the antibody is polyclonal.

The invention also provides a method of detecting expression of at least a portion of a calcium channel protein, comprising: a) providing: i) a sample suspected of expressing the calcium channel protein; and ii) an antibody raised according to the above-described method (i.e., by a) providing: i) at least a portion of an amino acid sequence selected from the group consisting of SEQ ID NO:2 and variants thereof, SEQ ID NO:4 and variants thereof, and SEQ ID NO:6 and variants thereof; and ii) a host; b) immunizing the host with at least a portion of the amino acid sequence so as to generate an antibody; and c) collecting the antibody from the host); b) combining the sample and the antibody under conditions such that the antibody binds to the calcium channel protein; and c) detecting the binding between the antibody and the calcium channel protein in the sample.

The present invention additionally provides methods for producing transgenic non-human animals, wherein the animal expresses a reduced level of calcium channel $\alpha_2\delta$ subunit relative to a corresponding wild-type animal, comprising: a) providing: i) an embryonic stem cell comprising wild-type calcium channel $\alpha_2\delta$-subunit genes; ii) a blastocyst of a non-human animal; iii) a pseudopregnant non-human animal; and iv) an oligonucleotide sequence comprising at least a portion of a non-human nucleotide sequence homologous to a nucleic acid sequence selected from the group consisting of (1) SEQ ID NO:1, complements thereof and variants thereof, (2) SEQ ID NO:3, complements thereof and variants thereof, and (3) SEQ ID NO:5, complements thereof and variants thereof; b) introducing the oligonucleotide sequence into the embryonic stem cell under conditions such that the oligonucleotide sequence is homologously recombined into at least one of the wild-type calcium channel $\alpha_2\delta$-subunit genes in the genome of the embryonic stem cell to produce a treated embryonic stem cell; c) injecting the treated embryonic stem cell into the blastocyst to produce an injected blastocyst; d) introducing the injected blastocyst into the pseudopregnant non-human animal; and e) permitting the pseudopregnant animal to deliver progeny comprising the homologously recombined oligonucleotide, wherein the progeny express a reduced level of calcium channel $\alpha_2\delta$-subunit relative to a corresponding wild-type animal. In one preferred embodiment, the transgenic non-human animal is selected from the order Rodentia. In a more preferred embodiment, the transgenic non-human animal is a mouse.

The invention also provides methods for producing transgenic non-human animals, wherein the animal expresses reduced activity of calcium channel $\alpha_2\delta$ subunit relative to a corresponding wild-type animal, comprising: a) providing: i) an embryonic stem cell comprising wild-type calcium channel $\alpha_2\delta$-subunit genes; ii) a blastocyst of a non-human animal; iii) a pseudopregnant non-human animal; and iv) an oligonucleotide sequence comprising at least a portion of a non-human nucleotide sequence homologous to a nucleic acid sequence selected from the group consisting of (1) SEQ ID NO:1, complements thereof and variants thereof, (2) SEQ ID NO:3, complement thereof and variants thereof, and (3) SEQ ID NO:5, complements thereof and variants thereof, wherein at least portion of the nucleotide sequence comprises one or more mutations selected from the group consisting of deletion, insertion and point mutation(s); b) introducing the oligonucleotide sequence into the embryonic stem cell under conditions such that the oligonucleotide sequence is homologously recombined into at least one of the wild-type calcium channel $\alpha_2\delta$-subunit genes in the genome of the embryonic stem cell to produce a treated embryonic stem cell; c) injecting the treated embryonic stem cell into the blastocyst to produce an injected blastocyst; d) introducing the injected blastocyst into the pseudopregnant non-human animal; and e) permitting the pseudopregnant animal to deliver progeny comprising the homologously recombined oligonucleotide, wherein the progeny express reduced activity of calcium channel $\alpha_2\delta$-subunit relative to a corresponding wild-type animal. In one preferred embodiment, the transgenic non-human animal is selected from the order Rodentia. In a more preferred embodiment, the transgenic non-human animal is a mouse.

Additionally provided herein is a method for identifying a therapeutic compound, comprising: a) providing: i) a transgenic non-human animal produced by the method described in either of the previous two paragraphs; and ii) a composition comprising the compound; and b) administering the compound to the transgenic non-human animal to produce a treated animal. While it is not intended that the transgenic animal be limited to a particular type, in one preferred embodiment, the transgenic animal has cancer. In a more preferred embodiment, the cancer is selected from the group consisting of lung cancer, breast cancer, nasopharyngeal cancer, cervical cancer, head cancer and neck cancer. In yet a more preferred embodiment, the lung cancer is selected from the group consisting of small cell carcinoma and non small cell carcinoma. In another preferred embodiment, the transgenic animal has a neurological disease selected from the group consisting of epilepsy, stroke, brain trauma, Alzheimer's disease, multiinfarct dementia, amyotrophic lateral sclerosis, convulsions, seizures, Huntington's disease, and amnesia. In yet another preferred embodiment, the transgenic animal has a cardiovascular disease selected from the group consisting of cardiac arrhythmia, angina pectoris, hypoxic damage to the cardiovascular system, ischemic damage to the cardiovascular system, myocardial infarction, and congestive heart failure. In a further preferred embodiment, the transgenic animal has Lambert-Eton myasthenic syndrome.

In still further embodiments, the present invention provides methods for treatment of human tumors in non-human animals. For example, it is contemplated that the methods for identifying therapeutic compounds as described herein will find use in the treatment of human tumors in immunodeficient mice (e.g. nude and/or SCID [severe combined immunodeficiency] mice) or other animals.

DEFINITIONS

Figure 1:
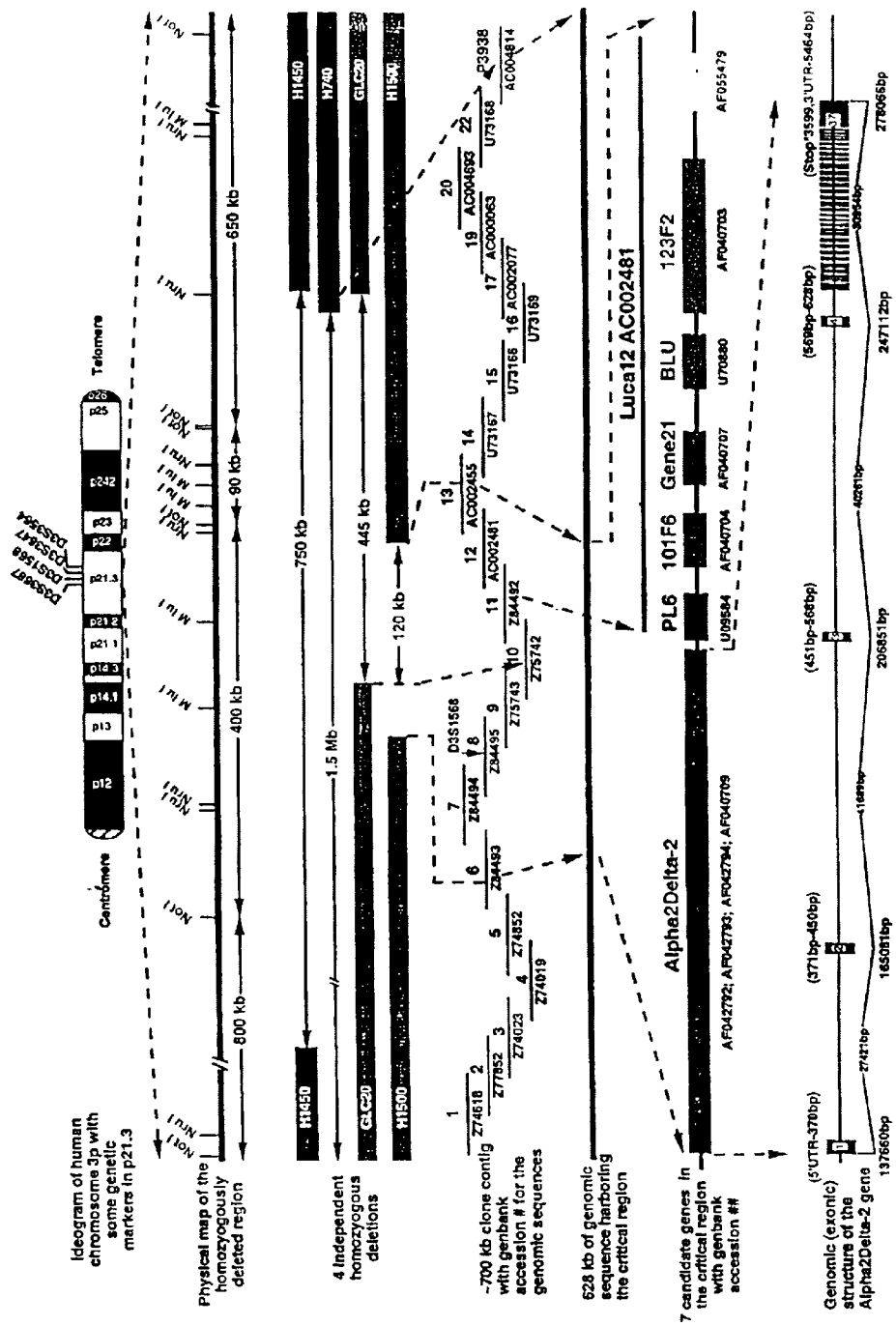
FIG. 1 provides a schematic outline of the positional cloning of the $\alpha_2\delta$ gene from human chromosome region 3p21.3.

To facilitate an understanding of the invention, a number of terms are defined below.

As used herein the term "portion" when made in reference to a nucleic acid sequence refers to a fragment of that sequence. The fragment may range in size from five (5) contiguous nucleotide residues to the entire nucleic acid sequence minus one nucleic acid residue. Thus, "a nucleic acid sequence comprising at least a portion of a nucleotide sequence" comprises from (5) contiguous nucleotide residues of the nucleotide sequence to the entire nucleotide sequence.

The term "portion" when used in reference to a protein (as in a "portion of a given protein") refers to fragments of that protein. The fragments may range in size from four (4) contiguous amino acid residues to the entire amino acid sequence minus one amino acid residue. Thus, a polypeptide sequence comprising "at least a portion of an amino acid sequence" comprises from four (4) contiguous amino acid residues of the amino acid sequence to the entire amino acid sequence.

As used herein, the term "purified" or "to purify" refers to the removal of undesired components from a sample. For example, where recombinant $\alpha_2\delta$ polypeptides are expressed in eukaryotic host cells, the $\alpha_2\delta$ polypeptides are purified by the removal of host cell proteins thereby increasing the percent of recombinant $\alpha_2\alpha$ polypeptides in the sample.

As used herein, the term "substantially purified" refers to molecules, either nucleic or amino acid sequences, that are removed from their natural environment such that they are at least 60% free, preferably 75% free, and more preferably 90% free from other components with which they are naturally associated.

The term "recombinant DNA molecule" as used herein refers to a DNA molecule which is comprised of segments of DNA joined together by means of molecular biological techniques. The term "recombinant protein" or "recombinant polypeptide" as used herein refers to a protein molecule which is expressed using a recombinant DNA molecule. A "recombinant calcium channel" protein refers to a calcium channel that contains one or more recombinant calcium channel subunits or one or more recombinant portions of at least one calcium channel subunit.

The term "oligonucleotide" as used herein is defined as a molecule containing from two (2) to one hundred (100), preferably from ten (10) to fifty (50), and more preferably from twenty (20) to thirty (30) deoxyribonucleotides or ribonucleotides. Oligonucleotides may be generated by several methods known in the art including, but not limited to, chemical synthesis, DNA replication, reverse transcription, restriction digestion, polymerase chain reaction, and the like.

The term "transfection" as used herein refers to the introduction of a transgene into a cell. The term "transgene" as used herein refers to any nucleic acid sequence which is introduced into the genome of a cell by experimental manipulations (e.g., using methods including, but not limited to recombinant cloning). A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

Transfection may be stable or transient. The term "stable transfection" or "stably transfected" refers to the introduction and integration of a transgene into the genome of the transfected cell. The term "stable transfectant" refers to a cell which has stably integrated one or more transgenes into the genomic DNA. The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

The term "foreign gene" refers to any nucleic acid (e.g., gene sequence) which is introduced into the genome of an animal by experimental manipulations and may include gene sequences found in that animal so long as the introduced gene contains some modification (e.g., a point mutation, the presence of a selectable marker gene, etc.) relative to the naturally-occurring gene.

The term "gene" refers to a DNA sequence that comprises control and coding sequences necessary for the production of RNA or a polypeptide. The polypeptide can be encoded by a full length coding sequence or by any portion of the coding sequence.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

A "variant" of a nucleic acid sequence is defined as a nucleotide sequence which differs from the nucleic acid sequence (e.g., by having deletions, insertions, and substitutions) that may be detected using hybridization assays or sequencing.

A "variant" of a polypeptide sequence is defined as an amino acid sequence which differs by one or more amino acids from the polypeptide sequence. The variant may have "conservative" changes, wherein a substituted amino acid has similar structural or chemical properties (e.g., replacement of leucine with isoleucine). More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

A nucleic acid sequence which is a "homolog" of a $\alpha_2\delta$ nucleic acids sequence (e.g., SEQ ID NOs: 1, 3, and 5) is defined herein as a nucleic acid sequence which exhibits more than 56%, more preferably at least 70%, and most preferably at least 95% identity to the $\alpha_2\delta$ nucleic acid sequence. Alternatively, a homolog of a $\alpha_2\delta$ nucleic acid sequence (e.g., SEQ ID NOs: 1, 3, and 5) is defined as a nucleic acid sequence which encodes a biologically active $\alpha_2\delta$ subunit polypeptide.

The term "substantially homologous" when used in reference to a double-stranded nucleic acid sequence such as a cDNA or genomic clone refers to any nucleic acid sequence which is capable of hybridizing to either or both strands of the double-stranded nucleic acid sequence of interest under conditions of low stringency.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains the following per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is the to be equivalent to the hybridization condition of interest if this other hybridization condition also results in hybridization of the first nucleic acid sequence with the other nucleic acid sequences that have from 50% to 70% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

The term "hybridization" as used herein includes "any process by which a strand of nucleic acid joins with a complementary strand through base pairing." (See e.g., J. Coombs, *Dictionary of Biotechnology*, Stockton Press, New York N.Y. [1994]). Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

The terms "alpha2delta," "$\alpha_2\delta$," "alpha2delta subunit," "$\alpha_2\delta$ subunit" when made in reference to a polypeptide sequence are used interchangeably to refer to a calcium channel subunit type. The $\alpha_2\delta$ subunit type comprises subunit subtypes, also referred to as subunit isoforms (e.g., isoforms I and II disclosed herein), which arise as a result of translation of splice variants of the primary transcript of the $\alpha_2\delta$ gene.

As used herein, a "splice variant" refers to an RNA sequence produced by processing of a primary transcript (i.e., pre-mRNA) of a genomic DNA sequence. Pre-mRNAs (also referred to as heterogenous nuclear RNA or mRNA) in higher eukaryotes contain multiple introns which must be precisely excised by RNA splicing prior to transport over the nuclear membrane into the cytoplasm for translation. Differential processing of the primary transcript results in more than one RNA sequence, wherein each RNA sequence is referred to as a splice variant of the primary DNA transcript. Splice variants may occur within a single tissue type or among different tissues (e.g., neuronal tissue, muscle tissue, etc.) Splice variants which occur among different tissues are referred to as "tissue specific variants."

The term "calcium channel selective ion" is an ion that is capable of entering, or of being blocked from entering, a cell through a calcium channel which spans a cellular membrane under conditions which would permit or block the entry of calcium ions ($Ca^{++}$) into the cell. Calcium channel selective ions are exemplified, but not limited to, $Ca^{++}$ (calcium ions) and $Ba^{++}$ (barium ions).

A "calcium channel" as used herein refers to a peptide sequence comprising at least alpha 1($\alpha_1$) subunit. More preferably, a calcium channel further comprises alpha 2 ($\alpha_2$), beta ($\delta$), gamma ($\gamma$) and delta ($\delta$) subunits. The nucleic acid and amino acid sequences of calcium channel subunits in different organisms (e.g., human, rabbit, and rat) and in different tissues of the same organism (e.g., neuronal tissue, cardiovascular tissue) are known in the art (See e.g., Ellis et al., Science 241(4873):1661–4 [1988]; Williams et al., Neuron 8(1):71–84 [1992]; Ellis et al. U.S. Pat. No. 5,686,241 hereby incorporated by reference; and Harpold et al., U.S. Pat. No. 5,792,846 hereby incorporated by reference).

The terms "functional calcium channel" and "biologically active calcium channel" interchangeably refer to a calcium channel which allows entry into a cell of a calcium channel selective ion in response to a stimulus. Such entry may be determined by measuring the amount of current which flows through the calcium channel in response to the stimulus. Alternatively, a functional calcium channel refers to a calcium channel which binds ligands that have affinity for a calcium channel. For ligand binding assays of a recombinant calcium channel, it is preferred that the host cell which is used for testing the function of the recombinant calcium channel not produce endogenous calcium channel subunits that are of a type or in an amount that interferes with the detection of the recombinant calcium channel. Methods for determining the function of a calcium channel are known in the art, such as those described in Harpold et al., supra.

The terms "functional calcium channel subunit" and "biologically active calcium channel subunit" are equivalent terms which refer to a calcium channel subunit which is capable of associating with at least one other calcium channel subunit to form a functional calcium channel.

The term "compound that modulates calcium channel activity" and grammatical equivalents thereof refers to a compound that alters (i.e., reduces or increases) the ability of a calcium channel to pass calcium channel selective ions as measured by, for example, the current flowing through the calcium channel. Such compounds include, but are not limited to, calcium channel agonists (e.g., Goldin et al., U.S. Pat. No. 5,312,928, herein incorporated by reference) and antagonists, and compounds that exert their effect on the activity of the calcium channel directly or indirectly.

The term "agonist" refers to a molecule which, when interacting with a biologically active molecule, causes an enhancement in the activity of the biologically active molecule. Agonists may include proteins, nucleic acids, carbohydrates, or any other molecules which bind and/or interact with biologically active molecules. For example, an agonist can alter the activity of gene transcription by interacting with RNA polymerase directly, or through a transcription factor.

The terms "antagonist" or "inhibitor" refer to molecules which, when interacting with a biologically active molecule, block or inhibit the biological activity of the biologically active molecule. Antagonists and inhibitors may include proteins, nucleic acids, carbohydrates, or any other molecules which bind and/or interact with biologically active molecules. Inhibitors and antagonists can affect the biology of entire cells, organs, or organisms (e.g., an inhibitor that slows tumor growth).

The term "modulate" refers to a change or an alteration in the biological activity of a biologically active molecule. Modulation may be an increase or a decrease in activity, a change in binding characteristics, or any other change in the biological, functional, and/or immunological properties of biologically active molecules.

The term "biologically active" refers to molecules, compounds, etc., with structural, regulatory, and/or biochemical functions in an organism, cell, and/or organ.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia.

The term "order Rodentia" refers to rodents (i.e., placental mammals in the Class Euthria, which also include the family Muridae (e.g., rats and mice)), most preferably mice.

A "transgenic animal" as used herein refers to an animal that includes a transgene which is inserted into an embryonal cell and which becomes integrated into the genome either of somatic and/or germ line cells of the animal which develops from that embryonal cell, or of an offspring of such an animal.

As used herein, the term "therapeutic" when made in reference to a compound refers to a compound which is capable of reducing, delaying, or eliminating one or more undesirable pathologic effects in a subject.

DESCRIPTION OF THE INVENTION

The invention provides nucleic acid sequences encoding calcium channel $\alpha_2\delta$ subunits. In particular, the invention provides cDNA sequences which are derived from splice variants of the calcium channel $\alpha_2\delta$ gene and which encode $\alpha_2\alpha$ protein isoforms (e.g., isoforms I and II). Also provided herein are polypeptide sequences of calcium channel $\alpha_2\delta$ subunit isoforms. The compositions of the invention are useful in the detection, prevention and treatment of diseases such as cancer, autoimmune, cardiovascular, and neurological diseases. The compositions provided herein are also useful for the generation of in vitro and in vivo animal models for diseases (e.g., cancer, autoimmune, cardiovascular and neurological diseases) which in turn may be used to screen compounds for their therapeutic effects on these diseases.

The nucleic acids of the invention were discovered during a search by the inventors for a lung cancer and breast cancer tumor suppressor gene in the chromosome region 3p21.3, which the inventors considered to be one of the earliest regions undergoing genetic change in the smoking damaged bronchial epithelium and to thus to be associated with the development of lung and breast cancers. Furthermore, frequent allele loss and occasional homozygous deletions have been found in lung, breast, other human tumors (Wei et al., Cancer Res., 56(7):1487–1992 [1996]). As the lung cancer epidemic kills annually 150,000 victims in the USA, more deaths than due to colon, prostate, and breast cancer combined, much research has been conducted in the area of lung cancer diagnosis, prognosis, treatment, and prevention. The magnitude of this epidemic has heightened efforts to discover the genetic origin of lung cancer. While tobacco smoking is a well-established environmental trigger in lung carcinogenesis, the art's understanding of the genetic etiology of lung cancer is still incomplete.

Based on evidence from genetic mapping studies including overlapping homozygous deletions, it was the inventors' consideration that a tumor suppressor gene was located in the chromosome 3p21.3 band. To this end, the present inventors constructed a ~700 kb long clone contig (i.e., a continuous sequence of DNA that has been assembled from overlapping cloned DNA fragments) covering the lung cancer region in 3p21.3 and isolated a number of genes residing on the contig (Wei et al., Cancer Res., 6(7):1487–92 [1996]). This 700 kb segment has been sequenced jointly by the Washington University Sequencing Center (Saint Louis, Mo.) and the Sanger Sequencing Centre (Hixton, UK). The inventors used this sequence as a tool to detect and clone more genes from the region by in silico initiated methods. In addition, by discovering and mapping a new overlapping homozygous deletion in the region, the inventors narrowed the critical area to approximately 120 kb, thus limiting the search for the lung and breast cancer gene to a set of eight resident genes. One of these genes was identified by the inventors using bioinformatics methods as a new calcium channel $\delta_2\delta$ subunit gene. It was surprising that the new calcium channel $\delta_2\delta$ subunit gene was identified by the inventors to be located in a region of this contig that was different from the region which was reported in the art to contain the sought-after lung cancer tumor suppressor gene.

Importantly, the present inventors also discovered that expression of the $\alpha_2\delta$ subunit was shut off in a majority of lung cancer cells. This indicated to the inventors that an alteration in calcium homeostasis in cancer cells leads to malignancy. Sequence analysis of the $\alpha_2\delta$ gene and deduced protein identified this gene as a new calcium channel $\alpha_2\delta$ subunit gene.

The $\alpha_2\delta$ subunit gene disclosed herein is located in the lung cancer critical region on 3p21.3, is about 140 kb long, contains at least 37 exons, and encodes at least three differentially spliced mRNA isoforms of about 5.3–5.5 kb in length differing at their 5' ends. Data disclosed herein reveals that, by Northern analysis, the $\alpha_2\delta$ subunits are highly expressed in lung and testis, moderately expressed in brain, heart, skeletal muscle, pancreas, small intestine, ovary, and spleen, with low levels of expression in kidney, and undetectable levels of expression in liver, thymus, and colon.

The tissue distribution of mRNA for the three $\alpha_2\delta$ subunits is very different (Klugbauer et al., J. Neurosci., 19(2):684–691 [1999]; and Angelotti and Hofmann, supra). All three genes are expressed in brain, which is the only tissue that expresses $\alpha_2\delta$-3. The $\alpha_2\delta$-1 gene is highly expressed in skeletal muscle, where little or no expression of $\alpha_2\delta$-2 was found. Both $\alpha_2\delta$-1 and -2 are expressed in heart. The $\alpha_2\delta$-2 gene is highly expressed in lung where the expression of $\beta_2\delta$-1 is low. It is contemplated that the present invention will be used to determine which cells in the lung express $\alpha_2\delta$-2. In fact, the present inventors have shown that several lung cancers representing different lung epithelial types can express $\alpha_2\delta$-2. Thus, it is contemplated that some normal lung epithelial cells also express $\alpha_2\delta$-2. In this regard, it is also interesting to note that $\alpha$1C was cloned from lung cDNA libraries (Biel et al., FEBS Lett., 269(2): 409–412[1990]), and L-type currents have been characterized from tracheal smooth muscle (Welling et al,. Am. J. Physiol., 262(3 Pt 1):L351–359[1992]). The only $\delta$ subunit detected in lung mRNA is $\delta_2$ (Castellano and Perez-Reyes, Biochem. Soc. Trans., 22(2):483–488[1994]). Therefore, the minimum subunit composition of lung L-type channels can be deduced as $\alpha$1C$\alpha_2\delta$-2$\delta_2$.

It was noted that the results obtained during the development of the present invention do not agree with those of Klugbauer et al. (Klugbauer et al., supra), who found abundant cross-reactive material from what they reported to be $\alpha_2\delta$-2, in mRNA from skeletal muscle, pancreas, and heart, with hardly any signal from lung (Klugbauer et al., supra). It is believed that the expression pattern described herein is the correct one for $\alpha_2\delta$-2, since the probes used for Northern blotting were derived from the whole coding region of $\alpha_2\delta$-2, while authors of the Klugbauer report used only a 356 nucleotide probe from the coding region. In addition, the results of tissue expression pattern in independent Northern blot experiments were confirmed using two additional different short CACNA2D2 probes. The result of the cDNA screening also supports the high expression of $\alpha_2\delta$-2 in lung, as 120 $\alpha_2\delta$-2 clones were obtained from a screening of 1 million clones of a lung cDNA library. A possible explanation for the discrepancy could be that Klugbauer et al.'s probe cross-reacted with $\alpha_2\delta$-1, since it has an expression pattern very similar to what they reported for $\alpha_2\delta$-2 (Angelotti and Hofmann, FEBS Lett., 397(2–3):331–337[1996]). Furthermore, it is unlikely that $\alpha_2\delta$-2 is highly expressed in skeletal muscle, because $\alpha_2\delta$ proteins were purified from that tissue and only the sequence of $\alpha_2\delta$-1 was detected (Ellis et al., Science 214(4873):1661–1663[1988]).

The function of the gene product of the new $\alpha_2\delta$-2 gene was tested in Xenopus oocytes by co-expressing $\alpha_2\delta$-2 cRNAs along with a representative member of the three families of calcium subunit al subunits. In these experiments, three $\alpha$1 subunits were investigated for their effect on currents. The $\alpha$1 subunits were chosen to represent each of the three subfamilies of $Ca^{2+}$ channels: $Ca_v1.2$ or $\alpha$1C, $Ca_v2.2$ or $\alpha$1B, and an LVA channel $Ca_v3.1$ or $\alpha$1G. In each case, $\alpha_2\delta$-2 was able to stimulate functional expression. No effect was observed on the biophysical properties of the current, suggesting that $\alpha_2\delta$-2 simply increased the number of functional channels at the plasma membrane. Similar results were obtained with $\alpha_2\delta$-1 on the expression of $\alpha$1G in both COS cells and Xenopus oocytes (Dolphin et al., J. Physiol., 519.1:35–45 [1999]). Surprisingly, a pattern of expression was identified that was different from the other $\alpha_2\delta$ subunit, and $\alpha_2\delta$-2 was found to enhance the activity of the calcium $\alpha$1 subunits.

Co-expression studies of $\alpha_2\delta$-2 plus $\alpha$1B also included the $\delta_3$ subunit. In these experiments, the largest stimulatory effect on expression was observed. Some studies have reported a synergistic action of $\alpha_2$ and $\delta$ on $\alpha$1B expression (See e.g., Brust et al., Neuropharmacol., 32(11:1089–1102 [1993]). The experiments with $\alpha$1C did not include a $\delta$ subunit because they stimulate current so much already that it has been difficult to see any effect of $\alpha_2\delta$ at the whole cell level (Wei et al., J. Biol. Chem., 270(45):27106–27111 [1995]).

The invention discloses that the $\delta_2\delta$ subunit gene is a candidate tumor suppressor gene which is involved in the origin of cancers (e.g., lung cancer, breast cancer, etc.). Indeed, interest in the physiological roles of $Ca^{2+}$ channels has increased, due to finding that mutations in their genes can lead to human diseases (Lehmann-Hom and Jurkatt-Roth, Physiol. Rev., 79:1317–1372 [1997]). In addition to potential role(s) in cancer pathogenesis, defects in the auxiliary subunits of $Ca^{2+}$ channels have been described in mouse models of absence epilepsy. These include mouse strains that have lost the expression of $\beta_4$, and the recently discovered $\gamma_2$ subunit (Lelts et al., Nat. Genet., 19:340–347 [1998]; and Burgess et al., Cell 88:385–392 [1997]). In this regard after CACNA2D2 was cloned, it was noted with great interest that the syntenic region in the mouse (mouse chromosome 9, 59.0–60.0 cM, contains the mouse mutant ducky and also 5 other flanking genes (CISH, GNAI2, GNAT, and HYALI), that were identified in the ~600 kb region (Wei et al., Cancer Res., 56(7):1487–1492 [1996]; and GenBank deposits AF132297 for CISH and U03056 for HYALI). The partial mouse cDNA sequence was found to be 92% identical to the human $\delta_2\delta$-2 sequence (GenBank #AF169633.1). Indeed, preliminary evidence suggests that loss of $\delta_2\delta$-2 expression leads to the epileptic phenotype, ducky (Barclay et al., Epilepsia 40(Suppl. 2):137 [1990]). Histological examination of mouse ducky mutants reveals atrophy of the cerebellum, medulla oblongata, and spinal cord (Meier, Acta Neurol., 11:15–28 [1968]). These mice develop a spike-and-wave phenotype in the electroencephalogram, which is similar to that observed in absence epilepsy patients. Thus, it is contemplated that the present invention will find use in the development of methods to identify and test for the presence of inherited defects in CACNA2D2 in other species, including humans. It is also contemplated that the present invention will find use in assessing calcium channel defects associated with epileptic and other pathological phenotypes.

The invention further discloses that biallelic inactivation (i.e., inactivation of two alleles leading to complete loss-of-function) or monoallelic inactivation (i.e., inactivation of one allele leading to haploinsufficiency) of the $\alpha_2\delta$ subunit gene represents the critical rate-limiting step in the development of cancer. Thus, it is clear that the present inventors' discovery of a novel $\alpha_2\delta$ subunit of calcium channels provides compositions which are useful in the detection, prevention and treatment of cancer, as well as other diseases (e.g., epilepsy, migraine, episodic ataxia, stroke, brain trauma, Alzheimer's disease, multiinfarct dementia, Korsakoff's disease, amyotrophic lateral sclerosis, convulsions, seizures, Huntington's disease, amnesia, cardiac arrhythmia, angina pectoris, hypoxic damage to the cardiovascular system, ischemic damage to the cardiovascular system, myocardial infarction, congestive heart failure, muscular dystrophy, hypertension, etc.) which implicate calcium channels.

In addition, the present inventors have also discovered that the $\alpha_2\delta$ subunit gene is involved in lung carcinogenesis based on their observation of reduced levels of expression of the $\alpha_2\delta$ subunit gene in lung cancer (e.g., small cell lung cancer and non-small cell lung cancer) cell lines as compared to normal lung cells. The present inventors have also discovered that the $\alpha_2\delta$ subunit gene is implicated in breast carcinogenesis based on a homozygous deletion of the gene in a breast cancer cell line and in its primary tumor.

Furthermore, a clinical connection between voltage dependent calcium channels and lung cancer is well established by the Lambert-Eaton myasthenic syndrome (LEMS) seen in some small cell lung cancer patients (Takamori, Intern. Med., 38(2):86–96 [1999]). LEMS is a human autoimmune disorder that impairs neuromuscular transmission such that patients with this syndrome have a defect in the $Ca^{2+}$ dependent quantal release of acetylcholine from motor nerve terminals (O'Neill et all., Brain 111 (Pt. 3):577–596 [1988]). In this syndrome, patients develop antibodies (presumably initiated by expression of the channel proteins in their small cell lung cancer) that react with voltage-gated calcium channel polypeptides which block depolarization-induced $Ca^{2+}$ influx leading to the myasthenia (Lennon et al., New Engl. J. Med., 332(22):146701474 [1995]; Raymond et al., Neurosci., 90(1):269–277 [1999] and Voltz et al., Muscle Nerve 22(1):119–122 [1999]). During the development of the present invention the ability of $\alpha_2\delta$-2 to functionally interact with the T-type channel subunit $\alpha$1G was observed. In addition, Toyota et al. reported that CACNA1G encoding this subunit could have its expression inactivated by aberrant methylation of its 5' CpG island in human tumors such as colorectal cancers, gastric cancers, and acute myelogenous leukemias (Toyota et al., Cancer Res., 59(18):4535–4541 [1999]). CACNA1G maps to chromosome region 17q21 another site of frequent allele loss in human cancer. Such acquired CpG island methylation in promoter regions of cancer cells as an acquired abnormality silencing genes such as tumor suppressor genes has been described (Baylin et al., Adv. Cancer Res., 72:141–196 [1998]; and Schmutte and Jones, Biol. Chem., 379(4–5):377–388 [1998]).

Furthermore, calcium influx via voltage-gated calcium channels including T-type channels and intracellular calcium signaling plays a role in apoptosis (Berridge et al., Nature 395(6703):645–648 [1998]). In addition, platelet derived growth factor stimulated calcium influx changed during transformation of mouse C3H10T1/2 fibroblasts accompanied by a marked reduction in expression of T-type calcium channels (Estacion and Mordan, Cell Signal 9(5):363–366 [1997]). Thus, it is contemplated that the present invention will find use in investigations regarding the inactivation of voltage gated calcium channel subunits such as CACNA2D2 and CACNA1G by any of several means (e.g., in investigations pertaining to such areas as cancer pathogenesis).

The invention is further described under (A) Calcium channel types and subtypes, (B) Using probes to identify and isolate DNA encoding $\alpha_2\delta$ calcium channel peptides, (C) Using primers to amplify splice variant RNAs encoding $\alpha_2\delta$ calcium channel peptides, (D) Using nucleic acid sequences for gene therapy, (E) Generation of calcium channel $\alpha_2\delta$ subunit peptides, (F) Generation of antibodies directed to $\alpha_2\delta$ calcium channel peptides, (G) Screening compounds that modulate the activity of $\alpha_2\delta$ calcium channel peptides, (H) in vitro and in vivo suppression of tumor cell growth, and (I) Generating transgenic animals expressing reduced levels of $\alpha_2\delta$ calcium channel peptides.

A. Calcium Channel Types and Subtypes

Living cells of all biological orders are uniquely equipped with an impressive number and variety of calcium channels and pumps that are involved in maintaining calcium homeostasis within cells, tissues, and whole organisms (McEnery (Ed) J. Bioenerg. Biomembr., 30(4): 297–418 [1998]). Changes in the concentration of intracellular calcium is the central focus of many signaling networks within cells that converge to bring about changes in gene expression in response to cellular and extracellular cues to control a diverse range of cell functions (McEnery, supra; and Walker and De Waard, Trends Neurosci., 21(4):148–54 [1998]). The transduction of these stimuli results in oscillations in the intracellular concentration of calcium ions assuming the form of spikes and waves that encode signal information in their frequency and amplitude (De Koninck and Schulman, Science 279(5348):227–30 [1998]). The passage of calcium ions across the plasma membrane generating these calcium fluxes is governed by a diverse group of calcium channels encoded by separate gene families (McEnery, supra; and Walker and De Waard, supra). These calcium channels have a very wide distribution of expression throughout brain, muscle and the endocrine system, as well as other tissues (McEnery, supra; Walker and De Waard, supra; De Koninck and Schulman, supra; Gurnett et al. Neuron 16(2):431–40 [1996]; and Miller, Trends Neurosci., 20(5):189–92 [1997]).

These channels are formed by heteromultimeric complexes of $\alpha$1, $\alpha_2\delta$,$\beta$, and $\gamma$subunits. Electrophysiological and molecular cloning studies have revealed an incredible diversity of voltage-gated calcium channels. Physically, the voltage-gated calcium channels are composed of five subunits each encoded by separate distinct gene families (Walker and De Waard, supra). The major alpha 1 ($\alpha_1$) subunit which is encoded by at least 6 different genes is the pore-forming protein which interacts with other auxiliary subunits (i.e., alpha2 ($\alpha_2$), beta ($\beta$), gamma ($\gamma$), and delta ($\delta$)) to produce fully functional channels composed by unique combinations of distinct gene products. The auxiliary subunits (i.e., $\alpha_2$,$\beta$,$\gamma$ and $\delta$) with the exception of the gamma subunit significantly increase the functional expression of calcium currents. Like the alpha 1 subunit, the beta and gamma subunits are encoded by several genes; the beta subunit is encoded by 4 genes, while the gamma subunit is encoded by two genes.

The $\alpha$1 subunits contain the channel pore, voltage sensors, and the receptors for various classes of drugs and toxins (Perez-Reyes and Schneider, Kidney Int'l., 48:1111–1124 [1995]). There are three families of al subunits: the L-type (or $C_v1$ family), composed of $\alpha$1S, $\alpha$1C ($Ca_v1.2$), $\alpha$1D, and $\alpha$1F; the non-L-type high voltage-activated ($Ca_v2$) family composed of P/Q-types encoded by $\alpha$1A, the N-type is encoded by $\alpha$1B ($Ca_v2.2$), and R-types encoded by $\alpha$1E; and the T-type family ($Ca_v3$), encoded by $\alpha$1G ($Ca_v3.1$), $\alpha$1H, and $\alpha$1I. Klugbauer et al. (Klugbauer et al., supra) cloned another related $\alpha_2\delta$ subunit (i.e., a subunit that is different from the present invention), then proposed the following nomenclature: $\alpha_2\delta$-1, for the original $\alpha_2\delta$ cloned from skeletal muscle; $\alpha_2\delta$-2 for the protein described herein, and $\alpha_2\delta$-3 for their novel sequence. Similarly the genes may be referred to as CACNA2D1, CACNA2D2, and CACNA2D3, respectively (Lory et al., Hum. Genet., 100 (2):149–150 [1997]). An $\alpha_2\delta$-2 clone (KIAA0558, GenBank # AB011130, NP 006021.1) was recently independently isolated by the Kazusa DNA Research Institute from human brain as part of large scale anonymous cDNA sequencing efforts (Nagase et al., DNA Res., 5(1):31–39 [1998]).

Co-expression studies have established two physiological roles for $\beta$ subunits in high voltage-activated (HVA) $Ca^{2+}$ channels, by dramatically increasing α1 expression at the plasma membrane and altering the biophysical properties of the channel currents. In general, β subunits have little effect on the expression of low voltage-activated (LVA) currents (See, Dolphin et al., J. Physiol., 519.1:35–45 [1999]). Although only one γ and $\alpha_2\delta$ subunit have been biochemically characterized, there is recent evidence to suggest that there may be additional members of these gene families (See e.g., Letts et al., Nature Genet., 19:340–347 [1998]; Black, Mayo Clin. Proc. 74(4):357–361 [1999]; and Klugbauer et al., supra). The γ1 subunit was shown to be part of the skeletal muscle L-type channel (Sharp and Campbell, J. Biol. Chem., 264(5):2816–2825 [1989]). In addition, co-expression studies have indicated that this subunit aids in the formation of L-type channels (assayed by dihydropyridine binding (Suh-Kim et al., Recept. Channels 4(4):217–225 [1996]), and may play a role in channel inactivation (Singer et al., Science 253(5027):1553–1557 [1991]).

The $\alpha_2\delta$ subunit ($\alpha_2\delta$-1) was first identified in biochemical studies of skeletal muscle L-type $Ca^{2+}$ channels (See, Perez-Reyes and Schneider, Kidney Intl., 48:1111–1124 [1995]). Through the use of antibodies, it has also been shown to be part of the cardiac L-type and neuronal N-type channels (See, Schmid et al., Biochem., 25(12):3492–3495 [1986]; and McEnery et al., Proc. Natl. Acad. Sci. USA 88(24):11095–11099 [1991]). $\alpha_2\delta$-1 cDNA has been cloned from skeletal muscle and brain cDNA libraries (Ellis et al., Science 241(4873):1661–1664 [1988]; De Jongh et al., J. Biol. Chem., 265(25):14738–14741 [1990]; and Williams et al., Neuron 8(1):71–84 [1992]). The 175 kDa protein product is post-translationally cleaved to form disulfide-linked α2 and δ peptides, both of which are heavily glycosylated. Biochemical and mutation analysis supports a single transmembrane domain in the δ subunit that anchors the $\alpha_2\delta$ protein to the membrane (Brown and Gee, J. Biol. Chem., 273(39):25458–25468 [1998]). Co-expression of $\alpha_2\delta$-1 with both HVA and LVA α1 subunits facilitates the assembly of channels in the plasma membrane (Dolphin et al., J. Physiol., 519.1:35–45 [1999]; Suh-Kim et al., Recept. Channels 4(4):217–225 [1996]; and Burst et al., Neuropharmacol., 32(11):1089–1102 [1993]). Co-expression studies also indicate that $\alpha_2\delta$-1 can alter the pharmacological properties of L-type channels. In contrast to the δ subunits that have a dramatic effect on gating of all HVA channel in many expression systems, the effects of $\alpha_2\delta$-1 are more controversial, perhaps depending on the α1 subunit used or the expression system. For example, $\alpha_2\delta$-1 has little or no effect on either L-type (Wei et al., J. Biol. Chem., 279(45):27106–27111 [1995]; and Biel et al., FEBS Lett., 269(2):409–412 [1990]) N-type currents expressed in Xenopus oocytes (Brust et al., Neuropharmacol., 32(110):1089–1102 [1993]), but appears to affect inactivation of L-type channels expressed in mammalian cells (Shirokov et al., J. Gen. Physiol., 111(6):807–823 [1998]; and Bangalore et al., Am. J. Physiol., 270(5 Pt. 2):H1521–1528 [1996]). The opposite result occurred in studies on α1E-mediated currents, where no effect was observed in mammalian cells (Jones et al., J. Gen. Physiol., 112(2):125–143 [1998]), ) and effects on channel inactivation were observed in Xenopus oocytes (Qin et al., J. Gen. Physiol., 274(5 Pt. 1):C1324–1331 [1998]). The $\alpha_2\delta$-1 subunit has a high affinity binding site for the anti-epileptic drug gabapentin (Brown and Gee, J. Biol. Chem., 273(39):25458–25465 [1998]). Gabapentin has been shown to modestly inhibit (~30%) neuronal $Ca^{2+}$ currents, although it is unclear if this is its mechanism of action (Stefani et al., Neuropharmacol., 37(1):83–91 [1998]). Nonetheless, it is not necessary to understand the mechanisms involved with calcium channels in order to use the present invention.

Recent studies that demonstrated the association of mutations in calcium channel genes (α1 and δ genes) with inherited and acquired diseases further underlined the importance of calcium channels and have created a new field of research aimed at understanding and controlling these "channelopathies" (Miller, supra). Thus, efforts were made to obtain sequences of calcium channel subunit genes, such as the human (alpha$_2$)-subunit gene (Ellis et al., Science 241(4873):1661–4 [1988]; Williams et al., Neuron, 8(1):71–84 [1992]; Ellis et al. U.S. Pat. No. 5,686,241; and Harpold et al., U.S. Pat. No. 5,792,846), and its murine (GenBank Accession ## U73483-U73487), rat (GenBank Accession # M86621), porcine (GenBank Accession # M21948), and rabbit orthologs (GenBank Accession # AF077665). The regulatory $\alpha_2\delta$ subunit (exemplified by the sequences disclosed herein) is of special importance since it plays a dual function in both current stimulation and subunit interaction by changing microscopic channel properties (Gumett et al., supra).

B. Using Probes to Identify and Isolate DNA Encoding $\alpha_2\delta$ Calcium Channel Peptides The present invention contemplates using a portion of the nucleic acid sequences set forth as SEQ ID NOs:1, 3 and 5 as probes. As used herein, the term "probe" refers to an oligonucleotide, whether occurring naturally as in a purified restriction digest or produced synthetically, recombinantly or by PCR amplification, which is capable of hybridizing to another oligonucleotide of interest. A probe may be single-stranded or double-stranded. It is contemplated that any probe used in the present invention will be labelled with any "reporter molecule," so that it is detectable in any detection system including, but not limited to enzyme (e.g., ELISA, as well as enzyme-based histochemical assays), fluorescent, radioactive, colorimetric, gravimetric, magnetic, and luminescent systems. It is not intended that the present invention be limited to any particular detection system or label.

The probes provided herein are useful in the detection, identification and isolation of, for example, $\alpha_2\delta$ subunit sequences such as those listed as SEQ ID NOs:1, 3 and 5 as well as of homologs thereof. Preferred probes are of sufficient length (e.g., from about 9 nucleotides to about 20 nucleotides or more in length) such that high stringency hybridization may be employed.

The probes provided herein are also useful in the detection, diagnosis and typing of preneoplasias and cancers. This utility is based on the inventors' observation that genetic disruption of the 3p21.3 region (in which the $\alpha_2\delta$ gene is located) is common in cancer (e.g., lung cancer and breast cancer) and preneoplastic lesion (e.g., hyperplasia, dysplasia, carcinoma in situ). This observation was based on the inventors' results using cells which represent clones of cells that contained 3p21.3 genetic lesions (compare Wistuba et al., J. Natl. Cancer Instit., 89:1366–1377 [1997]). It is also the inventors' consideration that genetic disruption of 3p21.3 which is associated with mutation or strand break of the $\alpha_2\delta$ gene leads to reduced expression of the $\alpha_2\delta$ gene and/or inactivation of the expressed $\alpha_2\delta$ subunit peptides. Furthermore, the present invention also contemplates methylation of the promoter region to inactivate its expression.

As used herein, the term "mutation" refers to a deletion, insertion, or substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. The term "strand break" when made in reference to a double stranded nucleic acid sequence includes a single-strand break and/or a double-strand break. A single-strand break refers to an interruption in one of the two strands of the double stranded nucleic acid sequence. This is in contrast to a double-strand break which refers to an interruption in both strands of the double stranded nucleic acid sequence.

Diagnosis and detection of cancer and/or preneoplastic lesions using the invention's probes involves the use of nucleic acid probes which hybridize with $\alpha_2\delta$ nucleotide sequences that are associated with cancer and/or preneoplastic lesion. These probes are used in hybridization assays (e.g., in situ hybridization) with nucleic acid sequences from cells suspected of cancerous and/or preneoplastic. Hybridization of the nucleic acid sequences with these probes indicates that the cells are cancerous and/or preneoplastic.

C. Using Primers to Amplify Splice Variant RNAs Encoding $\alpha_2\delta$ Calcium Channel Peptides The invention also specifically contemplates using a portion of the nucleic acid sequences set forth as SEQ ID NOs:1, 3 and 5 as primers for the amplification of nucleic acid sequences by, for example, polymerase chain reactions (PCR) or reverse transcription-polymerase chain reactions (RT-PCR). Exemplary primers which are used to amplify exon sequences of the $\alpha_2\delta$ gene are illustrated in Tables 1 and 2 (Example 7, infra). The term "amplification" is defined as the production of additional copies of a nucleic acid sequence and is generally carried out using polymerase chain reaction technologies well known in the art (Dieffenbach and Dveksler, *PCR Primer, a Laboratory Manual*, Cold Spring Harbor Press, Plainview N.Y. [1995]). As used herein, the term "polymerase chain reaction" ("PCR") refers to the method of K. B. Mullis disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are the to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long (e.g., from about 9 nucleotides to about 20 nucleotides or more in length) to prime the synthesis of extension products in the presence of the inducing agent. Suitable lengths of the primers may be empirically determined and depend on factors such as temperature, source of primer and the use of the method.

The primers contemplated by the invention are useful in, for example, identifying sequences which are homologous to the $\alpha_2\delta$ sequences in humans and in other species.

D. Using Nucleic Acid Sequences for Gene Therapy

The $\alpha_2\delta$ nucleic acid sequences provided herein may be used for gene therapy applications in both non-human animals as well as in humans.

Viral vectors commonly used for in vivo or ex vivo targeting and therapy procedures are DNA-based vectors and retroviral vectors. Methods for constructing and using viral vectors are known in the art (See e.g., Miller and Rosman, BioTechn., 7:980–990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA virus, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320–330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (Stratford-Perricaudet et al., J. Clin. Invest., 90:626–630 [1992]; See also, La Salle et al., Science 259:988–990 [1993]); and a defective adeno-associated virus vector (Samulski et al., J. Virol., 61:3096–3101 [1987]; Samulski et al., J. Virol. 63:3822–3828 [1989]; and Lebkowski et al., Mol. Cell. Biol., 8:3988–3996 [1988]).

Preferably, for in vivo administration, an appropriate immunosuppressive treatment is employed in conjunction with the viral vector (e.g., adenovirus vector), to avoid immunodeactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963–967 [1992]; Wu and Wu, J. Biol. Chem., 263:14621–14624 [1988]; and Williams et al., Proc. Natl. Acad. Sci. U.S.A., 88:2726–2730 [1991]). Receptor-mediated DNA delivery approaches can also be used (Curiel et al., Hum. Gene Ther., 3:147–154 [1992]; and Wu and Wu, J. Biol. Chem., 262:4429–4432 [1987]).

For example, the nucleic acids provided herein may be introduced into cancer or preneoplastic cells using an expression vector which encodes a $\alpha_2\delta$ subunit protein using a variety of means known in the art to be useful both for delivery in vivo and ex vivo, including (1) retroviral transduction, (2) recombinant adenoviral vectors, (3) recombinant adeno-associated vectors, (4) targeted cationic liposomes, and (5) gene transfer using biolistics, as described in the following sections.

1. Retroviral Transduction

In one embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference); the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Retroviral vectors encoding $\alpha_2\delta$ subunit proteins may be used for the expression of $\alpha_2\delta$ subunit proteins in established or primary tumor cells. The transfer of $\alpha_2\delta$ genes encoding subunit proteins using retroviruses may be made more efficient by increasing the titer of the virus encoding the $\alpha_2\delta$ subunit proteins and increasing the transduction efficiency. To increase the virus titer, the retroviral construct may be designed to include a selectable marker (e.g., neo gene), and cells harboring the retroviral construct are selected by growth in the presence of a suitable selective agent (e.g., G418) followed by expansion of clones producing the highest titers of virus. To improve the transduction efficiency, retrovirus are used in combination with liposomes or poly-L-ornithine or polylysine to enhance virus uptake.

Another way to improve gene transfer efficiency using retroviruses is to increase the targeting efficiency. Many tumor cells including glioblastomas and melanomas express excess levels of the transferrin receptor. Transferrin has been used to increase the transduction efficiency of adenovirus in combination with polylysine. Several recent reports demonstrated that replacing the SU (surface) domain of the env gene of a retrovirus can increase receptor-mediated transduction efficiency. The human transferrin gene is 2097 bp long and its insertion into the SU domain of the env gene of MLV vector may not produce a stable Env product. However, since earlier studies have suggested that the modified Env fusion protein requires the native Env for stable assembly and efficient entry, co-transfection of the transferrin-env fusion gene with the native env gene may be used to produce retrovirus particles bearing a mixture of wild type and recombinant Env. The gene transfer efficiency of the new vector may be examined by transducing tumor cells expressing high levels of transferrin receptor.

2. Recombinant Adenoviral Vectors

In an alternative embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given in one alternative embodiment, within the scope of the present invention, to type 2 or type 5 human adenoviruses (Ad 2 or Ad 5), or adenoviruses of animal origin (See, WO94/26914). Those adenoviruses of animal origin that can be used within the scope of the present invention include adenoviruses of canine, bovine, murine (e.g., Mavl, Beard et al., Virol., 75–81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)). Recombinant adenoviruses can accommodate relatively large segments of foreign DNA (~7 kb), and have the advantage of a broad host cell range and high titer virus production. Adenoviruses have been used in vivo in rats to efficiently deliver genes to the liver and the pancreatic islets (reviewed in Becker et al., In *Protein Expression in Animal Cells*, Roth et al. (eds.) [1994]) and to the central nervous system (Davidson et al., Nature Genet., 3:219 [1993]). Rat livers have also been efficiently transduced ex vivo and then re-implanted (Shaked et al., Transplant., 57:1508 [1994]).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1–L5.

In a preferred embodiment, the adenoviral vector has a deletion in the E1 region (Ad 1.0). The replication defective recombinant adenoviruses are preferably employed; in some embodiments, these viruses contain a deletion of the key immediate early genes E1a and E1b. To generate and propagate recombinant viruses, a packaging cell line such as 293 cells which supply the E1a and E2a proteins in trans is employed. Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid which carries, inter alia, the DNA sequence of interest. The homologous recombination is effected following co-transfection of the adenovirus and plasmid into an appropriate cell line. The cell line that is employed should preferably (i) be transformable by the elements, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques, that are well known to one of ordinary skill in the art.

In particular, recombinant adenoviruses are created by making use of intracellular recombination between a much larger plasmid encoding most of the viral genome and a small plasmid containing the gene of interest (i.e., a gene encoding a $\alpha_2\delta$ subunit protein) flanked by regions of homology with the viral integration site. Standard methods may be used to construct the recombinant adenoviruses (Graham and Prevec, Meth. Mol. Biol., 7:109–128 [1991]; and Becker et al., supra). Briefly, each plasmid is co-transfected together with pJM17 (Microbix Systems, Toronto) into sub-confluent monolayers of 293 cells (ATCC CRL 1573) using calcium phosphate precipitation and a glycerol shock. Initial recombinant viral stocks are titered on monolayers of 293 cells, and isolated single plaques are obtained and tested for $\alpha_2\delta$ subunit protein expression using ELISA. Viral stocks are amplified and titered on 293 cells, and stored in aliquots at $-70°$ C.; if necessary, stocks are concentrated by centrifugation on density gradients. To infect tumor cells with recombinant adenoviruses, freshly isolated tumor cells are mixed with adenoviral stocks in a minimal volume. Titers of stocks are typically $10^{5-10^8}$/ml. Medium is replaced after several hours and the cells are followed for expression of the recombinant adenoviral-encoded $\alpha_2\delta$ subunit proteins and/or reporter genes.

A potential drawback of using an adenoviral delivery system is that the transduced cells may retain or express small quantities of adenoviral antigens on their surface. "Second generation" adenoviral vectors which contain deletions in the E2a gene are available and are associated with less inflammation in the recipient and a longer period of expression of the gene of interest (Engelhardt et al., Proc. Natl. Acad. Sci. USA 91:6196 [1994]). If necessary, nucleic acid sequences encoding $\alpha_2\delta$ subunit proteins are inserted into second generation adenoviral vectors.

3. Adeno-Associated Viral Vectors

In a further alternative embodiment, the vector is an adeno-associated virus (AAV) vector. The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. Nos., 5,139,941; 5,843,742; and EP 488 528; See also, Hermonat et al., Proc. Natl. Acad. Sci. USA 81:6466–6470 [1984]; Chiorini et al., J. Virol., 71:6823–6833 [1997]; and Chorini et al., J. Virol., 73:1309–1319 [1999]; each of which is incorporated by reference). These publications describe various AAV-derived constructs in which the rep and/or cap genes are deleted and replaced by a gene of interest, and the use of these constructs for transferring the gene of interest in vitro (into cultured cells) or in vivo, (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

4. Targeted Cationic Liposomes

Alternatively, the vector can be introduced in vivo by lipofection. For the past decade, there has been increasing use of liposomes for encapsulation and transfection of nucleic acids in vitro. Furthermore, synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. U.S.A., 84:7413–7417 [1987]; See also, Mackey, et al., Proc. Natl. Acad. Sci. U.S.A., 85:8027–8031 [1988]; and Ulmer et al., Science 259:1745–1748 [1993]). The use of cationic lipids may promote encapsulation of negatively charged nucleic acids, and also promote fusion with negatively charged cell membranes (Felgner and Ringold, Science 337:387–388 [1989]). Particularly useful lipid compounds and compositions for transfer of nucleic acids are described in WO95/18863 and WO96/17823, and in U.S. Pat. No. 5,459,127, herein incorporated by reference.

Cationic liposomes have proven to be a safe and effective means for inducing the transient expression of DNA in target cells [Ledley, Hum. Gene Ther., 6:1129 [1995]; Felgner, Adv. Drug Del. Rev., 5:167 [1990]; Felgner et al. Proc. Natl. Acad. Sci. USA 84:7413 [1987]; and Smith et al., Biochim. Biophys. Acta 1154:327 [1993]). Clinical trials are underway using cationic liposomes to introduce the CFTR gene into the lungs of cystic fibrosis patients (Caplen et al., Gene Ther. 1:139 [1994]; and Alton et al., Nature Genet., 5:135 [1993]) or to introduce, by direct intra-tumor injection, the T cell costimulator B7-1 into malignant melanoma lesions in order to induce a cell-mediated immune response (Nabel et al., Proc. Natl. Acad. Sci. USA 90:11307 [1993]).

Cationic liposomes (e.g., DOTAP/DOPE) and ligand-targeted cationic liposomes may be employed for the delivery of $\alpha_2\delta$ subunit proteins to tumor cells. Ligand-targeted liposomes are made by covalently attaching ligands or antibodies to the surface of the cationic liposome. For example, when glioblastoma cells are to be targeted, transferrin is used as the ligand as glioblastoma cells express high levels of the transferrin receptor on their surface. When melanoma cells are to be targeted, internalizing receptors, monoclonal antibodies directed against melanoma-specific surface antigens (e.g., mAb HMSA5) may be employed as the ligand.

Plasmid DNA encoding $\alpha_2\delta$ subunit proteins is formed into a complex with preformed cationic liposomes using standard methodology or alternatively the DNA is encapsulated into the liposome interior. The DNA-containing liposomes are then used to transfer the DNA to tumor cells in vivo by direct intra-tumor injection or in vitro (using freshly explanted tumor cells) followed by return of the transduced cells to the recipient (e.g., a human patient or non-human animal).

5. Gene Transfer Using Biolistics

Biolistics (microballistics) is a method of delivering DNA into cells by projection of DNA-coated particles into cells or tissues. DNA is coated onto the surface of gold or tungsten microparticles (~1–3 $\mu$m diameter) and these particles are accelerated to high velocity and are impacted onto the target cells. The particles burst through the cell membrane and lodge within the target cell. The cell membrane quickly reseals and the passenger DNA elutes off of the particle and is expressed. The biolistic method has been used to transfect mammalian cells (Williams et al., Proc. Natl. Acad. Sci. USA 88:2726 [1991]; Tang et al., Nature 356:152 [1992]; and Sanford et al., Meth. Enzymol., 217:483 [1993]).

A hand-held biolistic apparatus (BioRad) is used to transfer DNA into tumor cells or isolated tumor fragments. This device uses compressed helium to drive a disc-shaped macroprojectile which carries on its surface microparticles (1–5 $\mu$m) of gold which have been coated with purified plasmid DNA (coprecipitated with spermine) (Williams et al., supra). This apparatus has been used to successfully transfect primary tissues.

Plasmid DNA encoding the $\alpha_2\delta$ subunit proteins may be coated onto the surface of gold microparticles according to the manufacturer's instructions (BioRad) and the biolistic apparatus is used to transfer the DNA into freshly explanted tumor cells or directly into exposed tumors (e.g., metastatic nodules on the surface of the liver, melanoma lesions on the skin).

Regardless of the method of delivery of the expression vector into a cell, it is preferred, though not required, that the expression vector contain a selection marker (e.g., neo gene) to facilitate selection of transfected cells. Transfected cells are selected by growth in the presence of G418 (e.g., 200 $\mu$g/ml), followed by culture in growth medium containing reduced concentrations of G418 (e.g., 100 $\mu$g/ml) and growth to confluence. Expression of the $\alpha_2\delta$ subunit protein is evaluated using, for example, immunoblot analysis or flow cytometry using monoclonal antibodies which are specific for the $\alpha_2\delta$ subunit protein. It is preferred, though not necessary, that expression of the $\alpha_2\delta$ subunit protein in the transfected tumor cells is both constitutive and stable. Constitutive expression refers to expression in the absence of a triggering event or condition, and can be achieved by the selection of a promoter which drives expression of the nucleic acid sequence encoding the $\alpha_2\delta$ subunit protein. Examples of promoters which drive constitutive expression of a structural nucleic acid sequence which is operably linked to the promoter include the SR$\alpha$ promoter, CMV promoter, and HIV promoter.

Regardless of the type of expression vector used for delivery of the $\alpha_2\delta$ nucleic acid sequences into a cell, the expression vector may be introduced to the cell by direct injection into tumor and/or preneoplastic tissue, systemic (e.g., intravenous) administration, aerosol administration (e.g., for delivery to the bronchial tree and other lung tissues), injection into breast ducts (e.g., for delivery to breast tissue), topical administration (e.g., for delivery to cervical tissue). It is expected that the $\alpha_2\delta$ nucleic acids of the invention would function as a tumor suppressor. Tumor suppressor function may be determined by (for example) reduction in the size of tumors which are detectable at the time of administration of the expression vectors containing $\alpha_2\delta$ nucleic acid sequences as compared to the size of the tumors prior to such administration. Alternatively, where the expression vectors containing $\alpha_2\delta$ nucleic acid sequences are introduced to preneoplastic cells, tumor suppressor function may be determined by lack of progression of the preneoplastic cells to cancer cells over time.

E. Generation of Calcium Channel $\alpha_2\delta$ Subunit Peptides

The present invention provides the polypeptide sequences of isoform I (SEQ ID NOs:2 and 4) and isoform II (SEQ ID NO:6) of the human calcium channel $\alpha_2\delta$ subunit and specifically contemplates portions and variants thereof. For example, $\alpha_2\delta$ subunit variants included within the scope of this invention include $\alpha_2\delta$ subunit polypeptide sequences containing deletions, insertions or substitutions of amino acid residues which result in a polypeptide that is functionally equivalent to the $\alpha_2\delta$ subunit polypeptide isoforms. By the term "functionally equivalent to the $\alpha_2\delta$ subunit polypeptide isoforms" is meant that a polypeptide is capable of associating with at least an $\alpha_1$ subunit (preferably with $\alpha_1$ and $\beta$ subunits, and more preferably with $\alpha_1,\beta$ and $\gamma$ subunits) to produce a functional calcium channel. For example, amino acids may be substituted for other amino acids having similar characteristics of polarity, charge, solubility, hydrophobicity, hydrophilicity and/or amphipathic nature. Alternatively, substitution of amino acids with other amino acids having one or more different characteristic may be desirable for the purpose of producing a polypeptide which is secreted from the cell in order to, for example, simplify purification of the polypeptide.

The $\alpha_2\delta$ subunit isoform I and II polypeptide sequences and their functional variants may be made using chemical synthesis. For example, peptide synthesis of the $\alpha_2\delta$ subunit polypeptide, in whole or in part, can be performed using solid-phase techniques well known in the art. Synthesized polypeptides can be substantially purified by high performance liquid chromatography (HPLC) techniques, and the composition of the purified polypeptide confirmed by amino acid sequencing. One skilled in the art would recognize that variants of the $\alpha_2\delta$ subunit isoform I and II polypeptides can be produced by manipulating the polypeptide sequence during and/or after its synthesis.

The $\alpha_2\delta$ subunit and its functional variants can also be produced by an expression system. Expression of $\alpha_2\delta$ subunit isoform I and II polypeptides may be accomplished by inserting nucleotide sequences which encode these polypeptides (or variants, portions, or homologs of the nucleotide sequences) into appropriate vectors to create expression vectors, and transfecting the expression vectors into host cells. The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. Expression in insect cells (e.g., *Spodoptera*) using insect vectors (e.g., baculovirus) is also contemplated to be within the scope of the invention.

The scope of this invention further encompasses amino acid sequences of the $\alpha_2\delta$ polypeptides ligated to one or more amino acid sequences as part of a fusion protein. Such fusion proteins may be desirable, for example, to detect expression of the $\alpha_2\delta$ polypeptides. Examples of amino acid sequences which may be used as fusion partners include β-galactosidase, luciferase, green fluorescent protein, Myc protein tags, FLAG tags, and chloramphenicol acetyltransferase. Fusion proteins may also be desirable to facilitate purification of the expressed $\alpha_2\delta$ polypeptides. For example, the heterologous sequence of protein A allows purification of the fusion protein on immobilized immunoglobulin. Other affinity traps are well known in the art and can be utilized to advantage in purifying the expressed fusion protein. For example, pGEX vectors (Promega, Madison Wis.) may be used to express the $\alpha_2\delta$ polypeptides as a fusion protein with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

While the invention discloses cloning of the sequences of the invention in the CMV expression vector pcDNA3.1 His C (Invitrogen), the adenovirus shuttle vector pLJ17 (pAdE1/CMV), and the retrovirus tetracycline regulatable vectors pRev-TRE vector (Clontech) (Example 8), and in the pETE vector (Example 9), other expression vectors are expressly contemplated to be within the scope of the invention. Expression vectors are exemplified by plasmids, recombinant bacteriophage, cosmid DNA vectors, viruses and the like. Expression vectors can be constructed using techniques well known in the art (Sambrook et al., *Molecular Cloning, A Laboratory Manual*, Cold Spring Harbor Press, Plainview N.Y. [1989]; and Ausubel et al., *Current Protocols in Molecular Biology*, John Wiley & Sons, New York N.Y. [1989]). Briefly, the nucleic acid sequence of interest is placed in operable combination with transcription and translation regulatory sequences. The term "in operable combination" as used herein refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. Regulatory sequences include initiation signals such as start (i.e., ATG) and stop codons, promoters which may be constitutive (i.e., continuously active) or inducible, as well as enhancers to increase the efficiency of expression, and transcription termination signals. Transcription termination signals must be provided downstream from the structural gene if the termination signals of the structural gene are not included in the expression vector. Expression vectors may become integrated into the genome of the host cell into which they are introduced, or are present as unintegrated episomal vectors. Typically, unintegrated nonepisomal vectors are transiently expressed and regulated for several hours (e.g., 72 hours) after transfection.

The choice of promoter is governed by the type of host cell to be transfected with the expression vector. Host cells include, but are not limited to eukaryotic cells, prokaryotic cells, insect cells, etc. In one embodiment the cell is eukaryotic. In a more preferred embodiment, the eukaryotic cell is a cancer cell. Other eukaryotic cells are expressly contemplated (e.g., COS cells, mouse L cells, Chinese hamster ovary cells, human embryonic kidney cells, and African green monkey cells). In an alternative preferred embodiment, the eukaryotic cell is an amphibian oocyte. In a more preferred embodiment, the amphibian oocyte is a frog oocyte.

Transfected cells may be identified by any of a number of marker genes. These include antibiotic (e.g., neomycin, puromycin, hygromycin for eukaryotic cells, and gentamicin, penicillin, and kanamycin for prokaryotic cells) resistance genes as well as marker or reporter genes (e.g., β-galactosidase, luciferase, green fluorescent protein, and Myc protein tags) which catalyze the synthesis of a visible reaction product.

Vectors may be introduced into a host cell using a number of standard and routine methods known to those skilled in the art (See e.g., Sambrook, et al., supra) including, but not limited to, microinjection, DEAE-dextran, calcium phosphate co-precipitation, cell fusion, electroporation, biolistics, lipofection, DNA viruses, and RNA viruses, or retrovirus-mediated transduction.

Expression of the $\alpha_2\delta$ nucleic acid sequences provided herein by transfected cells may be detected either indirectly using reporter genes, or directly by detecting mRNA or protein encoded by the $\alpha_2\delta$ nucleic acid sequences. Indirect detection of expression may be achieved by placing a reporter gene in tandem with the nucleic acid sequence encoding $\alpha_2\delta$ subunits under the control of a single promoter. Expression of the reporter gene indicates expression of the tandem $\alpha_2\delta$ subunit nucleic acid sequence. It is preferred that the reporter gene either have a visible reaction product or have a "tag" which may be detected by antibodies to give such a product. For example, cells expressing the reporter gene β-galactosidase produce a blue color when grown in the presence of X-Gal; cells grown in medium containing luciferin will fluoresce when expressing the reporter gene luciferase; cells containing green fluorescent protein spontaneously fluoresce when exposed to appropriate light wavelengths; cells expressing Myc, FLAG or His tags are detectable using commercially available anti-Myc, anti-FLAG or anti-His antibodies which are themselves coupled to a reporter molecule (e.g., enzyme or fluorescent compound).

Direct detection of expression of $\alpha_2\delta$ polypeptides can be achieved using methods well known to those skilled in the art. For example, mRNA isolated from transfected cells can be hybridized to labelled oligonucleotide probes and the hybridization detected. Alternatively, polyclonal or monoclonal antibodies specific for $\alpha_2\delta$ polypeptides can be used to detect expression of the recombinant $\alpha_2\delta$ polypeptide using enzyme-linked immunosorbent assay (ELISA), radio-immunoassay (RIA), fluorescent activated cell sorting (FACS) and immunohistochemical assays (e.g., enzyme-linked and fluorescent assays). Those skilled in the art recognize that, for example, immunohistochemical assays are useful in diagnostic test to identify individual cells which express $\alpha_2\delta$ polypeptides.

Recombinant $\alpha_2\delta$ polypeptides and their variants which are expressed by the host cell can be purified either from the culture medium, if the expression construct directs secretion into culture medium, or from the host cell lysate using purification techniques known in the art. For example, $\alpha_2\delta$ polypeptides may be expressed as a fusion protein with heterologous metal chelating peptides (i.e., polyhistidine tracts) or with protein A domains, and purified on commercially available immobilized metals or immunoglobulins, respectively.

The polypeptides of the invention are also useful in treating patients with Lambert-Eton myasthenic syndrome (LES). LES is an autoimmune disease characterized by an insufficient release of acetylcholine from motor nerve terminals which normally are responsive to nerve impulses. Immunoglobulins (IgG) from LES patients block voltage-dependent calcium channels and thus inhibit calcium channel activity. Treatment of LES patients may be achieved by using a recombinant $\alpha_2\delta$ protein to clear patients' blood of the damaging autoantibodies.

The polypeptides of the invention are additionally useful for reconstituting a fully functional channel (e.g., on the cell membrane of frog eggs) by, for example, introducing into a cell expression vectors which encode the α1 subunit [Harpold et al. supra] as well as the $\alpha_2\delta$ subunits of the invention, and optionally the β-subunit and/or γ-subunit (Harpold et al., supra).

Additionally, those skilled in the art recognize that the $\alpha_2\delta$ subunit polypeptide sequences of the present invention are useful in generating antibodies as further described below.

F. Generation of Antibodies Directed to Calcium Channel $\alpha_2\delta$ Peptides Antibodies (polyclonal and monoclonal) which are specific for at least a portion of the $\alpha_2\delta$ subunit isotype I and II provided herein may be generated using methods known in the art (see Example 8). The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells. The terms "specific binding," "specifically binding" and grammatical equivalents thereof when used in reference to the interaction of an antibody and a protein or peptide mean that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

Those skilled in the art know how to make polyclonal and monoclonal antibodies which are specific to a desirable polypeptide. These include but are not limited to the hybridoma technique originally developed by Köhler and Milstein (Kohler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]). For example, as described further below, monoclonal antibodies may be generated by immunizing an animal (e.g., mouse, rabbit, etc.) with a desired antigen and the spleen cells from the immunized animal are immortalized, commonly by fusion with a myeloma cell. Furthermore, the present invention encompasses antibodies produced using genetic immunization (e.g., immunization of an animal with a recombinant construct that provokes an immune response against the construct by the animal).

In an additional embodiment of the invention, monoclonal antibodies can be produced in germ-free animals utilizing relatively recent technology (See e.g., PCT/US90/02545). Also according to the invention, human antibodies may be used and can be obtained by using human hybridomas (Cote et al., Proc. Natl. Acad. Sci. U.S.A.80:2026–2030 [1983]).

According to the invention, techniques described for the production of single chain antibodies (U.S. Pat. No. 4,946,778; herein incorporated by reference) can be adapted to produce $\alpha_2\delta$ single chain antibodies. An additional embodiment of the invention utilizes the techniques described for the construction of Fab expression libraries (Huse et al, Science 246:1275–1281 [1989]) to allow rapid and easy identification of monoclonal Fab fragments with the desired specificity for $\alpha_2\delta$.

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

For monoclonal antibody production, immunization with antigen may be accomplished in the presence or absence of an adjuvant (e.g., Freund's adjuvant). Typically, for a mouse, 10 $\mu$g antigen in 50–200 $\mu$l adjuvant or aqueous solution is administered per mouse by subcutaneous, intraperitoneal or intramuscular routes. Booster immunization may be given at intervals, e.g., 2–8 weeks. The final boost is given approximately 2–4 days prior to fusion and is generally given in aqueous form rather than in adjuvant.

Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400×g for 5 min.), washed and counted. Spleen cells are fused with myeloma cells to generate hybridoma cell lines. Several mouse myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10–15% fetal calf serum. Fusion of myeloma cells and spleen cells may be accomplished using polyethylene glycol (PEG) or by electrofusion using protocols which are routine in the art. Fused cells are distributed into 96-well plates followed by selection of fused cells by culture for 1–2 weeks in 0.1 ml DMEM containing 10–15% fetal calf serum and HAT. The supernatants are screened for antibody production using methods well known in the art. Hybridoma clones from wells containing cells which produce antibody are obtained (e.g., by limiting dilution). Cloned hybridoma cells (4–5×10$^6$) are implanted intraperitoneally in recipient mice, preferably of a BALB/c genetic background. Sera and ascites fluids are collected from mice after 10–14 days.

The invention also contemplates humanized antibodies which are specific for at least a portion of the $\alpha_2\delta$ subunit isotype I and II provided herein. Humanized antibodies may be generated using methods known in the art, such as those described in U.S. Pat. Nos. 5,545,806; 5,569,825 and 5,625,126, the entire contents of each of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

The antibodies of the invention which are directed against $\alpha_2\delta$ polypeptides may be used for the detection of expression of the $\alpha_2\delta$ proteins in cells. This may be desirable to, for example, use changes in the levels of expression of the cell's $\alpha_2\delta$ subunit proteins as a prognostic marker for the development of disease (e.g., cancer, neurological, autoimmune, and cardiovascular diseases) as well as for monitoring the efficacy of compounds in the prevention and treatment of these diseases. Thus, antibodies specific for $\alpha_2\delta$ polypeptides may be used to identify cells in clinically relevant samples from patients who have lost expression of the $\alpha_2\delta$ polypeptides.

Additionally, the antibodies provided herein may be used in the detection, diagnosis and typing of preneoplasias and cancers. For example, differences in the level of expression of the $\alpha_2\delta$ gene in preneoplastic and cancer cells as compared to normal cells may be used to detect and diagnose the presence of preneoplastic and cancer cells as well as to type such cells using methods known in the art, e.g., immunohistochemical assays including, but not limited to, enzyme-linked and fluorescent assays.

In the production of antibodies, screening for the desired antibody can be accomplished by techniques known in the art (e.g., radioimmunoassay, ELISA [enzyme-linked immunosorbant assay], "sandwich" immunoassays, immunoradiometric assays, gel diffusion precipitin reactions, immunodiffusion assays, in situ immunoassays [using colloidal gold, enzyme or radioisotope labels, for example], Western Blots, precipitation reactions, agglutination assays (e.g., gel agglutination assays, hemagglutination assays, etc.), complement fixation assays, immunofluorescence assays, protein A assays, and immunoelectrophoresis assays, etc. In addition, it is contemplated that phage display technology as known in the art will find use in conjunction with the present invention to detect the CACNA2D2 subunit in samples of interest.

G. Screening Compounds That Modulate the Activity of $\alpha_2\delta$ Calcium Channel Peptides The invention provides methods for identifying compounds (e.g., calcium channel agonists and antagonists) that modulate the activity of calcium channels. These methods involve contacting cells which have been transfected with an expression vector that contains $\alpha_2\delta$ nucleic acid sequences provided herein, and which express $\alpha_2\delta$ polypeptides, with a test compound as well as with a calcium channel selective ion (e.g., calcium ion, barium ion, etc.). This is followed by measuring the ability of the compound to alter the activity of the calcium channel in the transfected cell which expresses the heterologous $\alpha_2\delta$ polypeptides as compared to that in a control cell which does not express the heterologous $\alpha_2\delta$ polypeptides. The cell is maintained in a solution having a concentration of calcium channel selective ions which is sufficient to provide an inward current when the channels open. Methods which are similar to those of the instant invention but which utilize calcium channel subunits other than the invention's $\alpha_2\delta$ subunit are known in the art such as those described by Ellis et al., U.S. Pat. No. 5,407,820; Harpold et al., U.S. Pat. No. 5,429,921; and Harpold et al., U.S. Pat. No. 5,792,846, the entire contents of each of which are incorporated by reference.

The activity of the calcium channel is determined by measuring the magnitude and duration of the inward current caused by flow of calcium channel selective ions. The amount of current which flows through the recombinant calcium channel of the cell may be determined directly (e.g., physiologically) as described, for example, by Harpold et al., U.S. Pat. No. 5,792,846. Alternatively, the amount of current may be determined indirectly by monitoring an independent reaction which occurs intracellularly and which is directly influenced in a calcium (or other) ion dependent manner. For example, the cell expresses a heterologous $\alpha_2\delta$ subunit and also contains a transcriptional control element which is responsive to a calcium channel selective ion and which is operatively linked to a structural gene that encodes an indicator protein.

The assays of the invention may be used in conjunction with methods of rational drug design to select among compounds that modulate the activity of calcium channels. Such compounds may then be tested for their activity in the treatment of channelopathies (e.g., migraine, epilepsy, and episodic ataxia, cardiovascular diseases, LES, cancer, etc.) in model animals as well as human subjects.

H. In Vitro and In Vivo Suppression of Tumor Cell Growth

The function of the invention's $\alpha_2\delta$ nucleic acid sequences, portions and homologs thereof in suppression of tumor cell growth in vitro and in vivo may be ascertained using the following guidelines. The nucleic acid sequence of interest is cloned into a vector to generate an expression vector as described supra. The expression vectors are transfected into cancer cells which are then used for the determination of the effect of expression of the nucleic acid sequence of interest on cell growth both in vitro and in vivo. The cancer cells into which the expression vectors are transfected may be engineered to express only a heterologous functional $\alpha_2\delta$ subunit. This may be desirable where, for example, the transfected cancer cell expresses functional endogenous calcium channel subunits but lacks expression of a functional endogenous $\alpha_2\delta$ subunit. Alternatively, the cancer cells into which the expression vectors are transfected may be engineered to express $\alpha_2\delta$ subunits as well as calcium channel subunits other than the $\alpha_2\delta$ subunit, such as the human calcium channel alpha 1, beta, and gamma subunits disclosed in the art (Ellis et al. [1988] supra; Williams et al. [1992] supra; Ellis et al. U.S. Pat. No. 5,686,241; and Harpold et al., U.S. Pat. No. 5,792,846).

For example, transfected tumor cells which express the $\alpha_2\delta$ nucleic acid sequence as well as control cells (i.e., corresponding tumor cells which have not been transfected with the expression vector) are cultured in vitro under conditions which result in growth of the control cells as determined by, for example, an increase in cell number over a period of time. Growth of the control and transfected cells is then compared. Detection of a growth level which is statistically lower in the transfected cells as compared to the control cells indicates that the nucleic acid sequence of interest functions as a tumor suppressor.

It is also contemplated that the present invention encompass methods that include the measurement of apoptosis (i.e., programmed cell death) either by itself or after other treatment (e.g., drugs). An increase in apoptosis could be viewed as a consequence of a normal function of the calcium channel gene product under certain conditions.

The tumor suppressor function of the sequence of interest may also be determined in vivo. This may be accomplished by introducing (e.g., by injection) transfected and control tumor cells into a host animal (e.g., mouse, etc.) and observing the growth of the introduced tumor cells as determined, for example, by the number of tumors, time at which tumors are first detected, and/or change in the diameter of a tumor over a period of time. One of skill in the art knows that immunological rejection of the tumor cells by the host animal is undesirable and may be avoided by, for example, introducing tumor cells which are derived from one species into a host of the same species (e.g., mouse tumor cells into a mouse host). Alternatively, tumor cells from one species may be introduced into an immunocompromised host animal of another species (e.g., human tumor cells into a nude (nu/nu) SCID mouse host). Detection of a growth level which is statistically lower in the transfected tumor cells as compared to the control tumor cells indicates that the nucleic acid sequence of interest functions as a tumor suppressor. Other measurements can also be used to assess the efficacy of treatment, including but not limited to determining whether there is a decrease in metastatic behavior of the tumor, an increase in apoptosis, a decrease in tumor angiogenesis, the complete absence of tumors, an increase in animal survival, and/or an increase in cure rates of animals.

I. Generating Transgenic Animals Expressing Reduced Levels of $\alpha_2\delta$ Calcium Channel Peptides In addition to animals which express increased levels of calcium channel $\alpha_2\delta$ polypeptides relative to a corresponding wild-type animal, the present invention provides transgenic non-human animals which express reduced levels of calcium channel $\alpha_2\delta$ polypeptides relative to a corresponding wild-type animal. The present invention also provides transgenic non-human animals which express reduced activity of calcium channel $\alpha_2\delta$ polypeptides relative to a corresponding wild-type animal.

The transgenic animals of the present invention are generated by introducing a targeting vector into a host cell. It is contemplated that the targeting vector contains the $\alpha_2\delta$ subunit nucleic acid sequences disclosed herein (e.g., SEQ ID NOs:1, 3, and 5). Additionally, the targeting vector may contain the $\alpha_2\delta$ subunit nucleic acid sequences which have been modified by, for example, an insertion, deletion, or substitution of one or more nucleotide sequences into the $\alpha_2\delta$ subunit nucleic acid sequence.

A. Transgenic Animal Production In General

For example, the present invention provides a method for gene recombination in post-mitotic cells, comprising: providing a gene transfer system comprising a DNA sequence encoding a Cre recombinase and post-mitotic target tissue comprising target nucleic acid, wherein the target nucleic acid comprises one or more site-specific recombination target sequences; and introducing the gene transfer system to the target tissue, whereby recombination occurs at the one or more site-specific recombination target sequences. In one embodiment of the present invention, the DNA sequence encoding a Cre recombinase further comprises a tissue-specific promoter sequence.

In some preferred embodiments, the gene transfer system comprises a viral gene transfer system. In particularly preferred embodiments, the viral gene transfer system comprises an adenoviral gene transfer system.

In certain embodiments of the present invention, the post-mitotic target tissue comprises cardiac, skeletal muscle, brain, lung testis, pancreas, small intestine, ovary, spleen, or kidney, although the methods of the present invention are applicable to any post-mitotic target tissue. In other embodiments, the target nucleic acid comprises a gene. In yet other embodiments, the one or more site-specific recombination target sequences comprises one or more loxP target sequences, although other site-specific recombination target sequences are contemplated by the present invention, including, but not limited to, loxP2, loxP3, loxP23, loxP511, loxB, loxC2, loxL, loxR, loxΔ86, loxΔ117, frt, dif, flp, and att target sequences.

In certain embodiments of the present invention, the introducing of the gene transfer system to the target tissue, comprises injecting the gene transfer system into the target tissue.

The present invention further provides a method for gene recombination in a tissue of interest (e.g., cardiac, skeletal muscle, brain, lung testis, pancreas, small intestine, ovary, spleen, or kidney), comprising: providing a viral gene transfer system comprising a DNA sequence encoding a Cre recombinase and a tissue of interest comprising target nucleic acid, wherein the target nucleic acid comprises one or more site-specific recombination target sequences; and introducing the viral gene transfer system to the tissue of interest, whereby recombination occurs at the one or more site-specific recombination target sequences. In some embodiments of the present invention, the tissue of interest comprises post-mitotic cardiac tissue. In other embodiments, the DNA sequence encoding a Cre recombinase further comprises a tissue-specific promoter sequence. In yet other embodiments, the introducing of the viral gene transfer system to the tissue of interest, comprises injecting the viral gene transfer system into the tissue.

The present invention further provides a method for tissue-restricted gene recombination, comprising: providing a viral gene transfer system comprising a DNA sequence encoding a Cre recombinase and a tissue-specific promoter sequence and post-mitotic cardiac tissue comprising target nucleic acid, wherein the target nucleic acid comprises one or more site-specific recombination target sequences; and introducing the viral gene transfer system to the post-mitotic tissue, whereby recombination occurs at the one or more site-specific recombination target sequences. In some embodiments, the introducing of the viral gene transfer system to the post-mitotic cardiac tissue comprises injecting the viral gene transfer system into the post-mitotic tissue. In certain embodiments, the tissue-specific promoter sequence comprises an α-myosin heavy chain promoter sequence.

The present invention further provides a non-human mammal, wherein one or more tissues of the non-human mammal comprise tissue prepared according to the methods described above. In preferred embodiments, the non-human mammal is selected from the order Rodentia. In particularly preferred embodiments, the non-human mammal is selected from the group consisting of mice and rats.

The present invention further provides a non-human mammal having post-mitotic tissue comprising an altered genotype as compared to wild-type post-mitotic tissue, wherein the altered genotype is the result of tissue-specific recombination. In preferred embodiments the post-mitotic tissue comprises cardiac, skeletal muscle, brain, lung testis, pancreas, small intestine, ovary, spleen, or kidney tissue, although the present invention contemplates all other post-mitotic tissues. In some embodiments, the altered genotype comprises a gene knockout.

In addition, the present invention provides a method for screening compounds for their effect on a transgenic animal, comprising: providing a transgenic animal, wherein the transgenic animal is the non-human mammal described above and a composition comprising a test compound in a form suitable for administration to the non-human mammal; and administering the test compound to the non-human mammal. In some embodiments, the method further comprises the step of detecting a response of the non-human mammal to the test compound.

B. Transgenic Knockout Animals

This section provides descriptions of various means to produce transgenic knockout animals of the present invention. The transgenic $\alpha_2\delta$-knockout ($\alpha_2\delta$-KO) animals of the present invention may be produced by a variety of means. Where the transgenic animal is a mouse, any targeting vector containing at least a portion of $\alpha_2\delta$ nucleic acid sequences of the invention which is capable of homologously recombining into the mouse $\alpha_2\delta$ subunit gene in a manner that disrupts the mouse $\alpha_2\delta$ gene (e.g., deletion, introduction of a frameshift, premature stop codon, missense mutation, etc.) may be employed. The targeting vector may be of the replacement- or insertion-type. Replacement-type vectors contain two regions of homology with the targeted gene flanking a selectable marker and result in the insertion of the selectable marker which thereby disrupts the targeted gene. Insertion-type vectors contain a single region of homology with the targeted gene and result in the insertion of the entire targeting vector into the targeted gene.

Positive selection markers include, but are not limited to, the neo gene, the hyg gene and gpt gene, may also be used so long as the selection marker permits detection of the disruption of the wild-type $\alpha_2\delta$ subunit gene with the vector sequence. Negative selectable markers are exemplified by the dt gene, and the HSV-tk gene.

It is not necessary that the targeting vector contain a selectable marker gene as discussed above, although the use of a selectable marker is preferred. Further, it is not necessary that, if a selectable marker is employed, the targeting vector employ both a positive (e.g., neo) and a negative (e.g., dt) selectable marker gene.

The targeting vector may be introduced into a variety of host cells, e.g., oocytes, zygotes and embryonic stem (ES) cells. In a preferred embodiment, the host cell is an embryonal stem (ES) cell. Another method of introducing the vector into the animal's germ line involves using embryonic stem (ES) cells as recipients of the expression vector. ES cells are pluripotent cells directly derived from the inner cell mass of blastocysts. Vectors can be introduced into ES cells using any method which is suitable for gene transfer into cells (e.g., by transfection, cell fusion, electroporation, microinjection, DNA viruses, and RNA viruses). Once the expression vector has been introduced into an ES cell, the modified ES cell is then introduced back into the embryonic environment for expression and subsequent transmission to progeny animals. The most commonly used method is the injection of several ES cells into the blastocoel cavity of intact blastocysts. Alternatively, a clump of ES cells may be sandwiched between two eight-cell embryos. Both methods result in germ line transmission at high frequency.

Transgenes may also be introduced into ES cells by retrovirus-mediated transduction or by micro-injection. Transfected ES cells which contain the transgene may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

Transfected ES cells can thereafter colonize an embryo following their introduction into the blastocoel of a blastocyst-stage embryo and contribute to the germ line of the resulting chimeric animal.

The generation of transgenic $\alpha_2\delta$-KO mice need not employ ES cells. For example, embryonal cells at various developmental stages can be used to introduce transgenes for the production of transgenic animals. Different methods are used depending on the stage of development of the embryonal cell. The zygote is the best target for microinjection. In the mouse, the male pronucleus reaches the size of approximately 20 micrometers in diameter which allows reproducible injection of 1–2 picoliters (p1) of DNA solution. The use of zygotes as a target for gene transfer has a major advantage in that in most cases the injected DNA will be incorporated into the host genome before the first cleavage. As a consequence, all cells of the transgenic non-human animal will carry the incorporated transgene. This will, in general, also be reflected in the efficient transmission of the transgene to offspring of the founder since 50% of the germ cells will harbor the transgene. Micro-injection of zygotes is the preferred method for incorporating transgenes in practicing the invention.

Alternatively, targeting vectors or transgenes may be microinjected into mouse oocytes to generate mice containing a disrupted $\alpha_2\delta$ subunit gene. PCR can be employed to screen the targeted cells to identify cells containing a disrupted $\alpha_2\delta$ gene without the need to use a selectable marker and to subject the targeted cells to growth in selective medium. In addition, chimeric RNA-DNA oligonucleotides containing modified RNA residues (2'-O-methyl modification of the ribose) can be used to target mutations (e.g., the introduction of a frameshift, premature stop codon, etc.) into the $\alpha_2\delta$ gene using ES cells or oocytes to create transgenic $\alpha_2\delta$-KO mice.

Once the expression vector has been injected into the fertilized egg cell, the cell is implanted into the uterus of a pseudopregnant female and allowed to develop into an animal. Heterozygous and homozygous animals can then be produced by interbreeding founder transgenics. This method has been successful in producing transgenic mice, sheep, pigs, rabbits and cattle.

Retroviral infection can also be used to introduce transgenes into a non-human animal. The developing non-human embryo can be cultured in vitro to the blastocyst stage. During this time, the blastomeres can be targets for retroviral infection. Efficient infection of the blastomeres is obtained by enzymatic treatment to remove the zona pellucida. The viral vector system used to introduce the transgene is typically a replication-defective retrovirus carrying the transgene. Transfection is easily and efficiently obtained by culturing the blastomeres on a monolayer of virus-producing cells.

Alternatively, infection can be performed at a later stage. Virus or virus-producing cells can be injected into the blastocoele. Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo. Additional means of using retroviruses or retroviral vectors to create transgenic animals known to the art involves the micro-injection of retroviral particles or mitomycin C-treated cells producing retrovirus into the perivitelline space of fertilized eggs or early embryos.

A transgenic animal of the invention which "expresses a reduced level of calcium channel $\alpha_2\delta$ subunit relative to a corresponding wild-type animal" is a transgenic animal which contains a quantity of at least one isoform of $\alpha_2\delta$ subunit that is less than, preferably 50% less than, and more preferably 90% less than, the quantity of a corresponding isoform of $\alpha_2\delta$ subunit in an isogeneic animal which contains a wild-type $\alpha_2\delta$ gene. Most preferably, the transgenic animals of the invention contain a quantity of at least one isoform of $\alpha_2\delta$ subunit which is at the background level of, or is undetectable by, an Enzyme Linked Immunosorbent Assay (ELISA).

A transgenic animal of the invention which "expresses a reduced activity of calcium channel $\alpha_2\delta$ subunit relative to a corresponding wild-type animal" is a transgenic animal which contains at least one isoform of $\alpha_2\delta$ subunit that exhibits less than, preferably 50% less than, and more preferably 90% less than, the biological activity of a corresponding isoform of $\alpha_2\delta$ subunit in an isogeneic animal which contains a wild-type $\alpha_2\delta$ gene. The biological activity of $\alpha_2\delta$ subunit may be determined by methods known in the art (e.g., oocyte injection assay disclosed by Ellis et al., U.S. Pat. No. 5,407,820; Harpold et al., U.S. Pat. No. 5,429,921; and Harpold et al., U.S. Pat. No. 5,792,846, the contents of each of which are incorporated by reference). Most preferably, the transgenic animals of the invention contain at least one isoform of $\alpha_2\delta$ subunit whose activity is undetectable by an oocyte injection assay.

The transgenic $\alpha_2\delta$-KO animals provided by the present invention find several uses. For example, these animals (including heterozygous ($\alpha_2\delta$+/−) mice which contain only one copy of the gene, as well as homozygous ($\alpha_2\delta$−/−) mice which lack both copies of the gene) may be used as murine models of cancer (e.g., lung cancer, breast cancer, etc.), human neurological diseases (e.g., epilepsy, migraine, episodic ataxia, etc.), human cardiovascular diseases (e.g., cardiac arrhythmia, angina pectoris, etc.), and human autoimmune disease (e.g., LES).

EXPERIMENTAL

The following examples serve to illustrate certain preferred embodiments and aspects of the present invention and are not to be construed as limiting the scope thereof. Unless otherwise mentioned, all molecular manipulations (e.g., DNA and RNA isolation, screening cDNA libraries, Northern and Southern blot analyses, PCR, etc.) were performed using standard methods (See e.g., Sambrook et al. [1989], supra).

In the experimental disclosure which follows, the following abbreviations apply: ° C. (degrees Centigrade); rpm (revolutions per minute); IM (intramuscular); IP (intraperitoneal); IV (intravenous or intravascular); SC (subcutaneous); $H_2O$ (water); aa (amino acid); bp (base pair); kb (kilobase pair); kD (kilodaltons); gm (grams); µg (micrograms); mg (milligrams); ng (nanograms); µl (microliters); ml (milliliters); mm (millimeters); nm (nanometers); µm (micrometer); M (molar); mM (millimolar); µM (micromolar); nM (nanomolar); U (units); V (volts); MW (molecular weight); µCi (microcurrie); sec (seconds); min(s) (minute/minutes); hr(s) (hour/hours); ab (antibody); HCl (hydrochloric acid); $MgCl_2$ (magnesium chloride); KCl (potassium chloride); NaCl (sodium chloride); $OD_{280}$ (optical density at 280 mn); PAGE (polyacrylamide gel electrophoresis); PCR (polymerase chain reaction); RT-PCR (reverse transcription PCR); SDS (sodium dodecyl sulfate); Tris (tris(hydroxymethyl) aminomethane); EDTA (ethylenediaminetetraacetic acid); w/v (weight to volume); v/v (volume to volume); SSCP (single strand conformation polymorphism analysis); ATCC (American Type Culture Collection, Manassas, Va.); Bio-Rad (BioRad, Richmond, Calif.); Sigma (Sigma Chemical Co., St. Louis, Mo.); Boehringer-Mannheim, (Boehringer-Mannheim, Indianapolis, Ind.); Scan Analytics (Scan Analytics Corp., Vienna, Va.); Oncor (Oncor, Gaithersburg, Md.); Applied Biosystems (Applied Biosystems, Foster City, Calif.); Clontech (Clontech, Palo Alto, Calif.); Gibco-BRL (Gibco-BRL, Gaithersburg, Md.); Amersham (Amersham Life Sciences, Arlington Heights, Ill.); BioServe (BioServe Ltd, Laurel Md.); FMC (FMC BioProducts, Rockland Me.); Invitrogen (Invitrogen, Carlsbad Calif.); Kodak (Kodak, Rochester, N.Y.); Life Technologies (Life Technologies, Rockville, Md.); DNAStar (DNAStar Inc., Madison, Wis.); Bio 101 (Bio 101, Inc., Vista, Calif.); Ambion (Ambion, Austin, Tex.); and Axon Instruments (Axon Instruments, Foster City, Calif.).

Example 1

Positional Cloning of the $\alpha_2\delta$ Subunit Gene

A ~700kb clone contig was constructed covering the tumor suppressor gene region on human chromosome 3p21.3 defined by extensive allelotyping (Wei et al., supra] and overlapping homozygous deletions in lung and breast cancers (Wei et al. supra; Sekido et al., Oncogene 16(24): 3151–7 [1998]). This cloned DNA was used to isolate 17 resident genes by conventional laboratory techniques (Wei et al., supra). The 700 kb clone contig was sequenced by The WU Sequencing Center (St Louis, Mo., USA) and The Sanger Sequencing Centre (Hixton, UK) (FIG. 1 provides the GenBank accession numbers of sequences). The ~700 kb sequence and in silico methods were used to detect and isolate additional 9 genes residing in the 700 kb sequence bringing the total number of cloned genes to 26. Eight of these genes were encoded in the critical 120 kb region defined by the recently discovered small nesting homozygous deletion in breast cancer cell line and primary tumor HCC1500 (Sekido et al., supra). The most centromeric of these genes (the $\alpha_2\delta$ gene) was interrupted by the centromeric breakpoint of the homozygous nested deletion (Sekido et al., supra), and spanned about 140 kb of genomic DNA (FIG. 1).

A cosmid probe (LUCA8; GenBank accession # Z84495) representing a large intron of the gene also included the chromosome 3 framework genetic marker, D3S1568 (also called LUCA8.2, D354614), allocated at a 68cM distance from the telomere of the short arm on the chromosome 3 genetic map corresponding to the 3p21.3 band (FIG. 1).

The eight critical genes were extensively analyzed by bioinformatics methods and the interrupted large gene was identified as encoding at least two splice isoforms of a new calcium channel $\alpha_2\delta$ gene (FIG. 1).

Fluorescent in situ hybridization (FISH) was used to determine whether the $\alpha_2\delta$ subunit gene was indeed located in the 3p21.3 region as follows. Metaphase spreads derived from 5-bromodeoxyuridine synchronized normal peripheral lymphocytes were used as a template. Probes containing LUCA8 cosmid DNA were labeled with digoxigenin 11-dUTP by nick-translation and hybridization signals were detected with rhodamine-conjugated anti-digoxigenin antibodies (Boehringer-Mannheim). The conditions of hybridization, detection of hybridization signals, and digital-image acquisition, processing and analyses were performed as previously described (Ivanov et al., Proc. Natl. Acad. Sci USA 95(21):12596–601 [1998]). Chromosomes were identified by converting DAPI-banding into G-simulated banding using the IP Lab Image Software (Scan Analytics). Rehybridization with alpha-satellite centromeric probes (Oncor) was performed to confirm chromosomal localization. FISH analysis confirmed that the $\alpha_2\delta$ gene was located in the 3p21.3 region of chromosome 3.

Example 2

Isolation of Full-Length cDNAs Encoded by the $\alpha_2\delta$ Subunit Gene

An EST (GenBank Accession #N53512) was first detected by BLAST homology searches in the databases using the genomic sequences of contig (Wei et al., supra) cosmid LUCA11 (GenBank accession # Z84492). This EST clone was found to contain a portion of the 3' end as well as putative exons of $\alpha_2\delta$-2. Further Southern blot analysis showed that various exons of the $\alpha_2\delta2$ gene are located on cosmid LUCA6 (GenBank Accession #Z84493), LUCA7 (GenBank Accession #Z84494, LUCA8 (GenBank Accession #Z84495), LUCA9 (GenBank Accession #Z75743), LUCA10 (GenBank Accession #Z75742), and LUCA11 (GenBank Accession #Z84495). Based on GENSCAN predictions, a primer set of LUCA11r5 (5'-CTGAGAGTGAGGATGTGGAA-3' (sense primer)(SEQ ID NO:12)), and LUCA11pr18, 5'-GTGCATCCTCATACACGTTG-3' (anti-sense primer) (SEQ ID NO: 13), was used for RT-PCR amplification for normal lung cDNA template and a 960 bp product was successfully amplified. The 1.5 kb NotI/HindIII fragment of the EST clone N53512, and the 960 bp product were used as probes on human multiple tissue Northern blots (Clontech). The screening of a million clones from a lung cDNA library (Clontech) with the 960 bp RT-PCR product yielded 120 positive clones, which were also screened by probing clone N53512 to obtain the clones with long inserts. Five clones randomly selected as single positives for the 960 bp probe, and 5 clones double positive for both probes were subcloned and sequenced. All of the 10 clones had the sequence of $\alpha_2\delta$-2, suggesting that all of the 120 clones were $\alpha_2\delta$-2. Two clones (pY720c21 and pY724c95) that covered the longest sequence were assembled and further inserted into a plasmid expression vector pcDNA3.1 (Invitrogen) by standard methods (See below for additional details).

The EST was sequenced using methods known in the art. Briefly, cDNA clones were sequenced on an Applied Biosystems 373 and 377 DNA sequencers (Stretch) using Taq Dyedeoxy Terminator Cycle Sequence kits (Applied Biosystems) with either vector or clone-specific walking primers. This EST was first used as probe on commercial multiple tissues RNA Northern blots to estimate the size(s) of the mRNA(s) and to identify tissues with high expression.

For mRNA expression analyses, Northern blot hybridization was performed with $\alpha_2\delta$ cDNA probes using commercial MTN polyA RNA blots (Clontech) from a variety of adult human tissues and tumor cell lines and polyA+RNA or total RNA (JM lab) prepared from lung cancer cell lines. In these experiments, a 5.7 kb mRNA was found. In addition, the presence of the $\alpha_2\delta$ transcripts was monitored in silico by BLAST homology searches (Altschul et al., J. Mol. Biol., 215:403–410 [1990]; and Altschul et al., Nucl. Acids Res., 25:3389–3402 [1997]) in public EST databases.

Since high expression levels were detected in adult lung, testis, and brain (FIG. 2) several commercial cDNA libraries made from mRNAs of these tissues were screened to isolate overlapping cDNA clones. More than two hundred (200) cDNA clones were sequenced and shown to represent at least three distinct splice isoforms differing at the 5' end. Full-length cDNA clones for each of the three splice isoforms were then constructed and completely sequenced. In addition, cDNA clones from a commercial normal lung cDNA library (Clontech) were isolated, sequenced and shown to contain the entire open reading frame (3,435 nucleotides encoding 1,145 amino acids) of the 2 gene protein isoform I. The molecular weight of the deduced amino acid sequence was determined to be approximately 129 kDa. As indicated below, BLAST searches and homology alignment revealed that the predicted protein shares 56% amino acid sequence identity with the human auxiliary $\alpha$–$\delta$-1 subunit (GenBank Accession #M76559) of voltage-gated $Ca^{2+}$ channels.

World Wide Web based servers were used to analyze the cDNAs and deduced protein sequences. Global sequence alignments were done using BLAST and Advanced BLAST programs (Altschul et al. (1990), supra; and Altschul et al. (1997), supra), as provided by NCBI, and BLAST2/WU Blast, provided by EMBL. Multiple sequence alignments, global and local, were done using the CLUSTAL version W program as provided by EMBL and Baylor Computing Center.

Protein domains were discovered on the Pfam (Sonnhammer et al., Nucl. Acids Res., 26:320–322 [1998]; Sonnhammer et al., Proteins 28:405–420 [1997]) server, and membrane topology on the PSORT (Nakai and Kanehisa, Genomics 14:897–911 [1992]; SPLIT (Juretic and Lucin, J. Chem. Iuf. Comput. Sci., 38(4): 575–585 [1998]; and TMHMM servers.

The nucleic acid sequence of splice isoform 1 (SEQ ID NO:1) (GenBank accession #AF042792) of human $\alpha_2\delta$ subunit cDNA and its encoded amino acid sequence (SEQ ID NO:2) are provided herein. The nucleic acid sequence of splice isoform 2 (SEQ ID NO:3) (GenBank Accession #AF040709) of human $\alpha_2\delta$ subunit cDNA and its encoded amino acid sequence (SEQ ID NO:4) are also provided herein. The nucleic acid sequence of splice isoform 3 (SEQ ID NO:5) (GenBank Accession #AF042793) of human $\alpha_2\delta$ subunit cDNA and its encoded amino acid sequence (SEQ ID NO:6) are also provided herein.

Two of the cDNA clones (i.e., splice isoforms 1 and 2) predicted the same amino acid sequence (SEQ ID NOs:2 and 4) and the third clone (i.e., splice isoform 3) encoded a shorter amino acid sequence (SEQ ID NO:6) in which the first coding exon was spliced out. The longer insert sizes of 5,463 bp (splice isoform 1) and 5,482 bp (splice isoform 2) correspond to the roughly estimated major mRNA species of 5.5–5.7 kb. Splice isoform 1 and 2 cDNAs encode identical amino acid sequences (SEQ ID NOs:2 and 4) referred to as isoform I and differ only in their 5'UTRs that are followed by identical ORFs and identical 3'UTRs. The smaller cDNA of 5,279 bp (splice isoform 3) encodes a shorter amino acid sequence (SEQ ID NO:6) referred to as isoform II. The amino acid sequence of isoform II is identical to that of isoform I but is missing the first 69 amino acids. The isoform I protein is composed of 1145 amino acids predicting a theoretical pI/Mw of 5.5/129 kD; the isoform II protein comprises 1076 amino acids predicting a pI/Mw values of 5.22/122 kD. Both isoform I and II proteins are of high complexity and are not biased against any amino acids.

Example 3

Genomic Structure and Bioinformatics Analysis of the $\alpha_2\delta$ Gene

The exon-intron structure of the $\delta_2\delta$ gene was obtained by pairwise alignments of the cDNAs and genomic sequences of overlapping cosmids, LUCA 6-11 (FIG. 1). So far, 37 exons (FIG. 1) were detected bounded by consensus splice sites. In addition, exon trapping technology identified several more exons in the genomic sequence that were not present in the cDNAs. This indicates the possible existence of other isoforins generated by alternative splicing. The putative promoter of the $\delta_2\delta$ gene was identified by the PromoterScan program (Prestridge, J. Mol. Biol., 249:923–932[1995] in the upstream sequence on LUCA6 and verified by cloning and sequencing (GenBank Accession #AF042794). Thus, there are two sequences relevant to the LUCA6 cosmid. The first is "LU6 Z84493" or "LUCA6" and the second is "LU6Pr ZF042794" or "LUCA6 promoter region." It is contemplated that Z94493 is inclusive of the entire sequence.

A number of bioinformatics web based servers were used to analyze the cDNAs and the predicted protein sequences. A global BLAST (Altschul et al. [1990], supra; and Altschul et al. [1997], supra) analysis of the cDNAs and deduced protein sequences employing NCBI and EMBL servers was carried out to compare the inventions' $\delta_2\delta$ isoforms I and II with the (alpha)$_2$-subunit protein (1091 amino acids predicting a pI/Mw values of 5.10/123 kD) which is encoded by the previously reported human (alpha)$_2$-subunit isoform A gene (Ellis et al., Science 241(4873):1661–4[1988]; Williams et al., Neuron, 8(1):71–84 [1992]; Ellis et al., U.S. Pat. No. 5,686,241; and Harpold et al., U.S. Pat. No. 5,792,846). Protein and cDNA alignments of the invention's $\delta_2\delta$ isoforms I and II with the art's (alpha)$_2$-subunit sequences show 55% identity and 65% similarity on the protein level and overall 56% identity on cDNA level. It appears that $\alpha_2\delta$-2 and $\alpha_2\delta$-1 share similar overall secondary structure, as 17 out of 22 cysteines are conserved between these proteins. In addition, as with $\alpha_2\delta$-1 $\delta_2\delta$-2 contains multiple putative N-glycosylation sites and is likely to be glycosylated. Without intending to limit the invention to any particular theory or mechanism, this degree of homology suggests that the gene encoding the art's (alpha)$_2$-subunit cDNA and the gene encoding the invention's $\delta_2\delta$ subunit cDNA splice isoforms 1, 2 and 3 may be different members of a new gene family.

To further characterize the $\alpha_2\delta$ subunit gene, the predicted post-translational biochemical modifications, secondary structures, and membrane topologies of protein isoforms I and II which are encoded by the $\delta_2\delta$ gene were compared. The complexity of interactions involving the five calcium channel subunits comprising a fully functional channel is influenced by distinct post-translational biochemical modifications that include O-glycosylation, amidation, myristoylation, and, most importantly, phosphorylation of specific conserved tyrosine and senine residues. The Scan-Prosite server revealed similar distributions of potential N-glycosylation, O-glycosylation, N-myristoylation, and amidation sites in both isoform I and II proteins. The distribution of potential cAMP/cGMP-dependent protein kinase phosphorylation sites, CK2 and PKC phosphorylation sites, and tyrosine kinase phosphorylation sites was also similar among both isoform I and II proteins. Without limiting the invention to any particular mechanism, these potential post-translational modifications of the $\delta_2\delta$ proteins may add more complexity and flexibility to the variety of functions attributed to these proteins. Three putative transmembrane helices were predicted in both protein isoforms of the $\delta_2\delta$ gene with the SPLIT 35 software (Jurctic and Lucin [1998], supra; and Interestingly, isoform I of the $\alpha_2\delta$ gene has an additional membrane helix at the very amino terminus. Using the TMHMM server a isoform I protein was predicted to span the membrane only once at the amino terminus while isoform II was predicted to span the membrane once at the carboxy terminus. Without intending to limit the invention to any particular mechanism, this favors the single-transmembrane model for the $\delta_2\delta$ subunit proteins. In addition, the protein binding von Willebrand factor type A domain (VWA-like domain) (Bork et al., Biochem. J., 279 (Pt 3):908–10[1991]) was discovered by the Pfam (Sonnhammer et al. [1998], supra; and Sonnhammer et al. [1997], supra) server in the extracellular region at similar positions in both isoform I and II proteins (residues: 291–469, and 222–400 for $\delta_2\delta$ isoforms I and II respectively). While not limiting the invention to any particular theory or mechanism, the VWA-like domain may facilitate the binding of the $\delta_2\delta$ complex with the alpha I pore forming subunit (Walker and De Waard [1998] supra).

Example 4

Chromosomal Mapping of the $\alpha_2\delta$ Gene Locus

The chromosomal location of the $\alpha_2\delta$ gene locus was determined by FISH as described above (Example 1) using the cosmid LUCA8 (FIG. 1) probe which represents a large intron of the gene. The $\alpha_2\delta$ gene was localized as a single locus on 3p21.3 confirming the mapping of the microsatellite marker, D3S1568, that is located in LUCA8 sequence. This region of chromosome 3p21.3 is syntenic with mouse chromosome 9 region at position 60–70cM (homology group #25) that harbors mouse loci implicated in epilepsy, namely, E11, ducky, and tippy indicating that the $\alpha_2\delta$ gene may be responsible for these neurological phenotypes.

Example 5

Detection of Mouse Orthologous cDNA Sequences

BLAST searches in the mouse EST database maintained by NCBI detected two different non-overlapping ESTs (GenBank Accession ## AA000341 and AA08996) which showed 91% and 85% identity with the invention's $\alpha_2\delta$ cDNA ( residues 2925–3421, and 4989–5391 of splice isoform 1) respectively. These ESTs showed only limited homologies (about 50%) to the murine (alpha$_2$)-subunit genes suggesting that they represent true orthologous sequences (i.e., homologous sequences present in different organisms) of the human $\alpha_2\delta$ gene. This was further corroborated by protein alignment of the 86 amino acid ORF encoded by the EST, # AA000341 which was 96% identical to the invention's $\alpha_2\delta$ isoform I protein (residues 922–1005 of isoform I). The second EST (# AA008996) represents the 3' UTR of the mouse $\alpha_2\delta$ gene and therefore has no ORF.

Example 6

Expression Analysis of the $\alpha_2\delta$ Gene

The expression patterns of the $\alpha_2\delta$ gene were analyzed by Northern blot hybridization of human adult tissues and tumor cell lines and by monitoring EST databases. Probes for Northern analysis were labeled with a $^{32}$P-dCTP using a random primer labelling kit (Gibco-BRL). RNA was prepared from cell lines by standard techniques (See e.g., Sambrook et al., supra). Ten micrograms of total RNA (or 2 $\mu$g of poly A+RNA) from cell lines were electrophoresed in formaldehyde-1% agarose gel and transferred to Hybond N (Amersham), and membrane preparation, hybridization, and washing were performed as described using standard techniques (Sambrook et al. [1989] supra; Sekido et al., Cancer Res., 55:1227–31 [1995]; Sekido et al., Proc. Natl. Acad. Sci USA 93:4120–4125 [1996]; and Ivanov et al. [1998], supra). Human multiple tissue Northern blots I and II and human brain blot III all made with poly A+RNA were purchased from Clontech and handled as the tumor cell line Northerns. The DNA probes used for the $\alpha_2\delta$ gene were: the 1.5 kb fragment (Solution # Y612) NotI/HindIII fragment of EST clone N53512 for the tumor cell line Northerns and the Multiple Tissue Blot Northerns; and for other Multiple Tissue Blot Northerns 308 bp Probe A (Solution #Y614) (LUCA 11 pr1/pr2) and 291 bp Probe B (Solution # Y615) (LUCA 11 pr3/pr4); (LUCA11pr1:
CTCTACAACCCAATTCACCAT (SEQ ID NO:8); LUCA 11pr2:
TAGATGGCACTGGCCTTCT (SEQ ID NO:9); LUCA11pr3:
ACTCACCACCCTACTGTTC (SEQ ID NO:10); LUCA11pr4:
AGCTGCCTGTTTGGTGCTA (SEQ ID NO:11)). Northern Blots were exposed first for 1 or 4 days and then for ~30 days.

A. Expression in Normal Tissues

Figures 2A, 2B:
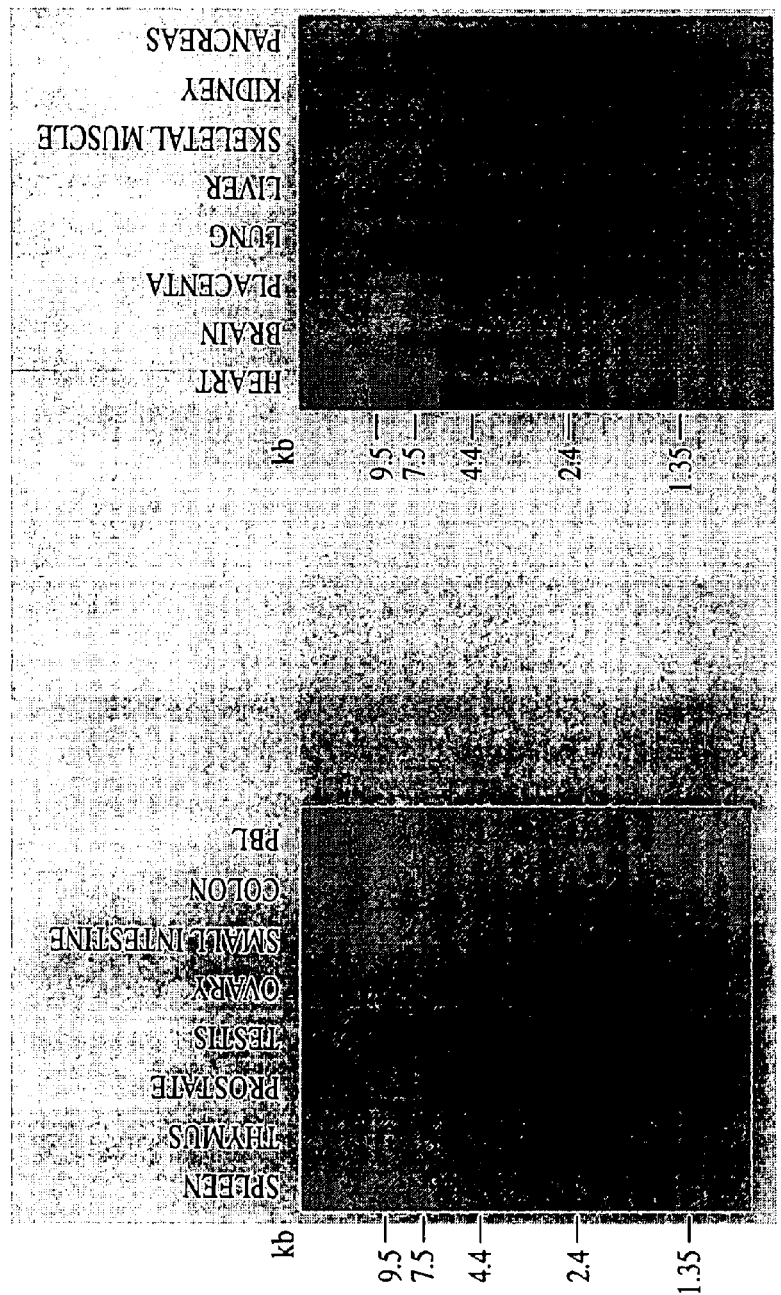
FIG. 2 (A–B) shows polyA+multiple tissue Northern blots (ClonTech) probed for $\alpha_2\delta$ expression. The tissue sources of the RNA are shown above each lane. Panel A shows a multiple tissue Northern blot with spleen, thymus, prostate, testis, ovary, small intestine, colon, and peripheral blood lymphocyte (PBL) samples, while Panel B shows a multiple tissue Northern blot with heart, brain, placenta, lung, liver, skeletal muscle, kidney, and pancreas.

A predominant 5.7 kb $\alpha_2\delta$ mRNA was seen in all normal tissues expressing the calcium channel gene and in some cases minor larger and smaller species. The highest level of $\alpha_2\delta$ expression in normal adult human tissues was found in lung and testis, with some expression also seen in heart, brain, skeletal muscle, pancreas, spleen, prostate, ovary, small intestine, and peripheral blood lymphocytes. Northern blot results from various tissue sources are shown in FIG. 2. In this Figure, Panel A shows the results for samples from spleen, thymus, prostate, testis, ovary, small intestine, colon, and peripheral blood lymphocytes (PBL), while Panel B shows the results for samples from heart, brain, placenta, lung, liver, skeletal muscle, kidney, and pancreas. The calcium channel $\alpha_2\delta$ gene was also expressed extensively in all different areas of the brain tested in an additional multiple tissue Northern blot (e.g., thalamus, subthalamic nucleus, substantia nigra, whole brain, hippocampus, corpus callosum, caudate nucleus, and amygdala samples; results not shown).

B. Expression in Lung Cancers

A predominant 5.7 kb mRNA was also seen in lung cancer cell lines that expressed the $\alpha_2\delta$ calcium channel gene. Various cell lines were used in these experiments, including a B lymphoblastoid cell line, and lung cancer cell lines designated as NCI lines (e.g., NCI-H82). The histologies of the lines tested included small cell lung cancer (SCLC), NCI-H82 (SCLC), H146 (SCLC), H249 (SCLC), H524 (SCLC), H740 (SCLC), H1514 (SCLC), H1618 (SCLC), H2141 (SCLC), H2171 (SCLC), H2227 (SCLC), H187, H209, H345, H378, H524, H526, H865, H889, H1045, H1092, H1105, H1238, H1514, H1618, H1672, H1963, H2141, H2171; non-small cell lung cancers (NSCLC), H358 (NSCLC, adeno/bronchoalveolar), H838 (NSCLC, adeno), H1792 (NSCLC, adeno), H2077 (NSCLC, adeno), H460 (NSCLC, large cell), H1155 (NSCLC, large cell), H1299 (NSCLC, large cell), H720 (carcinoma); H28 (mesothelioma); H290 (mesothelioma), H2052 (mesothelioma), H23 (adeno), H322 (adeno), H1437 (adeno), H1666 (adeno), H2009 (adeno), H661 (large cell), H2106 (large cell), and NCI-H460 (NSCLC, large cell). These lines have been deposited with the American Type Culture Collection (ATCC).

After exposure for 1 day for poly A$^+$ RNA blots, or 4 days for total RNA blots, only a few tumor cell lines showed detectable signals. After prolonged 30 days' exposure some additional tumor lines showed expression. Overall, $\alpha_2\delta$ expression was found in 41 lung cancer samples as follows: 19 expressed the gene and 22 had no, or very weak, expression. As a function of histologic type: Small cell lung cancers: 15 expressed, 8 had no, or very weak, expression; Non-small cell lung cancers: 4 expressed, 10 had no, or very weak, expression; mesotheliomas: all 3 had no, or very weak, expression; carcinoid: 1 had no expression.

In an additional set of experiments using polyA+RNA prepared from 14 SCLC lines and 11 NSCLC lines, only about 35% of the cell lines tested showed low levels of expression and the rest no expression at all. These results collectively suggest that the $\alpha_2\delta$ gene is silenced during lung carcinogenesis.

C. EST Database Analysis

The EST matches were mostly in the testis, lung, and brain libraries (85%). Several ESTs were detected in libraries made from tumor tissues, namely, prostate, lung, and ovarian carcinomas. (NCBI, dBEST, NCI CGAP database, These combined results suggest that the $\delta_2\delta$ gene is gene is expressed in several normal tissues and that its expression is particularly high in lung and testis (as compared to other normal tissues tested). However, the dramatic reduction in the levels of expression of the $\delta_2\delta$ subunit gene in lung cancer cell lines as compared to the levels of expression in normal lung cells suggests that the $\delta_2\delta$ subunit gene is involved in carcinogenesis.

Example 7

Mutation Analysis of $\alpha_2\delta$ Subunit Gene

Mutations in the $\alpha_2\delta$ subunit gene were analyzed in lung and breast cancer cell lines using Southern blot analysis, exon-PCR using intronic primers, reverse transcription polymerase chain reaction (RT-PCR) and single strand conformation polymorphism analysis (SSCP) followed by sequencing as described below.

A. Southern Blot Analysis

For Southern blot analysis, probes were labeled with a $^{32}$P-dCTP using a random primer labelling kit (Gibco-BRL). Restricted DNAs (5 or 10 µg) were run on a 0.8% agarose gel, transferred and UV cross linked to Hybond N+membranes (Amersham). Hybridization was performed at 65° C. overnight, and the filters were washed and subjected to autoradiography. Southern blot analysis with an $\alpha_2\delta$ gene probe was performed on >100 lung cancer cell line and 26 breast cancer cell line cDNAs. This led to the discovery of another homozygous nesting deletion involving $\alpha_2\delta$ in a breast cancer cell line HCC1500 (Sekido et al., Oncogene 16:3151–3157 [1998]).

B. Exon-PCR-SSCP

To perform Single Strand Polymorphism Analysis (SSCP), PCR primer pairs (Table 1) were designed to amplify $\alpha_2\delta$ gene sequences which range in size between 80 and 298 pb. In this Table, "LU11" refers to Z84492, or LUCA11, while "LU9" refers to Z75743 or LUCA9, "LU7" refers to Z74484 or LUCA7, and "LU6 (5'UTR)" refers to Z84493 or LUCA6.

TABLE 1

Primer Pairs for SSCP Analysis of α 2 δ Gene

| Primer Name | Primer Sequence | size (bp) | Cosmid | SNP |
|---|---|---|---|---|
| c16E3F | GAC AAG CCA CCC CTT ACC TAC (SEQ ID NO:14) | | | |
| c16E3R | GCA GAG CCC AGT TCT GGC TG (SEQ ID NO:15) | 228 | LU11 | |
| c16E4F | CCA GCA TAG AGT GGT CAG TG (SEQ ID NO:16) | | | |
| c16E4R | AGT ACC CTG TCC ATT GCC TG (SEQ ID NO:17) | 210 | LU11 | |
| c16E5F | GGC AGG TAG CAC TGA TGG TC (SEQ ID NO:18) | | | |
| c16E5R | TTG GAG CCA CTG AGT GGA AG (SEQ ID NO:19) | 217 | LU11 | |
| c16E6F | GTG GCT TAC GGT CCT CAC TC (SEQ ID NO:20) | | | |
| c16E6R | TGT GCT GGG AGT CGC GGC TG (SEQ ID NO:21) | 169 | LU11 | |
| c16E7F | ACC ACT GGA CTG CCT GCG GTG (SEQ ID NO:22) | | | |
| c16E7R | CAG GGC TGG CAG TGC TAC AC (SEQ ID NO:23) | 226 | LU11 | |
| c16E8F | ACT GCC AGC CCT GTG ACC ATG (SEQ ID NO:24) | | | |
| c16E8R | CCA TCT CCA GTC CAG GCA TC (SEQ ID NO:25) | 229 | LU11 | yes |
| MJE2F | TTC GAC AGG ACA CAG CCC AG (SEQ ID NO:26) | | | |
| MJE2R | TGC TGG GTA GAC AGG GGA CAG (SEQ ID NO:27) | 221 | LU11 | |
| MJE3F | AGC CCA GTC GCC TCT GCA AG (SEQ ID NO:28) | | | |
| MJE3R | TGG ATA CAG CTG GCT GCG CC (SEQ ID NO:29) | 235 | LU11 | |
| MJE4F | CCT TAC CCT AAC AGA GGC ATC (SEQ ID NO:30) | | | |
| MJE4R | AAC CTC ACG TGT TCT CCT GC (SEQ ID NO:31) | 189 | LU11 | |
| MJE5F | TGG GCA GGA GAA CAC GTG AG (SEQ ID NO:32) | | | |
| MJE5R | CTG GTG ATG GTC ACA GGA GC (SEQ ID NO:33) | 236 | LU11 | |
| MJE6F | AGG CCA CTC ACC ACC CTA CTG (SEQ ID NO:34) | | | |
| MJE6R | TCC TGG GTA CAC CAA GCC AG (SEQ ID NO:35) | 259 | LU11 | |
| MJE7F | GGA GGG CTG AGA GCT GCC TG (SEQ ID NO:36) | | | |
| MJE7R | TTG AGG TTA CTG CTG TGG CCA C (SEQ ID NO:37) | 235 | LU11 | |
| MJE8F | CTG GTG GCC ACA GCA GTC AC (SEQ ID NO:38) | | | |
| MJE8R | GGA TGG CCA GTT GAA CAT ACG (SEQ ID NO:39) | 183 | LU11 | |

TABLE 1-continued

Primer Pairs for SSCP Analysis of α 2 δ Gene

| Primer Name | Primer Sequence | size (bp) | Cosmid | SNP |
|---|---|---|---|---|
| g26MJ2FA | TTC GAC AGG ACA CAG CCC AG (SEQ ID NO:40) | | | |
| g26MJ2RA | GTG CTG GGT AGA CAG GGG ACA GG (SEQ ID NO:41) | 222 | LU11 | yes |
| g26MJ5F | TGG GCA GGA GAA CAC GTG AG (SEQ ID NO:42) | | | |
| g26MJ5RA | CTG GTG ATG GTC ACA GGA GC (SEQ ID NO:43) | 235 | LU11 | |
| LU9F | ACC CCT GGC TTC TGC TTC CTT (SEQ ID NO:44) | | | |
| LU9R | ACA CTG CCC TCA TGG TAC AG (SEQ ID NO:45) | 221 | LU9 | yes |
| LU10-1F | ACC TCC CTG TGC TCT GTC CCT CA (SEQ ID NO:46) | | | |
| LU10-1R | AAT CCA CGC ATG GAT GGG CA (SEQ ID NO:47) | 150 | LU9 | |
| LU10-2F | TGA GCA GCT AGT GCT GAG GCC TCT (SEQ ID NO:48) | | | |
| LU10-2R | CAG CAA GGA GGT GTG GCT CAG GA (SEQ ID NO:49) | 117 | LU9 | |
| geneX1F | ACT CCA AGC AGT GTG AGT GC (SEQ ID NO:50) | | | |
| geneX1R | GAA GGA AGT TGT TGC CTG GAA (SEQ ID NO:51) | 261 | LU9 | |
| geneX2F | CAG GTG TGG AAA TAA GCA GG (SEQ ID NO:52) | | | |
| geneX2R | CAT CTT CTT GCA GCT CCT TG (SEQ ID NO:53) | 124 | LU9 | |
| gx LU94F | TGC CCT TGT TAC AGT CAT CTC CA (SEQ ID NO:54) | | LU9 | |
| gx LU93F | TAA GAT GAA AAG CCA GCC AGC TG (SEQ ID NO:55) | | LU9 | |
| genxLU92F | GTC TCC TCT TTG GAC AGA TTC TG (SEQ ID NO:56) | | | |
| genxLU92R | TGG AGA TGA CTG TAA CAA GGG CAC (SEQ ID NO:57) | 115 | LU9 | |
| gxLU93R | AAG AGG AGA CTT CCC AGT CTC TTG (SEQ ID NO:58) | | LU9 | |
| g26Ef | CTG CAT ACA GGA TGC AGC ACT G (SEQ ID NO:59) | | | |
| g26Er | GCT CAC CTC ACG GAG CTG CTG CGA (SEQ ID NO:60) | 88 | LU7 | yes |
| GXHf | TGT TCA GCC CAG GGA AGC GAA GC (SEQ ID NO:61) | | | |
| GXHr | ACT TAC AGC CCC CGT GGC TCT AG (SEQ ID NO:62) | 197 | LU6 (5'UTR) | |
| -1ex1F | CCT GGC TCT GGA AGA ATC TA (SEQ ID NO:63) | | | |
| -1ex1R | CAG AAA AGG AGG CAT GCT GA (SEQ ID NO:64) | 298 | LU6 (5'UTR) | |
| -1ex2F | AAG CGA GTG GCT GCA GAG (SEQ ID NO:65) | | | |
| -1ex2R | CTA AGC GGA AAC CTG GGC A (SEQ ID NO:66) | 80 | LU6 (5'UTR) | |

Each pair of primers (prepared by Gibco-BRL; BioServe; see Table) was tested for the optimal cycling conditions by running the product on a 4% 3:1 Nu-Sieve agarose gel (FMC). A typical cycling program included: 3 minutes at 95° C., 35 cycles of 1 minute at 95° C., 1 minute at the optimal annealing temperature, 1 minute at 72° C. followed by 7 minutes at 72° C. CEPH family-heads DNA was used as positive control; homozygously deleted cell line DNAs was used as negative control. PCR products were eventually cloned by means of TA Cloning Kit (Invitrogen). The radioactive reaction was performed in a total reaction volume of 12.5 μl containing 100 ng of genomic DNA, 12.5 pmol of each primer, 200 μM dNTPs, 1.5 mM MgCl$_2$, 1.25 nCi $^{35}$S-dATP. After heat denaturation (8 min at 90° C.) in formamide buffer (Stop Solution, Amersham), PCR products were run overnight in a 0.5×MDE gel (FMC), 0.6×TBE, at room temperature, 8 W constant power; blotted, dried and exposed to autoradiography film (X-OMAT AR, Kodak).

C. RT-PCR and SSCP

PCR amplified exons or RT-PCR amplified mRNA fragments were subjected to SSCP analyses followed by sequencing when gel shifts were evident as follows. Random-primed, first-strand cDNAs were synthesized from total RNA (13 μg/20 μl reaction) using Superscript II (Life Technologies) according to the manufacturer's instructions. All of these samples were shown to successfully amplify for glyceraldehyde 3-phosphate dehydrogenase (GAPDH) cDNA as a control test of the quality of the random primed cDNA. One μl of the random-primed cDNA was subjected to non-nested PCR in a volume of 20 μl containing 1 μM of each primer; 250 mM of dGTP, dATP, and dTTP; 25 mM of "cold" dCTP; 0.05 μl of 3000 mCi/mmol [32P]dCTP (Amersham); 1×reaction buffer (Life Technologies); 2.0 mM MgCL; 5% DMSO; and 1.25 of Taq polymerase in a Perkin-Elmer 9600 thermocycler, using 23 primer sets amplifying the Calcium Channel gene (CACNA2D2) open reading frame exons provided coverage for mutation scanning from nt 164 to 3679 of the AF040709 sequence, as shown in Table 2.

for 24 h. Shifted SSCP bands were excised from the MDE gels, and the DNA was eluted with distilled water and re-amplified using the original PCR primers. The PCR product was run on a 2% agarose gel and purified by GeneClean (Bio 101). Automated bi-directional sequencing was performed by ABI 377 Dye Terminator cycle sequencing. Sequences were analyzed and compared to wild-type

TABLE 2

Primers Used for Single Strand Conformation Polymorphism (SSCP) and RT/PCR cDNA Analysis of a2d-2 Gene
(Nucleotides refer to the AF040709 sequence location)

| Forward Primers | 5'→3' | Nucleotides | Reverse Primers | 5'→3' | Nucleotides | Product Size |
|---|---|---|---|---|---|---|
| g97F | GCA TCT TGA ATG GAA ACA TGG C (SEQ ID NO:67) | 164–185 | 16GR | TCG ACC TCC TGC TCC AGA (SEQ ID NO:68) | 408–425 | 262 |
| 15GF | AGC ACA CGA TGC AGC ACT G (SEQ ID NO:69) | 380–398 | 15GR | CTT CTC CAC CAA CTT CTG AG (SEQ ID NO:70) | 515–534 | 155 |
| LO9s12075 | ACA ACC GGA ACC TGT TCG A (SEQ ID NO:71) | 479–497 | e80R | CGT CAT AGT ACA CGA TGT CTT C (SEQ ID NO:72) | 649–670 | 192 |
| e79F | ATG CTG CAG AGA ACT TCC AG (SEQ ID NO:73) | 596–615 | L11pr42 | TGA AGT TTG GGT CCT CGA TG (SEQ ID NO:74) | 753–772 | 177 |
| pr5 | CTG AGA GTG AGG ATG TGG AA (SEQ ID NO:75) | 698–718 | pr44 | AAG ACC TGC CAC AGC AGT G (SEQ ID NO:76) | 911–929 | 232 |
| pr51 | GTG TTC ATG GAA AAC CGC AG (SEQ ID NO: 77) | 880–899 | pr52 | CCA CTC ACA TCC ACG ATG ATG (SEQ ID NO:78) | 1059–1079 | 200 |
| pr53 | CTG TAC GAT GTC CGA AGG AGA C (SEQ ID NO:79) | 997–1018 | pr54 | TGT GAA GCA TGA CAC AGG CTG (SEQ ID NO:80) | 1189–1209 | 213 |
| pr55 | ATC TGT CTG CGA GAT GCT GG (SEQ ID NO:81) | 1116–1135 | pr16 | TTC TGC AGC TGG TCA AAG G (SEQ ID NO:82) | 1313–1331 | 216 |
| pr57 | CGC AAC AAG AAG GTG TTC AAG (SEQ ID NO:83) | 1231–1251 | pr58 | GCC CCA CGG AGA AAG TAA AC (SEQ ID NO:84) | 1449–1468 | 238 |
| pr59 | TGT TCA CGG ATG GTG GTG AG (SEQ ID NO:85) | 1373–1392 | pr60 | TTC CTG TGT GTT GAT GCG G (SEQ ID NO:86) | 1554–1572 | 200 |
| g81F | TTG AGA TCC CTT CCA TCG G (SEQ ID NO:87) | 1529–1547 | g82R | GCT GGT TCT TCT TTT CCC CAG (SEQ ID NO:88) | 1718–1738 | 210 |
| g83F | GTG GTA ACA GGG ACC CTC CCT (SEQ ID NO:89) | 1672–1692 | g84R | AGA TTG GGG TGC AGC AAC AC (SEQ ID NO:90) | 1852–1871 | 200 |
| g85F | GCT ATG TGT TTG CCA TTG ACC (SEQ ID NO:91) | 1820–1840 | g86R | CTA TGT ACC TCT CAT CCA GGG AC (SEQ ID NO:92) | 2013–2038 | 219 |
| g87F | CAT GAT TGA TGG CAA CAA GG (SEQ ID NO:93) | 1965–1984 | g88R | GGG GAG CAG GAA CTC AAA ATA C (SEQ ID NO:94) | 2163–2184 | 220 |
| g89F | GCC AAT CTC AGT GAC CAG ATC C (SEQ ID NO:95) | 2131–2152 | g90R | AGG TTG TGC AGA AGG AAG TTG (SEQ ID NO:96) | 2328–2348 | 218 |
| g91F | AGA AAG TGA CTC CAG ACT CCA AG (SEQ ID NO:97) | 2297–2319 | g92R | TTG AAG GGC TCA GGG TTC TC (SEQ ID NO:98) | 2497–2516 | 220 |
| pr61 | GGA TCT CAA CAC GTA CAG CCT AC (SEQ ID NO:99) | 2403–2425 | pr62 | GGA TGC CCA CAG TGT CAT TC (SEQ ID NO:100) | 2607–2626 | 224 |
| pr63 | CCC TTC AAT GCC AGC TTC TAC (SEQ ID NO:101) | 2508–2529 | pr64 | AAC TTC TCA GCC CAA GCC TC (SEQ ID NO:102) | 2704–2723 | 216 |
| pr65 | AAT GAC ACT GTG GGC ATC CTC (SEQ ID NO:103) | 2608–2629 | pr66 | TTA ACC TCG CAG TCC ATC TCA C (SEQ ID NO:104) | 2789–2810 | 203 |
| pr67 | ACC AAG ACC AGC CTC AGA AGT G (SEQ ID NO:105) | 2750–2771 | pr68 | ATA GGA CTC CTT GCG GGT GTA G (SEQ ID NO:106) | 2952–2973 | 224 |
| pr69 | AGG TGG ATG CCA ACC TGA TG (SEQ ID NO:107) | 2908–2928 | pr70 | CGT AGA GAA GCT GCT GGA ACA G (SEQ ID NO:108) | 3100–3122 | 215 |
| pr71 | CAC CGT TGC AGA TTT CCT TAA C (SEQ ID NO:109) | 3045–3066 | pr72 | AGT TTC CGC AGT CGA TGA TG (SEQ ID NO:110) | 3252–3272 | 228 |
| pr73 | GAA ACA GAC CCA GTA CTA CTT C (SEQ ID NO:111) | 3204–3225 | pr74 | GCG TGG TAG TCG AAG CAG AT (SEQ ID NO:112) | 3454–3473 | 270 |
| pr75 | AGC AGT GTG AGC TAG TGC AG (SEQ ID NO:113) | 3407–3426 | pr76 | AGG GTG GGA AAG GCG AAG A (SEQ ID NO:114) | 3661–3679 | 273 |

Most of these primer sets amplified fragments of <225 bp of cDNA while two amplified 270 bp of cDNA for optimal mutation detection. A modified touch-down PCR (initial denaturation at 94° C. for 2.5 min, followed by 5 cycles of 30 s at 94° C., 30 s at 68° C., 30 s at 72° C., and then 30 cycles of 30 s at 94° C., 30 s at 72° C., and a final extension for 10 min at 72° C.) was used. The samples were heat denatured, snap chilled, and run on 0.5×Mutation Detection Enhancement (MDE) gels (FMC) with and without 10% glycerol at 5 W overnight, and subjected to autoradiography Calcium channel gene (CACNA2D2) sequences with DNAStar software.

Fifty-nine lung cancer cell line samples (33 small cell lung cancer and 26 non-small cell lung cancers) were tested for mutations by this SSCP method and no amino acid altering mutations were found. As a control normal lung cDNA was also run. In the course of cDNA and SSCP sequencing, at least four (4) single nucleotide polymorphisms (SNPs) were recorded. The previously known microsatellite polymorphic locus, D3S1568, was detected in the sequence of a large intron of the $\alpha_2\delta$ gene.

However, 19 (19/59, i.e., 32%) of the lung cancer cDNA samples gave a blank signal on repeated testing of their cDNAs for several of the primer sets. Without limiting the invention to any particular theory or mechanism, these results indicate either extremely low levels of expression of the gene in lung cancer cell lines and/or modifications in the cDNA which disrupt the open reading frame.

Example 8

Generation of Polyclonal Antibodies Against $\alpha_2\delta$ Subunit Isoform I and Expression of $\alpha_2\delta$ in Lung Cancer Cells The coding region of the cDNA splice isoform 2 (SEQ ID NO:3) (3,442 bp, nt 175 to nt 3,616) was cloned into each of the following three expression vectors: pcDNA3.1 His C (Invitrogen) at the BamHI/NotI site (CMV expression vector), pLJ17 (pAdE1/CMV) at the BamHI/NotI site (adenovirus shuttle vector), and pRev-TRE vector (ClonTech) at the BamHI/SalI site (retrovirus tetracycline regulatable vector). The 3,442 bp construct was subjected to in vitro translation giving a product of ~130 Kd which compares well to the calculated molecular weight of 129,268 Daltons.

NCI-H1299 non-small cell lung cancer cells were transfected with plasmid pcDNA3.1($\alpha_2\delta$) (i.e., the above-described pcDNA3.1 p1HisC plasmid into which the cDNA splice isoform 2 was cloned) and tested in in vitro translation experiments using $^{35}$S-methionine in an in vitro transcription/translation system (TNT Coupled Reticulocyte Systems, Promega). For transfection experiments, NCI-H1299 cells (3×10$^5$) were seeded in 3.5 cm culture dishes for 24 h in RPMI 1640 containing 5% fetal bovine serum. Then, 1 μg of cloned DNA was introduced into the cells using the lipofectamine reagent (Gibco-BRL). For protein expression after transfection, cells were harvested 48 hrs later and lysed in 80 μl of sample buffer (50 mM Tris, pH 6.8; 1% SDS, 10% glycerol and 0.3M of β-mercaptoethanol). NCI-H1299 cells were used for these studies because they do not express endogenous $\alpha_2\delta$-2 mRNA or protein, and are homozygous for multiple polymorphic markers in the 600 kb homozygous deletion region, and thus have undergone loss of heterozygosity for this region.

After transient expression, Western blot analysis using affinity purified rabbit polyclonal anti-peptide antibody which was raised against $\alpha_2\delta$ subunit amino acids 161–181 (peptide A) of SEQ ID NO:4 was used to detect the expressed protein. Western blots showed a band at ~150 Kd and also at ~300 Kd area in a non-reduced 4–15% gradient PAGE using the polyclonal antibody against peptide A. It is possible that the increase in the apparent molecular weight (i.e., approximately 129 to 150 kDa) compared to the conceptually translated protein and the in vitro translated protein is the result of N'-glycosylation, in agreement with multiple putative N-glycosylation sites in the $\alpha_2\delta$-sequence which represent known properties of the $\alpha_2\delta$-1 protein (Gurnett et al., Neuron 16(2):431–440 [1996]). Endogenous $\alpha_2\delta$-2 protein of 150 kDa was also detected in some lung tumor cell lines using the same antibody, further confirming that the conceptual translation and anti-peptide antibody preparation were correct.

After reducing the protein with beta-mercaptoethanol only a single band was observed at ~150 Kd. This is in contrast to the result with the previously reported (alpha$_2$)-subunit gene (Ellis et al. [1988], supra; Williams et al. [1992], supra; Ellis et al., U.S. Pat. No. 5,686,241; and Harpold et al., U.S. Pat. No 5,792,846) which showed a reduction in size after treatment with a reducing agent. While not intending to limit the invention to any particular mechanism, these results demonstrate that while the previously reported human (alpha$_2$)-subunit gene is processed into two subunits, the $\alpha_2\delta$ subunit gene of the invention may be processed in a similar or different manner.

Figures 3A, 3B, 3C:
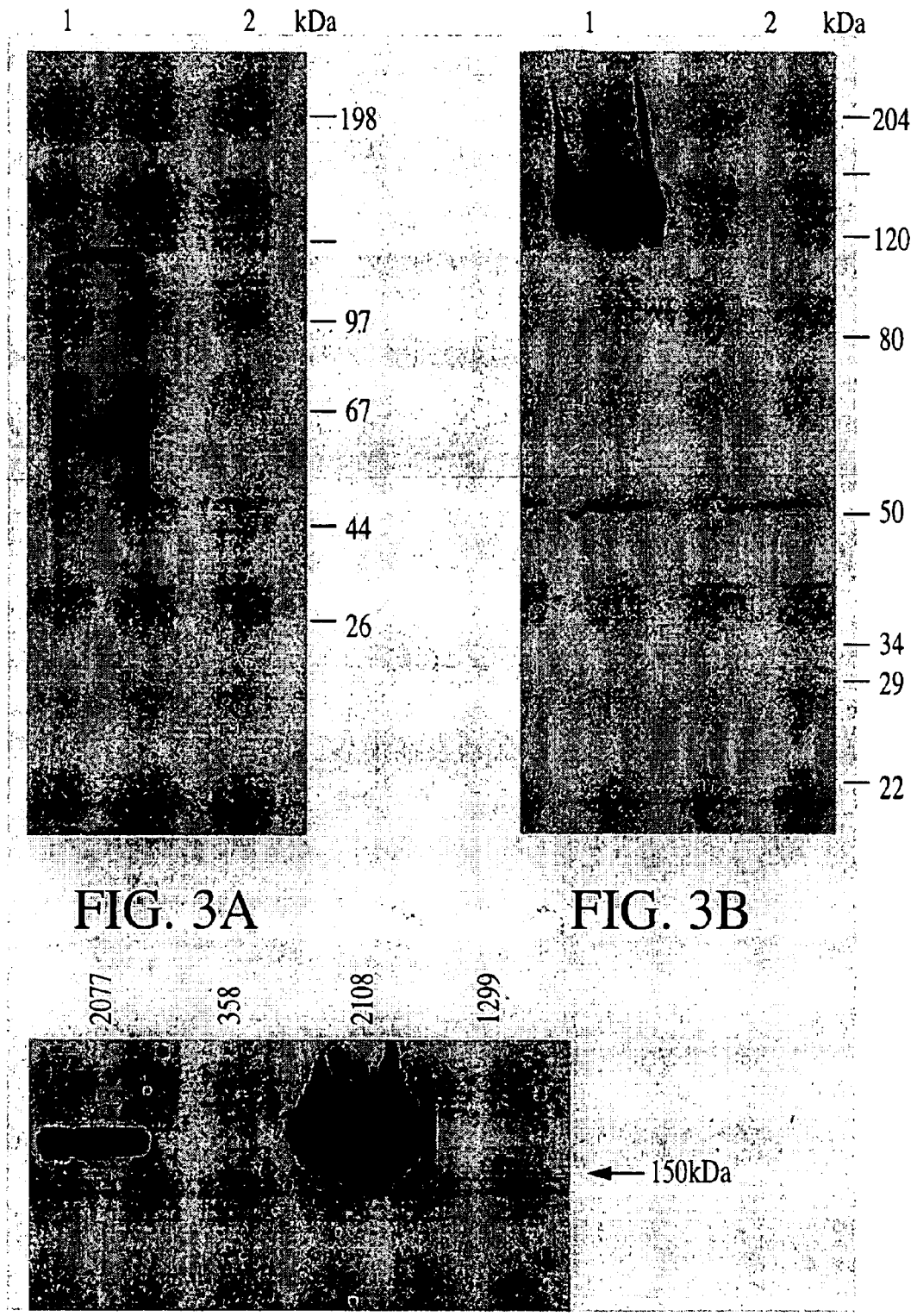
FIG. 3 provides Western blot data from transcription and translation experiments. Panel A provides results from in vitro transcription and translation of $\delta_2\delta$-2 in expression vector pcDNA3.1 and a control sample. Panel B provides results for transfection of NCI-H1299 cells with $\delta_2\delta$-2 and a control. Panel C provides results for protein obtained from tumor lysates.

FIG. 3 provides Western blot data showing the results of in vitro transcription and translation of $\alpha_2\delta$-2 experiments. In Panel A, lane 1 contains the products of in vitro transcription and translation of $\alpha_2\delta$-2 in expression vector pcDNA3.1. In lane 2, no DNA was added in the same reaction. The arrow indicates the expected approximately 130 kd product. In Panel B, results from Western blot analysis of transfection of NCl-H1299 cells with $\alpha_2\delta$-2 are shown. Lane 1 shows the results for NCI-H1299 cells with $\alpha_2\delta$-2 in expression vector pcDNA3.1. Lane 2 shows the results for NCI-H1299 cells transfected with pcDNA3.1 vector alone. In these Westerns, affinity-purified anti-$\alpha_2\delta$-2 peptide antibody was used to detect the protein product. The arrow in the Figure indicates the expected protein product. Sizes of the prestained protein molecular weight markers are indicated on the right. In Panel C results are shown for protein from tumor lysates (loaded at 40 μg per lane). Lane 1 contains protein lysate from NCI-H2077 cells (adenocarcinoma), lane 2 contains lysate from NCI-H383 cells (adenocarcinoma), lane 3 contains lysate from NCI-H2106 cells (large cell neuroendocrine carcinoma), and lane 4 contains lysate from NCI-H1299 cells (large cell carcinoma). As indicated above, the results shown in Panel C indicate that endogenous $\alpha_2\delta$-2 protein of 150 kDa was detected in some lung tumor cell lines (using the same antibody as with other preparations), further confirming that the conceptual translation and anti-peptide antibody preparation were correct.

Example 9

Regulation of Calcium Ion Flux in vitro by the $\alpha_2\delta$ Subunit Through Cancer Cells and Oocytes The bioinformatics analysis of the $\alpha_2\delta$ subunit gene and its isoforms clearly demonstrated that this is a new human gene coding for at least two $\alpha_2\delta$ subunits of the voltage-gated plasma membrane calcium channels. It is the inventors' consideration that the single polypeptide products of the gene are post-translationally cleaved into the $\alpha_2$ and $\delta$ polypeptide subunits which, after extensive biochemical modifications, form the $\alpha_2\delta$ protein complex that is necessary to assemble a fully functional plasma membrane calcium channel(s).

Two series of experiments are conducted to ascertain the subunit function of the gene products in regulating calcium ion flux in vitro across cell membranes. First, cDNA sequences (which correspond to ORFs of GenBank Accession ## AF040709, AF042792 and AF042793) and which code for both isoform I and isoform II variants respectively were inserted into the tetracycline controlled episomal expression vectors Tet OFF (Clontech) or pETE. In the Clontech Tet OFF system the gene is not expressed (or expressed at very low levels) in the presence of doxycycline and expressed at very high levels in the absence of doxycycline. The pETE vector is derived from the commercially available Tet OFF vector (Clontech) by inserting an EBNA-1 element to confer an episomal property on the vector. The pETE vectors were then transfected into lung cancer (e.g., NSCLC NCI-H1299, H1607, and A549) and nasopharyngeal cancer cells (HONE-1) which were specifically engineered to constitutively express the tetracycline-controlled transcription activator (TA) by infecting the tumor cells with a retrovirus expressing TA. In this system the transfected genes were highly-to-moderately expressed (as determined by Northern analysis) in the absence of tetracycline and not expressed at all in the presence of tetracycline or its analog, doxycycline. These results demonstrate high level expression in vitro in cancer cells of each of isoforms I and II of the $\alpha_2\delta$ subunit protein.

Clonal NCI-H1299 cell lines constitutively expressing high levels of the $\alpha_2\delta$ subunit polypeptide have already been developed. Clonal cell lines which express high levels of the transfected $\alpha_2\delta$ subunit proteins in a tetracycline controlled fashion are developed by selecting and clonally expanding only transfected cell which express high levels of the subunit. These clonal cell lines are used to measure calcium ion fluxes in the presence and absence of tetracycline or doxycycline special fluorescent staining as previously described (McEnery [1998], supra). Voltage dependent calcium channels:structural insights into channel function, pharmacology, and assembly in health and disease (McEnery [1998], supra). In this setting, it may be established whether the expression of the $\alpha_2\delta$ subunit gene products in cells which otherwise lack expression of endogenous $\alpha_2\delta$ subunit gene would increase calcium entry into the cells as compared to control cells (i.e., a corresponding cell which has not been transfected with the expression vector that encodes the $\alpha_2\delta$ subunit).

Secondly, frog oocytes expressing calcium channels that do not contain $\alpha_2\delta$ subunits may be prepared using methods known in the art (See e.g., Ellis et al. U.S. Pat. No. 5,686,241, and Harpold et al., U.S. Pat. No. 5,792,846, the contents of both of which are herein incorporated by reference). These oocytes are used to test whether a fully functional calcium channel may be reconstituted. This is achieved by introducing recombinant plasmids expressing $\alpha_2\delta$ subunit proteins into these frog oocytes and by measuring calcium fluxes in the transfected cells as compared to control cells. Controls include oocytes which express calcium channels that do not contain $\alpha_2\delta$ subunits and which are not transfected with recombinant plasmids that express $\alpha_2\delta$ subunit proteins. Another control includes oocytes which express a calcium channel that contains $\alpha_2\delta$ subunits and which are not transfected with the recombinant plasmids that express $\alpha_2\delta$ subunit proteins.

Example 10

Electrophysiologic Studies

In these experiments, co-expression of $\alpha 1B$ and $\beta 3$ subunits was investigated. Complementary RNA (cRNA) encoding human brain $\alpha 1B$, rabbit skeletal muscle $\alpha_2\delta$-1, rabbit $\beta_3$, and $\alpha_2\delta$-2 subunits were synthesized in vitro using T7 RNA polymerase, resuspended in water at a final concentration of ~1 mg/ml and stored at $-80°$ C. until injection. Xenopus oocytes harvested by standard methods known in the art were injected with a mixtures of the following transcripts: $\alpha 1B+\beta_3$, $\alpha 1B+\alpha_2\delta$-1 $\alpha 1B+\beta_3+\alpha_2\delta$-2 or $\alpha_2\delta$-2 alone (approximately 50 ng total cRNA/oocyte). Two days later, the oocytes were analyzed using standard two-electrode voltage-clamp technique with 5 mM $Ba^{2+}$ as a charge carrier, as known in the art. The holding potential was $-120$ mV. Currents were recorded in response to test potentials ranging from $-110$ to $+100$ mV, filtered at 200 Hz, then analyzed using pClamp 6.04 (Axon Instruments) and Origin (Microcal) software. Leak and capacitance currents were subtracted on-line with a P/4 protocol.

For the studies of coexpression with $\alpha 1C$ and $\alpha 1G$ subunits, cRNA of either $\alpha 1C$, $\alpha 1G$, or $\alpha_2\delta$-2 cDNA was synthesized using Ambion Megascript Kit according to the supplier's protocol (Ambion). Due to low expression of wild-type $\alpha 1C$, the modified cDNA, $\Delta N60$, which is truncated by 60 amino acids at the N-terminal end of the rabbit cardiac $\alpha 1$ subunit was used. The rat brain $\alpha 1G$ cDNA was contained in the vector pGEM-HE. Fifty nl of cRNA (5 ng for $\alpha 1C$; 5 ng for $\alpha 1G$; and 2.5 ng for $\alpha_2\delta$-2) of either $\alpha 1C$ alone, $\alpha 1C$ plus $\alpha_2\delta$-2, $\alpha 1G$ alone, or $\alpha 1G$ plus $\alpha_2\delta$-2, were injected into each oocyte using a Drummond Nanoject pipette injector (Parkway, PA). Expression of injected cRNA was measured from the 4th day after injection for $\alpha 1C$ alone or $\alpha 1C$ plus $\alpha_2\delta$-2, and the 6–7th day after injection for $\alpha 1G$ alone, or $\alpha 1G$ plus $\alpha_2\delta$-2 using the two-electrode voltage clamp method known in the art. Currents were measured in either 40 mM $Ba^{2+}$ solution (40 mM $Ba(OH)_2$, 50 mM NaOH, 1 mM KOH, and 5 mM HEPES, adjusted to pH 7.4 with methanesulfonic acid) for L-type currents, or 10 mM $Ba^{2+}$ solution (10 mM $Ba(OH)_2$, 80 mM NaOH, 1 mM KOH, and 5 mM HEPES, adjusted to pH 7.4 with methanesulfonic acid) for T-type currents. Data were sampled at either 2 KHz for L-type currents, or 5 KHz for T-type currents using the pClamp 6 system via a Digidata 1200 A/D converter (Axon Instrument). Leak currents were subtracted using a P/+4 for L-type currents or a P/–6 for T-type currents.

Figure 4:
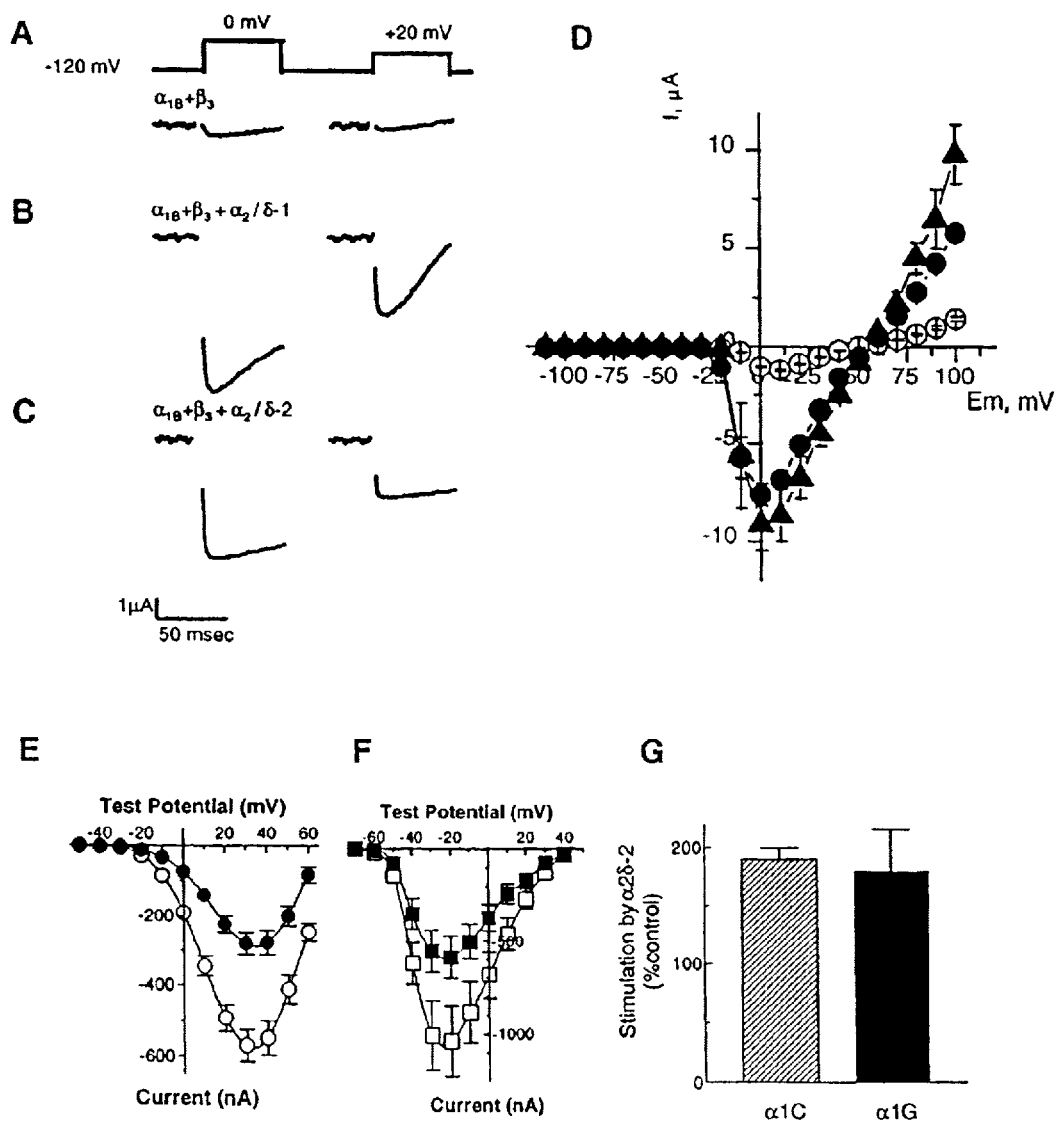
FIG. 4 provides data obtained from Xenopus oocyte expression system tests. Panel A provides representative records of barium currents evoked by step depolarization from −120 to 0 mV and +20 mV, for oocytes injected with cRNA encoding $\alpha_1B+\beta3$, while Panel B provides results for oocytes injected with cRNA encoding $\alpha_1B+\beta3+\alpha_2\delta-1$, and Panel C provides results for oocytes injected with cRNA encoding $\alpha_1B+\beta3+\alpha_2\delta-2$. Panel D provides mean current-voltage curves from two independent injections (mean±EM), with $\alpha_1B+\delta3$ (open circles), $\alpha_1B+\delta3+\alpha_2\delta-1$ (filled triangles), and $\alpha_1B+\delta3+\alpha_2\delta-2$ (filled circle) combinations. Panel E provides current-voltage relationships of $\alpha1C$ alone (filled circles) and $\alpha1C/\alpha2\delta-2$ (circles) induced currents. Panel F provides current-voltage relationships of $\alpha1G$ (filled squares) and $\alpha1G/\alpha2\delta-2$ (squares) induced currents. Panel G provides the average stimulation of $\alpha1C$ and $\alpha1G$ currents by co-expression with $\alpha_2\delta-2$.

Injection of oocytes with cRNA encoding the pore-forming human $\alpha 1B$ subunit together with an auxiliary $\beta 3$ subunit resulted in expression of functional N-type calcium channels in oocyte plasma membranes with a peak current of $1.0\pm 0.1$ $\mu A$ (n=4) (See, FIG. 4A). Channel activity was indicated as representative inward barium currents observed in response to 0 mV and +20 mV test potentials. The magnitude of N-type currents was increased 9 fold to $9.1\pm 1.4$ $\mu A$ (n=10) when $\alpha 1B$ and $\beta 3$ were co-expressed with the rabbit skeletal muscle $\alpha_2\delta$-1 subunit (See, FIG. 4B). When co-expressed with $\alpha 1B$ and $\beta_3$ subunits, the $\alpha_2\delta$-2 subunit exerted a similar effect on N-type channel expression, increasing peak current size to $7.6\pm 0.6$ $\mu A$ (n=10)(See, FIG. 4C). No channel activity was observed after injection of $\alpha_2\delta$-2 cRNA alone (data not shown). By varying the test potential in the range from $-100$ mV to $+100$ mV it was established that the shape and position of current-voltage (IV) relationships were similar for all 3 subunit combinations, with the maximum current at 0 mV test potential and reversal potential at +50 mV (See, FIG. 4D).

Stimulation of N-type current expression by $\alpha_2\delta$-1 and $\alpha_2\delta$-2 subunits (FIGS. 4A–C) is similar to the previously described effect of $\alpha_2\delta$-1 on P/Q-type $Ca^{2+}$ channels formed by $\alpha 1A$ and $\beta$ subunits (De Waard and Campbell, Neuron 16(2):431–400 [1996]; and Walker and De Waard, Trends Neurosci., 21(4):148–154 [1998]), which has been shown to depend on $\alpha_2\delta$-1 subunit glycosylation (Gumett et al., supra). Thus, it is likely that $\alpha_2\delta$-2 subunit is glycosylated when expressed in Xenopus oocytes, as is expected from biochemical and sequence analysis. Noticeably, the $\alpha_2\delta$-1, but not the $\alpha_2\delta$-2 subunit was able to hasten N-type $Ca^{2+}$ channel inactivation. Indeed, at the end of a 50 ms test pulse to +20 mV, the size of the current was reduced to $33\pm 10\%$ (n=8) of the peak current for $\alpha 1B+\beta_3+\alpha_2\delta$-1, to $59\pm 5\%$ (n=24) of the peak current for $\alpha 1B+\beta_3+\alpha_2\delta$-2 and to $51\pm 4\%$ (n=15) of the peak current for $\alpha 1B+\beta_3$ subunit combinations.

To test for an $\alpha_2\delta$-2 effect on L-type channels, either $\alpha 1C$ cRNA alone, or $\alpha 1C$ plus $\alpha_2\delta$-2 cRNA were injected into oocytes. Peak currents measured during a series of test potentials were averaged (See, FIG. 4E). The results shown in Panel E correspond to experiments in which currents were evoked by a series of test pulses of −50 mV to +70 mV from a holding potential of −70 mV in 40 mM $Ba^{2+}$ solution. Average α1C currents were collected from 33 oocytes, α1C/α2δ-2 currents were from 31 oocytes isolated from three different frogs. Data represent mean ±SEM. The results shown in Panel F correspond to experiments in which currents were elicited by test pulses of −70 mV to +50 mV from a holding potential of −90 mV in 10 mM $Ba^{2+}$ solution. Average α1G currents were collected from 33 oocytes, α1G/α2δ-2 currents were from 32 oocytes isolated from four frogs. Panel G provides the average stimulation of α1C and α1G currents by co-expression with $α_2δ$-2. When peak current amplitudes measured at +30 mV were compared, α1C/$α_2δ$-2 currents were significantly larger than α1C by 201% (t-test, $P<0.001$). However, there were no significant differences in the position of the IV curves, which peaked at ∼+35 mV. Similar to the $α_2δ$-2 effect on α1C channels, co-injection of $α_2δ$-2 cRNA with α1G cRNA increased T-type current amplitudes by 176% (t-test, $P<0.05$), compared to α1G alone.

There were no significant differences in their biophysical properties including activation threshold, position of their IV curves, reversal potentials, and activation and inactivation kinetics. Based upon these experiments, it appears that the cloned $α_2δ$-2 protein is able to function as an auxiliary subunit of all three subfamilies of voltage-gated $Ca^{2+}$ channels. Since expression of the cloned T-type channels was found to be highly variable between batches of oocytes, each batch was injected with both α1 and α1α2δ-2. Stimulation by α2δ-2 was measured for each batch, then averaged.

Example 11

In vitro and in vivo Growth Suppression of Tumor Cell Growth

It is the inventors' consideration that the $α_2δ$ gene by virtue of its location in the critical cancer region on human chromosome 3p21.3 and its association with small cell lung carcinoma in patients with Lambert-Eton syndrome is a strong candidate tumor suppressor gene that is involved in the causation of lung cancer and in the development of several common human malignancies including, but not limited to, lung, breast, cervical, head and neck carcinomas. The tumor growth suppression function of the $α_2δ$ subunit is analyzed using either constitutively expressed $α_2δ$ subunit or tet-controlled expression vectors which contain DNA sequences that encode at least a portion of isoform I or isoform II and which express the DNA sequences in the presence of tetracycline, as described supra (Example 9). The constitutively expressing vectors or tet-controlled vectors are transfected into lung cancer and nasopharyngeal carcinoma cells (Example 9) and the transfected cells are used to determine the effect of expression of $α_2δ$ subunits on growth of the transformed tumor cells both in vitro and in vivo.

The effect on tumor cell growth of the constitutively expressing vectors or in the presence and absence of tetracycline is assessed in vitro under cell culture conditions and in vivo by measuring tumor formation and/or growth rate in nude or SCID mice. The function of the $α_2δ$ gene as a tumor suppressor gene is determined by observing an increased rate of cell growth of transfected cancer cells in vitro in the presence either of a control vector transfected cell or of tetracycline as compared to the rate of cell growth in the absence of tetracycline. The tumor suppressor function of the $α_2δ$ gene is also confirmed in vivo by the observation that the number and/or rate of tumor formation by the transfected tumor cells in nude mice is increased in the presence or absence of tetracycline as compared to that in the presence or absence of tetracycline for tumor cells transfected with the Tet regulatable system. In the constitutively expressing system, the tumor growth rate or number is compared for tumors arising from tumor cells transfected with either the control vector or the control vector which contains a specifically constructed inactive mutant form of the $α_2δ$ gene.

Example 12

Generation of Knockout Mice by Targeted Inactivation of the $α_2δ$ Subunit Gene

Knockout mice which do not contain a functional murine orthologous $α_2δ$ gene are generated as follows. The mouse ESTs (GenBank Accession ## AA000341 and AA08996) which the inventors identified as representing sequences of the murine orthologous $α_2δ$ gene were used to screen a phage genomic library made from mouse stem cells (ES). An overlapping phage contig (about 25 kb in size) containing several exons from the carboxy terminus of the mouse gene and part of the 3' UTR was assembled and used in the construction work. Using methods known in the art, a targeting vector containing this portion of the murine ortholog of the human $α_2δ$ gene interrupted by a neo positive selection cassette is constructed. This vector is electroporated into mouse 129SVJ embryonic stem cells and the targeted DNA is integrated in a site-specific manner by homologous recombination. The targeted ES cells are injected into mouse blastocysts and placed into a pseudopregnant female for production of heterozygous mice. These mice are used for production of homozygous null mice by interbreeding and screening the progeny for the presence of the $α_2δ$ gene. Heterozygous and homozygous transgenic knockout mice are used in carcinogenesis studies (e.g., to determine whether there is a change in tumor incidence and/or growth rate compared to wild-type mice). Tumor development in multiple tissues is monitored and animals are sacrificed to remove and evaluate tumors for size, location and histology. The heterozygous and homozygous transgenic knockout mice are also used to evaluate development of neurological and cardiovascular pathology using methods well known in the art.

From the above, it is clear that the invention provides calcium channel alpha2delta ($α_2δ$) subunits and nucleic acid sequences encoding them. These compositions are useful in methods for identifying compounds that modulate the activity of calcium channels and for identifying compounds as therapeutic for disease.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and in fields related thereto are intended to be within the scope of the invention.

What is claimed is:

1. A substantially purified calcium channel protein comprising an amino acid sequence selected from the group consisting of:
   (a) SEQ ID NO: 2;
   (b) SEQ ID NO: 6; and
   (c) sequences having at least 95% sequence identity to (a) or (b);
   wherein the calcium channel protein potentiates activity of voltage-gated channels.

2. The calcium channel protein of claim 1, wherein the protein is part of a fusion protein.

3. The calcium channel protein of claim 2, wherein said fusion protein comprises a polypeptide selected from the group consisting of chloramphenicol acyltransferase, luciferase, beta-galactosidase, protein A, glutathione-S-transferase, and polyhistidine.

4. The calcium channel protein of claim 1, wherein the amino acid sequence comprises the amino acid sequence as set forth in SEQ ID NO: 2.

5. The calcium channel protein of claim 1, wherein the amino acid sequence comprises the amino acid sequence as set forth in SEQ ID NO: 6.

6. A substantially purified calcium channel protein encoded by a nucleic acid sequence selected from the group consisting of(a) SEQ ID NO: 1 and (b) SEQ ID NO: 3 and (c) SEQ ID NO: 5.

* * * * *

UNITED STATES PATENT AND TRADEMARK OFFICE
CERTIFICATE OF CORRECTION

PATENT NO. : 6,979,724 B2      Page 1 of 4
APPLICATION NO. : 10/116949
DATED : December 27, 2005
INVENTOR(S) : Lerman et al.

It is certified that error appears in the above-identified patent and that said Letters Patent is hereby corrected as shown below:

Title Page, Under Other Publications (Item (56):

Page 1, Right column, "Wells. J.A." should be --Wells, J.A.--

Page 2, Left column (Herin *et al.*), "Ca2+" should be --$Ca^{2+}$--

Page 3, Left column (Estacion and Mordan), "365" should be --366--

Page 3, Left column (Burnett *et al.*), "431-400" should be --431-40--

Page 4, Left column (Qin *et al.*), "$\alpha_{2\delta\text{-subunit}}$" should be --$\alpha_2\delta$-subunit--

In the Specification:

Column 2, Line 62, "F1AG" should be --FLAG--

Column 3, Line 21, "prefer-red" should be --preferred--

Column 6, Line 40, "$\delta_2\delta$-2" should be --$\alpha_2\delta$-2--

Column 6, Line 42, "$\delta_2\delta$-2" should be --$\alpha_2\delta$-2--

Column 6, Line 50, "$\alpha 2\delta$-1" should be --$\alpha_2\delta$-1--

Column 6, Line 54, "$\delta 3$" should be --$\beta 3$--

Column 6, Line 54, "$\delta 3$" should be --$\beta 3$--

Column 6, Line 54, "$\alpha 2\delta$" should be --$\alpha_2\delta$--

Column 6, Line 55, "$\delta 3$" should be --$\beta 3$--

Column 6, Line 57, "$\alpha 2\delta$" should be --$\alpha_2\delta$--

Column 6, Line 59, "$\alpha 2\delta$" should be --$\alpha_2\delta$--

Column 9, Line 44, "is the to be equivalent" should be --is said to be equivalent--

Column 10, Line 17, "mRNA" should be --hnRNA--

Column 12, Line 48, "$\delta_2\delta$" should be --$\alpha_2\delta$--

Column 12, Line 49, "$\delta_2\delta$" should be --$\alpha_2\delta$--

Column 13, Line 10, "$\beta_2\delta$-1" should be --$\alpha_2\delta$-1--

Column 13, Line 21, "$\delta$" should be --$\beta$--

UNITED STATES PATENT AND TRADEMARK OFFICE
CERTIFICATE OF CORRECTION

PATENT NO.        : 6,979,724 B2
APPLICATION NO.   : 10/116949
DATED             : December 27, 2005
INVENTOR(S)       : Lerman et al.

It is certified that error appears in the above-identified patent and that said Letters Patent is hereby corrected as shown below:

Column 13, Line 22, "$\delta_2$" should be --$\beta_2$--

Column 13, Line 25, "$2\delta_2$" should be --$2\beta_2$--

Column 13, Line 55, "a1" should be --$\alpha 1$--

Column 14, Line 4, "$\delta_3$" should be --$\beta_3$--

Column 14, Line 6, "$\delta$" should be --$\beta$--

Column 14, Line 8, "$\delta$" should be --$\beta$--

Column 14, Line 13, "$\delta_2\delta$" should be --$\alpha_2\delta$--

Column 14, Line 34, "$\delta_2\delta$-2" should be --$\alpha_2\delta$-2--

Column 14, Line 35, "$\delta_2\delta$-2" should be --$\alpha_2\delta$-2--

Column 15, Line 18, "O'Neill et all.," should be --O'Neill et al.,--

Column 15, Line 24, "146701474" should be --1467-1474--

Column 16, Line 27, "$\alpha_2\delta,\beta$" should be --$\alpha_2\delta$, $\beta$--

Column 16, Line 27, "$\gamma$subunits" should be --$\gamma$ subunits--

Column 16, Line 38, "$\alpha_2,\beta,\gamma$" should be --$\alpha_2$, $\beta$, $\gamma$--

Column 17, Line 1, "a1" should be --$\alpha 1$--

Column 17, Line 45, "$\delta$" should be --$\beta$--

Column 18, Line 5, "$\delta$" should be --$\beta$--

Column 19, Line 4, "is different" should be --is a different--

Column 20, Line 5, "are the to be "PCR" should be --are said to be "PCR--

Column 20, Line 59, "), be" should be --), or be--

Column 21, Line 33, "(IL-12),interferon" should be --(IL-12), interferon--

Column 27, Line 24, "with$\alpha_1,\beta$" should be --with $\alpha_1$, $\beta$--

Column 30, Line 9, "[Harpold et al. supra]" should be --(Harpold et al., supra.)--

Column 30, Line 36, "unla-belled A" should be --un-labelled A--

Column 32, Line 24, "etc. In" should be --etc.). In--

Column 34, Line 63, "lung testis" should be --lung, testis--

UNITED STATES PATENT AND TRADEMARK OFFICE
CERTIFICATE OF CORRECTION

PATENT NO.       : 6,979,724 B2
APPLICATION NO.  : 10/116949
DATED            : December 27, 2005
INVENTOR(S)      : Lerman et al.

It is certified that error appears in the above-identified patent and that said Letters Patent is hereby corrected as shown below:

Column 35, Line 36, "lung testis" should be --lung, testis--

Column 39, Line 1, "supra]" should be --supra)--

Column 39, Line 62, "$\alpha_2\delta 2$" should be --$\alpha_2\delta$-2--

Column 39, Line 64, "#284494" should be --#284494)--

Column 41, Line 5, "Iuf." should be --Inf.--

Column 41, Line 45, "$\delta_2\delta$" should be --$\alpha_2\delta$--

Column 41, Line 53, "$\delta_2\delta$" should be --$\alpha_2\delta$--

Column 41, Line 67, "$\delta_2\delta$" should be --$\alpha_2\delta$--

Column 42, Line 7, "$\delta_2\delta$" should be --$\alpha_2\delta$--

Column 42, Line 13, "$\delta_2\delta$-2" should be --$\alpha_2\delta$-2--

Column 42, Line 18, "$\delta_2\delta$" should be --$\alpha_2\delta$--

Column 42, Line 24, "$\delta_2\delta$" should be --$\alpha_2\delta$--

Column 42, Line 39, "$\delta_2\delta$" should be --$\alpha_2\delta$--

Column 42, Line 43, "$\delta_2\delta$" should be --$\alpha_2\delta$--

Column 42, Line 44, "supra;" should be --supra);--

Column 42, Line 44, "Interestingly" should be --interestingly--

Column 42, Line 51, "$\delta_2\delta$" should be --$\alpha_2\delta$--

Column 42, Line 61, "$\delta_2\delta$" should be --$\alpha_2\delta$--

Column 43, Line 17, "( residues" should be --(residues--

Column 43, Line 18, "1)" should be --I)--

Column 43, Line 19, "(alpha$_2$)" should be --(alpha)$_2$--

Column 44, Line 41, "$A^+RNA$" should be --A+RNA--

Column 44, Line 62, "carcinomas. (NCBI" should be --carcinomas (NCBI--

Column 44, Line 62, "database," should be --databases).--

Column 44, Line 63, "$\delta_2\delta$" should be --$\alpha_2\delta$--

UNITED STATES PATENT AND TRADEMARK OFFICE
CERTIFICATE OF CORRECTION

PATENT NO. : 6,979,724 B2
APPLICATION NO. : 10/116949
DATED : December 27, 2005
INVENTOR(S) : Lerman et al.

It is certified that error appears in the above-identified patent and that said Letters Patent is hereby corrected as shown below:

Column 44, Line 67, "$\delta_2\delta$" should be --$\alpha_2\delta$--

Column 45, Line 2, "$\delta_2\delta$" should be --$\alpha_2\delta$--

Column 46 & 47 (Title of Table 1), "$\alpha\ 2\ \delta$" should be --$\alpha_2\delta$--

Column 47, Line 59, "was" should be --were--

Column 48, Line 67, "[32P]" should be --$[^{32}P]$--

Column 49 (Title of Table 2), "a2d-2" should be --$\alpha_2\delta$-2--

Column 51, Line 66, "(alpha$_2$)" should be --(alpha)$_2$--

Column 52, Line 6, "(alpha$_2$)" should be --(alpha)$_2$--

Column 53, Line 63, "was-120 mV." should be --was -120 mV.--

Column 54, Line 53, "431-400" should be --431-40--

Column 55, Line 6, "$\alpha 2\delta$-2" should be --$\alpha_2\delta$-2--

Column 55, Line 12, "$\alpha 2\delta$-2" should be --$\alpha_2\delta$-2--

Column 55, Line 31, "$\alpha 1\alpha 2\delta$-2" should be --$\alpha_1\alpha_2\delta$-2--

Column 55, Line 32, "$\alpha 2\delta$-2" should be --$\alpha_2\delta$-2--

Signed and Sealed this

Fourteenth Day of July, 2009

JOHN DOLL
*Acting Director of the United States Patent and Trademark Office*

SEQUENCE LISTING

<160> NUMBER OF SEQ ID NOS: 114

<210> SEQ ID NO 1
<211> LENGTH: 5463
<212> TYPE: DNA
<213> ORGANISM: Homo sapiens
<220> FEATURE:
<221> NAME/KEY: CDS
<222> LOCATION: (162)..(3599)

<400> SEQUENCE: 1

```
gccagcgctg cagggagata gcagcgcgca gcccgcagag gcgctgcggc ccgtgcagcc      60
ccggaggccc ctcgcggaga aggcggcggc ggaggagagg ccgagttacc gcccgccgcc     120
cgcgcccccc ctccccgcgg cgccgcatct tgaatggaaa c atg gcg gtg ccg gct    176
                                              Met Ala Val Pro Ala
                                                1               5 cgg acc tgc ggc gcc tct cgg ccc ggc cca gcg cgg act gcg cgc ccc       224
Arg Thr Cys Gly Ala Ser Arg Pro Gly Pro Ala Arg Thr Ala Arg Pro
             10                  15                  20 tgg ccc ggc tgc ggc ccc cac cct ggc ccc ggc acc cgg gcc ccg acg       272
Trp Pro Gly Cys Gly Pro His Pro Gly Pro Gly Thr Arg Ala Pro Thr
 25                  30                  35 tcc ggg ccc ccg cgc ccg ctg tgg ctg ctg ctg ccg ctt cta ccg ctg       320
Ser Gly Pro Pro Arg Pro Leu Trp Leu Leu Leu Pro Leu Leu Pro Leu
         40                  45                  50 ctc gcc gcc ccc ggc gcc tct gcc tac agc ttc ccc cag cag cac acg       368
Leu Ala Ala Pro Gly Ala Ser Ala Tyr Ser Phe Pro Gln Gln His Thr
 55                  60                  65 atg cag cac tgg gcc cgg cgt ctg gag cag gag gtc gac ggc gtg atg       416
Met Gln His Trp Ala Arg Arg Leu Glu Gln Glu Val Asp Gly Val Met
 70                  75                  80                  85 cgg att ttt gga ggc gtc cag cag ctc cgt gag att tac aag gac aac       464
Arg Ile Phe Gly Gly Val Gln Gln Leu Arg Glu Ile Tyr Lys Asp Asn
                 90                  95                 100 cgg aac ctg ttc gag gta cag gag aat gag cct cag aag ttg gtg gag       512
Arg Asn Leu Phe Glu Val Gln Glu Asn Glu Pro Gln Lys Leu Val Glu
             105                 110                 115 aag gtg gca ggg gac att gag agc ctt ctg gac agg aag gtg cag gcc       560
Lys Val Ala Gly Asp Ile Glu Ser Leu Leu Asp Arg Lys Val Gln Ala
         120                 125                 130 ctg aag aga ctg gct gat gct gca gag aac ttc cag aaa gca cac cgc       608
Leu Lys Arg Leu Ala Asp Ala Ala Glu Asn Phe Gln Lys Ala His Arg
 135                 140                 145 tgg cag gac aac atc aag gag gaa gac atc gtg tac tat gac gcc aag       656
Trp Gln Asp Asn Ile Lys Glu Glu Asp Ile Val Tyr Tyr Asp Ala Lys
150                 155                 160                 165 gct gac gct gag ctg gac gac cct gag agt gag gat gtg gaa agg ggg       704
Ala Asp Ala Glu Leu Asp Asp Pro Glu Ser Glu Asp Val Glu Arg Gly
                 170                 175                 180 tct aag gcc agc acc cta agg ctg gac ttc atc gag gac cca aac ttc       752
Ser Lys Ala Ser Thr Leu Arg Leu Asp Phe Ile Glu Asp Pro Asn Phe
             185                 190                 195 aag aac aag gtc aac tat tca tac gcg gct gta cag atc cct acg gac       800
Lys Asn Lys Val Asn Tyr Ser Tyr Ala Ala Val Gln Ile Pro Thr Asp
         200                 205                 210 atc tac aaa ggc tcc act gtc atc ctc aat gag ctc aac tgg aca gag       848
Ile Tyr Lys Gly Ser Thr Val Ile Leu Asn Glu Leu Asn Trp Thr Glu
 215                 220                 225
```

```
gcc ctg gag aat gtg ttc atg gaa aac cgc aga caa gac ccc aca ctg     896
Ala Leu Glu Asn Val Phe Met Glu Asn Arg Arg Gln Asp Pro Thr Leu
230                 235                 240                 245 ctg tgg cag gtc ttc ggc agc gcc aca gga gtc act cgc tac tac ccg     944
Leu Trp Gln Val Phe Gly Ser Ala Thr Gly Val Thr Arg Tyr Tyr Pro
            250                 255                 260 gcc acc ccg tgg cga gcc ccc aag aag atc gac ctg tac gat gtc cga     992
Ala Thr Pro Trp Arg Ala Pro Lys Lys Ile Asp Leu Tyr Asp Val Arg
        265                 270                 275 agg aga ccc tgg tat atc cag ggg gcc tcg tca ccc aaa gac atg gtc    1040
Arg Arg Pro Trp Tyr Ile Gln Gly Ala Ser Ser Pro Lys Asp Met Val
    280                 285                 290 atc atc gtg gat gtg agt ggc agt gtg agc ggc ctg acc ctg aag ctg    1088
Ile Ile Val Asp Val Ser Gly Ser Val Ser Gly Leu Thr Leu Lys Leu
295                 300                 305 atg aag aca tct gtc tgc gag atg ctg gac acg ctg tct gat gat gac    1136
Met Lys Thr Ser Val Cys Glu Met Leu Asp Thr Leu Ser Asp Asp Asp
310                 315                 320                 325 tat gtg aat gtg gcc tcg ttc aac gag aag gca cag cct gtg tca tgc    1184
Tyr Val Asn Val Ala Ser Phe Asn Glu Lys Ala Gln Pro Val Ser Cys
                330                 335                 340 ttc aca cac ctg gtg cag gcc aat gtg cgc aac aag aag gtg ttc aag    1232
Phe Thr His Leu Val Gln Ala Asn Val Arg Asn Lys Lys Val Phe Lys
            345                 350                 355 gaa gct gtg cag ggc atg gtg gcc aag ggc acc aca ggc tac aag gcc    1280
Glu Ala Val Gln Gly Met Val Ala Lys Gly Thr Thr Gly Tyr Lys Ala
        360                 365                 370 ggc ttt gag tat gcc ttt gac cag ctg cag aac tcc aac atc act cgg    1328
Gly Phe Glu Tyr Ala Phe Asp Gln Leu Gln Asn Ser Asn Ile Thr Arg
    375                 380                 385 gcc aac tgc aac aag atg atc atg atg ttc acg gat ggt ggt gag gac    1376
Ala Asn Cys Asn Lys Met Ile Met Met Phe Thr Asp Gly Gly Glu Asp
390                 395                 400                 405 cgc gtg cag gac gtc ttt gag aag tac aat tgg cca aac cgg acg gtg    1424
Arg Val Gln Asp Val Phe Glu Lys Tyr Asn Trp Pro Asn Arg Thr Val
                410                 415                 420 cgc gtg ttt act ttc tcc gtg ggg cag cat aac tat gac gtc aca ccg    1472
Arg Val Phe Thr Phe Ser Val Gly Gln His Asn Tyr Asp Val Thr Pro
            425                 430                 435 ctg cag tgg atg gcc tgt gcc aac aaa ggc tac tat ttt gag atc cct    1520
Leu Gln Trp Met Ala Cys Ala Asn Lys Gly Tyr Tyr Phe Glu Ile Pro
        440                 445                 450 tcc atc gga gcc atc cgc atc aac aca cag gaa tat cta gat gtg ttg    1568
Ser Ile Gly Ala Ile Arg Ile Asn Thr Gln Glu Tyr Leu Asp Val Leu
455                 460                 465 ggc agg ccc atg gtg ctg gca ggc aag gag gcc aag cag gtt cag tgg    1616
Gly Arg Pro Met Val Leu Ala Gly Lys Glu Ala Lys Gln Val Gln Trp
470                 475                 480                 485 acc aac gtg tat gag gat gca ctg gga ctg ggg ttg gtg gta aca ggg    1664
Thr Asn Val Tyr Glu Asp Ala Leu Gly Leu Gly Leu Val Val Thr Gly
                490                 495                 500 acc ctc cct gtt ttc aac ctg aca cag gat ggc cct ggg gaa aag aag    1712
Thr Leu Pro Val Phe Asn Leu Thr Gln Asp Gly Pro Gly Glu Lys Lys
            505                 510                 515 aac cag ctg atc ctg ggc gtg atg ggc att gac gtg gct ctg aat gac    1760
Asn Gln Leu Ile Leu Gly Val Met Gly Ile Asp Val Ala Leu Asn Asp
        520                 525                 530 atc aag agg ctg acc ccc aac tac acg ctt gga gcc aac ggc tat gtg    1808
Ile Lys Arg Leu Thr Pro Asn Tyr Thr Leu Gly Ala Asn Gly Tyr Val
    535                 540                 545
```

-continued

| | |
|---|---|
| ttt gcc att gac ctg aac ggc tac gtg ttg ctg cac ccc aat ctc aag<br>Phe Ala Ile Asp Leu Asn Gly Tyr Val Leu Leu His Pro Asn Leu Lys<br>550                       555                     560                    565 | 1856 |
| ccc cag acc acc aac ttc cgg gag cct gtg act ctg gac ttc ctg gat<br>Pro Gln Thr Thr Asn Phe Arg Glu Pro Val Thr Leu Asp Phe Leu Asp<br>                    570                     575                    580 | 1904 |
| gcg gag cta gag gat gag aac aag gaa gag atc cgt cgg agc atg att<br>Ala Glu Leu Glu Asp Glu Asn Lys Glu Glu Ile Arg Arg Ser Met Ile<br>              585                     590                    595 | 1952 |
| gat ggc aac aag ggc cac aag cag atc aga acg ttg gtc aag tcc ctg<br>Asp Gly Asn Lys Gly His Lys Gln Ile Arg Thr Leu Val Lys Ser Leu<br>600                       605                     610 | 2000 |
| gat gag agg tac ata gat gag gtg aca cgg aac tac acc tgg gtg cct<br>Asp Glu Arg Tyr Ile Asp Glu Val Thr Arg Asn Tyr Thr Trp Val Pro<br>              615                     620                    625 | 2048 |
| ata agg agc act aac tac agc ctg ggg ctg gtg ctc cca ccc tac agc<br>Ile Arg Ser Thr Asn Tyr Ser Leu Gly Leu Val Leu Pro Pro Tyr Ser<br>630                       635                     640                    645 | 2096 |
| acc ttc tac ctc caa gcc aat ctc agt gac cag atc ctg cag gtc aag<br>Thr Phe Tyr Leu Gln Ala Asn Leu Ser Asp Gln Ile Leu Gln Val Lys<br>              650                     655                    660 | 2144 |
| tat ttt gag ttc ctg ctc ccc agc agc ttt gag tct gaa gga cac gtt<br>Tyr Phe Glu Phe Leu Leu Pro Ser Ser Phe Glu Ser Glu Gly His Val<br>                    665                     670                    675 | 2192 |
| ttc att gct ccc aga gag tac tgc aag gac ctg aat gcc tca gac aac<br>Phe Ile Ala Pro Arg Glu Tyr Cys Lys Asp Leu Asn Ala Ser Asp Asn<br>              680                     685                    690 | 2240 |
| aac acc gag ttc ctg aaa aac ttt att gag ctc atg gag aaa gtg act<br>Asn Thr Glu Phe Leu Lys Asn Phe Ile Glu Leu Met Glu Lys Val Thr<br>695                       700                     705 | 2288 |
| cca gac tcc aag cag tgc aac aac ttc ctt ctg cac aac ctg atc ttg<br>Pro Asp Ser Lys Gln Cys Asn Asn Phe Leu Leu His Asn Leu Ile Leu<br>710                       715                     720                    725 | 2336 |
| gac acg ggc atc acg cag cag ctg gta gag cgt gtg tgg agg gac cag<br>Asp Thr Gly Ile Thr Gln Gln Leu Val Glu Arg Val Trp Arg Asp Gln<br>                    730                     735                    740 | 2384 |
| gat ctc aac acg tac agc cta ctg gcc gtg ttc gct gcc aca gac ggt<br>Asp Leu Asn Thr Tyr Ser Leu Leu Ala Val Phe Ala Ala Thr Asp Gly<br>              745                     750                    755 | 2432 |
| ggc atc acc cga gtc ttc ccc aac aag gca gct gag gac tgg aca gag<br>Gly Ile Thr Arg Val Phe Pro Asn Lys Ala Ala Glu Asp Trp Thr Glu<br>            760                     765                    770 | 2480 |
| aac cct gag ccc ttc aat gcc agc ttc tac cgc cgc agc ctg gat aac<br>Asn Pro Glu Pro Phe Asn Ala Ser Phe Tyr Arg Arg Ser Leu Asp Asn<br>775                       780                     785 | 2528 |
| cac ggt tat gtc ttc aag ccc cca cac cag gat gcc ctg tta agg ccg<br>His Gly Tyr Val Phe Lys Pro Pro His Gln Asp Ala Leu Leu Arg Pro<br>790                       795                     800                    805 | 2576 |
| ctg gag ctg gag aat gac act gtg ggc atc ctc gtc agc aca gct gtg<br>Leu Glu Leu Glu Asn Asp Thr Val Gly Ile Leu Val Ser Thr Ala Val<br>                    810                     815                    820 | 2624 |
| gag ctc agc cta ggc agg cgc aca ctg agg cca gca gtg gtg ggc gtc<br>Glu Leu Ser Leu Gly Arg Arg Thr Leu Arg Pro Ala Val Val Gly Val<br>              825                     830                    835 | 2672 |
| aag ctg gac cta gag gct tgg gct gag aag ttc aag gtg cta gcc agc<br>Lys Leu Asp Leu Glu Ala Trp Ala Glu Lys Phe Lys Val Leu Ala Ser<br>            840                     845                    850 | 2720 |
| aac cgt acc cac caa gac cag cct cag aag tgc ggc ccc aac agc cac<br>Asn Arg Thr His Gln Asp Gln Pro Gln Lys Cys Gly Pro Asn Ser His | 2768 |

-continued

```
            855                 860                 865
tgt gag atg gac tgc gag gtt aac aat gag gac tta ctc tgt gtc ctc        2816
Cys Glu Met Asp Cys Glu Val Asn Asn Glu Asp Leu Leu Cys Val Leu
870                 875                 880                 885 att gat gat gga gga ttc ctg gtg ctg tca aac cag aac cat cag tgg        2864
Ile Asp Asp Gly Gly Phe Leu Val Leu Ser Asn Gln Asn His Gln Trp
            890                 895                 900 gac cag gtg ggc agg ttc ttc agt gag gtg gat gcc aac ctg atg ctg        2912
Asp Gln Val Gly Arg Phe Phe Ser Glu Val Asp Ala Asn Leu Met Leu
        905                 910                 915 gca ctc tac aat aac tcc ttc tac acc cgc aag gag tcc tat gac tat        2960
Ala Leu Tyr Asn Asn Ser Phe Tyr Thr Arg Lys Glu Ser Tyr Asp Tyr
    920                 925                 930 cag gca gcc tgt gcc cct cag ccc cct ggc aac ctg ggt gct gca ccc        3008
Gln Ala Ala Cys Ala Pro Gln Pro Pro Gly Asn Leu Gly Ala Ala Pro
935                 940                 945 cgg ggt gtc ttt gtg ccc acc gtt gca gat ttc ctt aac ctg gcc tgg        3056
Arg Gly Val Phe Val Pro Thr Val Ala Asp Phe Leu Asn Leu Ala Trp
950                 955                 960                 965 tgg acc tct gct gcc gcc tgg tcc ctg ttc cag cag ctt ctc tac ggc        3104
Trp Thr Ser Ala Ala Ala Trp Ser Leu Phe Gln Gln Leu Leu Tyr Gly
            970                 975                 980 ctc atc tac cac agc tgg ttc caa gca gac ccc gcg gag gcc gag ggg        3152
Leu Ile Tyr His Ser Trp Phe Gln Ala Asp Pro Ala Glu Ala Glu Gly
        985                 990                 995 agc ccc gag acg cgc gag agc agc tgc gtc atg aaa cag acc cag tac        3200
Ser Pro Glu Thr Arg Glu Ser Ser Cys Val Met Lys Gln Thr Gln Tyr
    1000                1005                1010 tac ttc ggc tcg gta aac gcc tcc tac aac gcc atc atc gac tgc gga        3248
Tyr Phe Gly Ser Val Asn Ala Ser Tyr Asn Ala Ile Ile Asp Cys Gly
1015                1020                1025 aac tgc tcc agg ctg ttc cac gcg cag aga ctg acc aac acc aat ctt        3296
Asn Cys Ser Arg Leu Phe His Ala Gln Arg Leu Thr Asn Thr Asn Leu
1030                1035                1040                1045 ctc ttt gtg gtg gcc gag aag ccg ctg tgc agc cag tgc gag gct ggc        3344
Leu Phe Val Val Ala Glu Lys Pro Leu Cys Ser Gln Cys Glu Ala Gly
            1050                1055                1060 cgg ctg ctg cag aag gag acg cac tgc cca gcg gac ggc ccg gag cag        3392
Arg Leu Leu Gln Lys Glu Thr His Cys Pro Ala Asp Gly Pro Glu Gln
        1065                1070                1075 tgt gag cta gtg cag aga ccg cga tac cgg aga ggc ccg cac atc tgc        3440
Cys Glu Leu Val Gln Arg Pro Arg Tyr Arg Arg Gly Pro His Ile Cys
    1080                1085                1090 ttc gac tac aac gcg aca gaa gat acc tca gac tgt ggc cgc ggg gcc        3488
Phe Asp Tyr Asn Ala Thr Glu Asp Thr Ser Asp Cys Gly Arg Gly Ala
1095                1100                1105 tcc ttc ccg ccg tcg ctg ggc gtc ctg gtc tcc ctg caa ctg ctg ctc        3536
Ser Phe Pro Pro Ser Leu Gly Val Leu Val Ser Leu Gln Leu Leu Leu
1110                1115                1120                1125 ctc ctg ggc ctg ccg ccc cgg ccg cag cct caa gtc ctc gtc cac gcc        3584
Leu Leu Gly Leu Pro Pro Arg Pro Gln Pro Gln Val Leu Val His Ala
            1130                1135                1140 tct cgc cgc ctc tga gcaccctgcc ccaccccacc tccactccca cctcacccgg        3639
Ser Arg Arg Leu
            1145 cctcttcgcc tttcccaccc tcctgcccca cactcccgc cttagagcct cgtccctccc        3699 tcactgaagg acctgagctg gccaggccct gagagtctgg tctgcgcctt gggatgggga        3759 gtcccaaagc gggacgccgc aggtgtttgg cacccaaatc acatctcacc tccgaactgt        3819
```

-continued

```
tcaagtgtcc ccagaccctt cttgcctgct gggctccccc cagtgggatg ggacagggag      3879
gccacacgca ctggtgccaa accaggcct ctgctgccgc ccttcctgga ggctgcctat       3939
gttggggggg accctgcctc agctgacccg gcctctctgc cccacccaag cccaaacttg      3999
gtttctgtga gaatagtgga ggaaggtgag atggccagtt tgaagcctgt gcctcccagc     4059
ttaaatccta gcaggagaga ggctctgggg cagcccccat gggctcctgc cccttttcagg     4119 cctacagcca catccccaag cccaccaggt gtcaggatag tcacagtgat accagttcag    4179
acactacccc atatacacct ggaacattga ggatggaaac tggactcaca ttcgacatac      4239
cccactgggc acacgcacaa acacacacac tatggggtgg ggtgggtgta ggggcttaca     4299
aagccttaca cagggcgagg ggttggtggg agggttggca cctgcacact ccatctcctg     4359
ctcaccacct gcctctaatc tgagctgcag cctggctggt cctcccatt ctaaagctga      4419 atgtcaaaca gtgccaaatg ctggggcagg gggtgaagaa ccctctgtcc cacccctagc     4479
caccagtgtc ctccaagtgc cccctcacct ctccaggtgc tcattgtaac catttctcac    4539
tagtgtcagg cccccagtgg gaccacatgc cactgcctgc acctttcggc agaggaaccc     4599
ccaccagaca tcacccttg ccttagcagg ggtgactttg tctctcctgg ctgggccatc      4659
cttccgccaa tctggccctt acacactcag gcctgtgccc actccctatc tccttcccac     4719
ccctacacac acactccctg cttgcaggag gccaaactgt ccctcccttg ctgaacacac     4779
acacacacac acacacacag gtggggactg gcacagctc ttcacaccat tcattctggt     4839
catttccccc aaaggcatcc cagcctgggg gccagtgggg aactgagggc aaggggatat     4899
agtgatgggg ctcagatgga ctgggaggag ggggagggtg atgcattaat taatggcttc    4959
gttaattaat gtcatgttgc ttgtcgcttt ctcagtgtgt gtgtgtggtc catgcccact     5019
gctggtgcca gggtgggtgt ccatgtgcac ccggcctgga tgccagctgt gtccttcggg    5079
ggcgtgcgtg taactgtagt gtagtcaggt gctcaatgga gaatataaac atatacagaa     5139
aaatatatat tttaagttta aaaacagaa aaacagacaa acaatcccc atcaggtagc      5199 tgtctaaccc ccagctgggt ctaatccttc tcattaccca cccgacctgg ctgcccctca     5259
ccttgggctg ggggactggg gggccatttc cttttctctg cccttttttt gttgttctat    5319
tttgtacaga caagttggaa aaacaacagc gacaaaaaag tcaagaaact ttgtaaaata    5379
tcgtgtgtgt gattccttgt aaaatatttt caaatggttt attacagaag atcagttatt    5439
aaataatgtt catattttca cttc                                            5463
```

<210> SEQ ID NO 2
<211> LENGTH: 1145
<212> TYPE: PRT
<213> ORGANISM: Homo sapiens

<400> SEQUENCE: 2

```
Met Ala Val Pro Ala Arg Thr Cys Gly Ala Ser Arg Pro Gly Pro Ala
 1               5                  10                  15

Arg Thr Ala Arg Pro Trp Pro Gly Cys Gly Pro His Pro Gly Pro Gly
             20                  25                  30

Thr Arg Arg Pro Thr Ser Gly Pro Pro Arg Pro Leu Trp Leu Leu Leu
         35                  40                  45

Pro Leu Leu Pro Leu Leu Ala Ala Pro Gly Ala Ser Ala Tyr Ser Phe
     50                  55                  60

Pro Gln Gln His Thr Met Gln His Trp Ala Arg Arg Leu Glu Gln Glu
 65                  70                  75                  80
```

```
Val Asp Gly Val Met Arg Ile Phe Gly Val Gln Gln Leu Arg Glu
             85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
            115                 120                 125

Arg Lys Val Gln Ala Leu Lys Arg Leu Ala Asp Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
            195                 200                 205

Gln Ile Pro Thr Asp Ile Tyr Lys Gly Ser Thr Val Ile Leu Asn Glu
210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
    275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
            325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
    355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Phe Thr
385                 390                 395                 400

Asp Gly Gly Glu Asp Arg Val Gln Asp Val Phe Glu Lys Tyr Asn Trp
            405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
            435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495
```

```
Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
            515                 520                 525

Val Ala Leu Asn Asp Ile Lys Arg Leu Thr Pro Asn Tyr Thr Leu Gly
            530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
            565                 570                 575

Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
            595                 600                 605

Leu Val Lys Ser Leu Asp Glu Arg Tyr Ile Asp Glu Val Thr Arg Asn
            610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
            645                 650                 655

Ile Leu Gln Val Lys Tyr Phe Glu Phe Leu Leu Pro Ser Ser Phe Glu
            660                 665                 670

Ser Glu Gly His Val Phe Ile Ala Pro Arg Glu Tyr Cys Lys Asp Leu
            675                 680                 685

Asn Ala Ser Asp Asn Asn Thr Glu Phe Leu Lys Asn Phe Ile Glu Leu
690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
            725                 730                 735

Val Trp Arg Asp Gln Asp Leu Asn Thr Tyr Ser Leu Leu Ala Val Phe
            740                 745                 750

Ala Ala Thr Asp Gly Gly Ile Thr Arg Val Phe Pro Asn Lys Ala Ala
            755                 760                 765

Glu Asp Trp Thr Glu Asn Pro Glu Pro Phe Asn Ala Ser Phe Tyr Arg
            770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
            805                 810                 815

Val Ser Thr Ala Val Glu Leu Ser Leu Gly Arg Arg Thr Leu Arg Pro
            820                 825                 830

Ala Val Val Gly Val Lys Leu Asp Leu Glu Ala Trp Ala Glu Lys Phe
            835                 840                 845

Lys Val Leu Ala Ser Asn Arg Thr His Gln Asp Gln Pro Gln Lys Cys
            850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
            885                 890                 895

Gln Asn His Gln Trp Asp Gln Val Gly Arg Phe Phe Ser Glu Val Asp
            900                 905                 910

Ala Asn Leu Met Leu Ala Leu Tyr Asn Asn Ser Phe Tyr Thr Arg Lys
```

```
                    915                 920                 925
Glu Ser Tyr Asp Tyr Gln Ala Ala Cys Ala Pro Gln Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
        995                 1000                1005

Lys Gln Thr Gln Tyr Tyr Phe Gly Ser Val Asn Ala Ser Tyr Asn Ala
    1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
                1045                1050                1055

Gln Cys Glu Ala Gly Arg Leu Leu Gln Lys Glu Thr His Cys Pro Ala
            1060                1065                1070

Asp Gly Pro Glu Gln Cys Glu Leu Val Gln Arg Pro Arg Tyr Arg Arg
        1075                1080                1085

Gly Pro His Ile Cys Phe Asp Tyr Asn Ala Thr Glu Asp Thr Ser Asp
    1090                1095                1100

Cys Gly Arg Gly Ala Ser Phe Pro Pro Ser Leu Gly Val Leu Val Ser
1105                1110                1115                1120

Leu Gln Leu Leu Leu Leu Gly Leu Pro Pro Arg Pro Gln Pro Gln
                1125                1130                1135

Val Leu Val His Ala Ser Arg Arg Leu
            1140                1145

<210> SEQ ID NO 3
<211> LENGTH: 5482
<212> TYPE: DNA
<213> ORGANISM: Homo sapiens
<220> FEATURE:
<221> NAME/KEY: CDS
<222> LOCATION: (181)..(3618)

<400> SEQUENCE: 3
cgggcagcgc agcccgcaga ggcgctgcgg cccgtgcagc cccggaggcc cctcgcggag      60
aaggcggcgg cggaggagag gccgagttac cgcccgccgc ccgcgccccc ccaaccccgc     120
cgccgccgcc gccgccgcca ctgccccccc tccccgcggc gccgcatctt gaatggaaac     180 atg gcg gtg ccg gct cgg acc tgc ggc gcc tct cgg ccc ggc cca gcg       228
Met Ala Val Pro Ala Arg Thr Cys Gly Ala Ser Arg Pro Gly Pro Ala
 1               5                  10                  15 cgg act gcg cgc ccc tgg ccc ggc tgc ggc ccc cac cct ggc ccc ggc       276
Arg Thr Ala Arg Pro Trp Pro Gly Cys Gly Pro His Pro Gly Pro Gly
             20                  25                  30 acc cgg cgc ccg acg tcc ggg ccc ccg cgc ccg ctg tgg ctg ctg ctg       324
Thr Arg Arg Pro Thr Ser Gly Pro Pro Arg Pro Leu Trp Leu Leu Leu
         35                  40                  45 ccg ctt cta ccg ctg ctc gcc gcc ccc ggc gcc tct gcc tac agc ttc       372
Pro Leu Leu Pro Leu Leu Ala Ala Pro Gly Ala Ser Ala Tyr Ser Phe
     50                  55                  60 ccc cag cag cac acg atg cag cac tgg gcc cgg cgt ctg gag cag gag       420
Pro Gln Gln His Thr Met Gln His Trp Ala Arg Arg Leu Glu Gln Glu
```

-continued

| | | | | | | | | | | | | | | | | |
|---|---|---|---|---|---|---|---|---|---|---|---|---|---|---|---|---|
| | 65 | | | | 70 | | | | | 75 | | | | 80 | | |
| gtc | gac | ggc | gtg | atg | cgg | att | ttt | gga | ggc | gtc | cag | cag | ctc | cgt | gag | 468 |
| Val | Asp | Gly | Val | Met | Arg | Ile | Phe | Gly | Gly | Val | Gln | Gln | Leu | Arg | Glu | |
| | | | | 85 | | | | | 90 | | | | | 95 | | |
| att | tac | aag | gac | aac | cgg | aac | ctg | ttc | gag | gta | cag | gag | aat | gag | cct | 516 |
| Ile | Tyr | Lys | Asp | Asn | Arg | Asn | Leu | Phe | Glu | Val | Gln | Glu | Asn | Glu | Pro | |
| | | | | 100 | | | | | 105 | | | | | 110 | | |
| cag | aag | ttg | gtg | gag | aag | gtg | gca | ggg | gac | att | gag | agc | ctt | ctg | gac | 564 |
| Gln | Lys | Leu | Val | Glu | Lys | Val | Ala | Gly | Asp | Ile | Glu | Ser | Leu | Leu | Asp | |
| | | | | 115 | | | | | 120 | | | | | 125 | | |
| agg | aag | gtg | cag | gcc | ctg | aag | aga | ctg | gct | gat | gct | gca | gag | aac | ttc | 612 |
| Arg | Lys | Val | Gln | Ala | Leu | Lys | Arg | Leu | Ala | Asp | Ala | Ala | Glu | Asn | Phe | |
| | 130 | | | | | 135 | | | | | 140 | | | | | |
| cag | aaa | gca | cac | cgc | tgg | cag | gac | aac | atc | aag | gag | gaa | gac | atc | gtg | 660 |
| Gln | Lys | Ala | His | Arg | Trp | Gln | Asp | Asn | Ile | Lys | Glu | Glu | Asp | Ile | Val | |
| 145 | | | | | 150 | | | | | 155 | | | | | 160 | |
| tac | tat | gac | gcc | aag | gct | gac | gct | gag | ctg | gac | gac | cct | gag | agt | gag | 708 |
| Tyr | Tyr | Asp | Ala | Lys | Ala | Asp | Ala | Glu | Leu | Asp | Asp | Pro | Glu | Ser | Glu | |
| | | | | 165 | | | | | 170 | | | | | 175 | | |
| gat | gtg | gaa | agg | ggg | tct | aag | gcc | agc | acc | cta | agg | ctg | gac | ttc | atc | 756 |
| Asp | Val | Glu | Arg | Gly | Ser | Lys | Ala | Ser | Thr | Leu | Arg | Leu | Asp | Phe | Ile | |
| | | | 180 | | | | | 185 | | | | | 190 | | | |
| gag | gac | cca | aac | ttc | aag | aac | aag | gtc | aac | tat | tca | tac | gcg | gct | gta | 804 |
| Glu | Asp | Pro | Asn | Phe | Lys | Asn | Lys | Val | Asn | Tyr | Ser | Tyr | Ala | Ala | Val | |
| | | | 195 | | | | | 200 | | | | | 205 | | | |
| cag | atc | cct | acg | gac | atc | tac | aaa | ggc | tcc | act | gtc | atc | ctc | aat | gag | 852 |
| Gln | Ile | Pro | Thr | Asp | Ile | Tyr | Lys | Gly | Ser | Thr | Val | Ile | Leu | Asn | Glu | |
| | 210 | | | | | 215 | | | | | 220 | | | | | |
| ctc | aac | tgg | aca | gag | gcc | ctg | gag | aat | gtg | ttc | atg | gaa | aac | cgc | aga | 900 |
| Leu | Asn | Trp | Thr | Glu | Ala | Leu | Glu | Asn | Val | Phe | Met | Glu | Asn | Arg | Arg | |
| 225 | | | | | 230 | | | | | 235 | | | | | 240 | |
| caa | gac | ccc | aca | ctg | ctg | tgg | cag | gtc | ttc | ggc | agc | gcc | aca | gga | gtc | 948 |
| Gln | Asp | Pro | Thr | Leu | Leu | Trp | Gln | Val | Phe | Gly | Ser | Ala | Thr | Gly | Val | |
| | | | | 245 | | | | | 250 | | | | | 255 | | |
| act | cgc | tac | tac | ccg | gcc | acc | ccg | tgg | cga | gcc | ccc | aag | aag | atc | gac | 996 |
| Thr | Arg | Tyr | Tyr | Pro | Ala | Thr | Pro | Trp | Arg | Ala | Pro | Lys | Lys | Ile | Asp | |
| | | | 260 | | | | | 265 | | | | | 270 | | | |
| ctg | tac | gat | gtc | cga | agg | aga | ccc | tgg | tat | atc | cag | ggg | gcc | tcg | tca | 1044 |
| Leu | Tyr | Asp | Val | Arg | Arg | Arg | Pro | Trp | Tyr | Ile | Gln | Gly | Ala | Ser | Ser | |
| | | 275 | | | | | 280 | | | | | 285 | | | | |
| ccc | aaa | gac | atg | gtc | atc | atc | gtg | gat | gtg | agt | ggc | agt | gtg | agc | ggc | 1092 |
| Pro | Lys | Asp | Met | Val | Ile | Ile | Val | Asp | Val | Ser | Gly | Ser | Val | Ser | Gly | |
| | 290 | | | | | 295 | | | | | 300 | | | | | |
| ctg | acc | ctg | aag | ctg | atg | aag | aca | tct | gtc | tgc | gag | atg | ctg | gac | acg | 1140 |
| Leu | Thr | Leu | Lys | Leu | Met | Lys | Thr | Ser | Val | Cys | Glu | Met | Leu | Asp | Thr | |
| 305 | | | | | 310 | | | | | 315 | | | | | 320 | |
| ctg | tct | gat | gat | gac | tat | gtg | aat | gtg | gcc | tcg | ttc | aac | gag | aag | gca | 1188 |
| Leu | Ser | Asp | Asp | Asp | Tyr | Val | Asn | Val | Ala | Ser | Phe | Asn | Glu | Lys | Ala | |
| | | | | 325 | | | | | 330 | | | | | 335 | | |
| cag | cct | gtg | tca | tgc | ttc | aca | cac | ctg | gtg | cag | gcc | aat | gtg | cgc | aac | 1236 |
| Gln | Pro | Val | Ser | Cys | Phe | Thr | His | Leu | Val | Gln | Ala | Asn | Val | Arg | Asn | |
| | | | 340 | | | | | 345 | | | | | 350 | | | |
| aag | aag | gtg | ttc | aag | gaa | gct | gtg | cag | ggc | atg | gtg | gcc | aag | ggc | acc | 1284 |
| Lys | Lys | Val | Phe | Lys | Glu | Ala | Val | Gln | Gly | Met | Val | Ala | Lys | Gly | Thr | |
| | | 355 | | | | | 360 | | | | | 365 | | | | |
| aca | ggc | tac | aag | gcc | ggc | ttt | gag | tat | gcc | ttt | gac | cag | ctg | cag | aac | 1332 |
| Thr | Gly | Tyr | Lys | Ala | Gly | Phe | Glu | Tyr | Ala | Phe | Asp | Gln | Leu | Gln | Asn | |
| | 370 | | | | | 375 | | | | | 380 | | | | | |
| tcc | aac | atc | act | cgg | gcc | aac | tgc | aac | aag | atg | atc | atg | atg | ttc | acg | 1380 |

```
Ser Asn Ile Thr Arg Ala Asn Cys Asn Lys Met Ile Met Met Phe Thr
385                 390                 395                 400 gat ggt ggt gag gac cgc gtg cag gac gtc ttt gag aag tac aat tgg        1428
Asp Gly Gly Glu Asp Arg Val Gln Asp Val Phe Glu Lys Tyr Asn Trp
                    405                 410                 415 cca aac cgg acg gtg cgc gtg ttt act ttc tcc gtg ggg cag cat aac        1476
Pro Asn Arg Thr Val Arg Val Phe Thr Phe Ser Val Gly Gln His Asn
                420                 425                 430 tat gac gtc aca ccg ctg cag tgg atg gcc tgt gcc aac aaa ggc tac        1524
Tyr Asp Val Thr Pro Leu Gln Trp Met Ala Cys Ala Asn Lys Gly Tyr
            435                 440                 445 tat ttt gag atc cct tcc atc gga gcc atc cgc atc aac aca cag gaa        1572
Tyr Phe Glu Ile Pro Ser Ile Gly Ala Ile Arg Ile Asn Thr Gln Glu
        450                 455                 460 tat cta gat gtg ttg ggc agg ccc atg gtg ctg gca ggc aag gag gcc        1620
Tyr Leu Asp Val Leu Gly Arg Pro Met Val Leu Ala Gly Lys Glu Ala
465                 470                 475                 480 aag cag gtt cag tgg acc aac gtg tat gag gat gca ctg gga ctg ggg        1668
Lys Gln Val Gln Trp Thr Asn Val Tyr Glu Asp Ala Leu Gly Leu Gly
                    485                 490                 495 ttg gtg gta aca ggg acc ctc cct gtt ttc aac ctg aca cag gat ggc        1716
Leu Val Val Thr Gly Thr Leu Pro Val Phe Asn Leu Thr Gln Asp Gly
                500                 505                 510 cct ggg gaa aag aag aac cag ctg atc ctg ggc gtg atg ggc att gac        1764
Pro Gly Glu Lys Lys Asn Gln Leu Ile Leu Gly Val Met Gly Ile Asp
            515                 520                 525 gtg gct ctg aat gac atc aag agg ctg acc ccc aac tac acg ctt gga        1812
Val Ala Leu Asn Asp Ile Lys Arg Leu Thr Pro Asn Tyr Thr Leu Gly
        530                 535                 540 gcc aac ggc tat gtg ttt gcc att gac ctg aac ggc tac gtg ttg ctg        1860
Ala Asn Gly Tyr Val Phe Ala Ile Asp Leu Asn Gly Tyr Val Leu Leu
545                 550                 555                 560 cac ccc aat ctc aag ccc cag acc acc aac ttc cgg gag cct gtg act        1908
His Pro Asn Leu Lys Pro Gln Thr Thr Asn Phe Arg Glu Pro Val Thr
                    565                 570                 575 ctg gac ttc ctg gat gcg gag cta gag gat gag aac aag gaa gag atc        1956
Leu Asp Phe Leu Asp Ala Glu Leu Glu Asp Glu Asn Lys Glu Glu Ile
                580                 585                 590 cgt cgg agc atg att gat ggc aac aag ggc cac aag cag atc aga acg        2004
Arg Arg Ser Met Ile Asp Gly Asn Lys Gly His Lys Gln Ile Arg Thr
            595                 600                 605 ttg gtc aag tcc ctg gat gag agg tac ata gat gag gtg aca cgg aac        2052
Leu Val Lys Ser Leu Asp Glu Arg Tyr Ile Asp Glu Val Thr Arg Asn
        610                 615                 620 tac acc tgg gtg cct ata agg agc act aac tac agc ctg ggg ctg gtg        2100
Tyr Thr Trp Val Pro Ile Arg Ser Thr Asn Tyr Ser Leu Gly Leu Val
625                 630                 635                 640 ctc cca ccc tac agc acc ttc tac ctc caa gcc aat ctc agt gac cag        2148
Leu Pro Pro Tyr Ser Thr Phe Tyr Leu Gln Ala Asn Leu Ser Asp Gln
                    645                 650                 655 atc ctg cag gtc aag tat ttt gag ttc ctg ctc ccc agc agc ttt gag        2196
Ile Leu Gln Val Lys Tyr Phe Glu Phe Leu Leu Pro Ser Ser Phe Glu
                660                 665                 670 tct gaa gga cac gtt ttc att gct ccc aga gag tac tgc aag gac ctg        2244
Ser Glu Gly His Val Phe Ile Ala Pro Arg Glu Tyr Cys Lys Asp Leu
            675                 680                 685 aat gcc tca gac aac aac acc gag ttc ctg aaa aac ttt att gag ctc        2292
Asn Ala Ser Asp Asn Asn Thr Glu Phe Leu Lys Asn Phe Ile Glu Leu
        690                 695                 700
```

```
atg gag aaa gtg act cca gac tcc aag cag tgc aac aac ttc ctt ctg      2340
Met Glu Lys Val Thr Pro Asp Ser Lys Gln Cys Asn Asn Phe Leu Leu
705             710                 715                 720 cac aac ctg atc ttg gac acg ggc atc acg cag cag ctg gta gag cgt      2388
His Asn Leu Ile Leu Asp Thr Gly Ile Thr Gln Gln Leu Val Glu Arg
            725                 730                 735 gtg tgg agg gac cag gat ctc aac acg tac agc cta ctg gcc gtg ttc      2436
Val Trp Arg Asp Gln Asp Leu Asn Thr Tyr Ser Leu Leu Ala Val Phe
        740                 745                 750 gct gcc aca gac ggt ggc atc acc cga gtc ttc ccc aac aag gca gct      2484
Ala Ala Thr Asp Gly Gly Ile Thr Arg Val Phe Pro Asn Lys Ala Ala
    755                 760                 765 gag gac tgg aca gag aac cct gag ccc ttc aat gcc agc ttc tac cgc      2532
Glu Asp Trp Thr Glu Asn Pro Glu Pro Phe Asn Ala Ser Phe Tyr Arg
770                 775                 780 cgc agc ctg gat aac cac ggt tat gtc ttc aag ccc cca cac cag gat      2580
Arg Ser Leu Asp Asn His Gly Tyr Val Phe Lys Pro Pro His Gln Asp
785             790                 795                 800 gcc ctg tta agg ccg ctg gag ctg gag aat gac act gtg ggc atc ctc      2628
Ala Leu Leu Arg Pro Leu Glu Leu Glu Asn Asp Thr Val Gly Ile Leu
            805                 810                 815 gtc agc aca gct gtg gag ctc agc cta ggc agg cgc aca ctg agg cca      2676
Val Ser Thr Ala Val Glu Leu Ser Leu Gly Arg Arg Thr Leu Arg Pro
        820                 825                 830 gca gtg gtg ggc gtc aag ctg gac cta gag gct tgg gct gag aag ttc      2724
Ala Val Val Gly Val Lys Leu Asp Leu Glu Ala Trp Ala Glu Lys Phe
    835                 840                 845 aag gtg cta gcc agc aac cgt acc cac caa gac cag cct cag aag tgc      2772
Lys Val Leu Ala Ser Asn Arg Thr His Gln Asp Gln Pro Gln Lys Cys
850                 855                 860 ggc ccc aac agc cac tgt gag atg gac tgc gag gtt aac aat gag gac      2820
Gly Pro Asn Ser His Cys Glu Met Asp Cys Glu Val Asn Asn Glu Asp
865             870                 875                 880 tta ctc tgt gtc ctc att gat gat gga gga ttc ctg gtg ctg tca aac      2868
Leu Leu Cys Val Leu Ile Asp Asp Gly Gly Phe Leu Val Leu Ser Asn
            885                 890                 895 cag aac cat cag tgg gac cag gtg ggc agg ttc ttc agt gag gtg gat      2916
Gln Asn His Gln Trp Asp Gln Val Gly Arg Phe Phe Ser Glu Val Asp
        900                 905                 910 gcc aac ctg atg ctg gca ctc tac aat aac tcc ttc tac acc cgc aag      2964
Ala Asn Leu Met Leu Ala Leu Tyr Asn Asn Ser Phe Tyr Thr Arg Lys
    915                 920                 925 gag tcc tat gac tat cag gca gcc tgt gcc cct cag ccc cct ggc aac      3012
Glu Ser Tyr Asp Tyr Gln Ala Ala Cys Ala Pro Gln Pro Pro Gly Asn
930                 935                 940 ctg ggt gct gca ccc cgg ggt gtc ttt gtg ccc acc gtt gca gat ttc      3060
Leu Gly Ala Ala Pro Arg Gly Val Phe Val Pro Thr Val Ala Asp Phe
945             950                 955                 960 ctt aac ctg gcc tgg tgg acc tct gct gcc gcc tgg tcc ctg ttc cag      3108
Leu Asn Leu Ala Trp Trp Thr Ser Ala Ala Ala Trp Ser Leu Phe Gln
            965                 970                 975 cag ctt ctc tac ggc ctc atc tac cac agc tgg ttc caa gca gac ccc      3156
Gln Leu Leu Tyr Gly Leu Ile Tyr His Ser Trp Phe Gln Ala Asp Pro
        980                 985                 990 gcg gag gcc gag ggg agc ccc gag acg cgc gag agc agc tgc gtc atg      3204
Ala Glu Ala Glu Gly Ser Pro Glu Thr Arg Glu Ser Ser Cys Val Met
    995                 1000                1005 aaa cag acc cag tac tac ttc ggc tcg gta aac gcc tcc tac aac gcc      3252
Lys Gln Thr Gln Tyr Tyr Phe Gly Ser Val Asn Ala Ser Tyr Asn Ala
    1010                1015                1020
```

|  |  |
|---|---|
| atc atc gac tgc gga aac tgc tcc agg ctg ttc cac gcg cag aga ctg<br>Ile Ile Asp Cys Gly Asn Cys Ser Arg Leu Phe His Ala Gln Arg Leu<br>1025               1030               1035              1040 | 3300 |
| acc aac acc aat ctt ctc ttt gtg gtg gcc gag aag ccg ctg tgc agc<br>Thr Asn Thr Asn Leu Leu Phe Val Val Ala Glu Lys Pro Leu Cys Ser<br>               1045               1050              1055 | 3348 |
| cag tgc gag gct ggc cgg ctg ctg cag aag gag acg cac tgc cca gcg<br>Gln Cys Glu Ala Gly Arg Leu Leu Gln Lys Glu Thr His Cys Pro Ala<br>           1060               1065              1070 | 3396 |
| gac ggc ccg gag cag tgt gag cta gtg cag aga ccg cga tac cgg aga<br>Asp Gly Pro Glu Gln Cys Glu Leu Val Gln Arg Pro Arg Tyr Arg Arg<br>      1075               1080              1085 | 3444 |
| ggc ccg cac atc tgc ttc gac tac aac gcg aca gaa gat acc tca gac<br>Gly Pro His Ile Cys Phe Asp Tyr Asn Ala Thr Glu Asp Thr Ser Asp<br>   1090               1095              1100 | 3492 |
| tgt ggc cgc ggg gcc tcc ttc ccg ccg tcg ctg ggc gtc ctg gtc tcc<br>Cys Gly Arg Gly Ala Ser Phe Pro Pro Ser Leu Gly Val Leu Val Ser<br>1105               1110               1115              1120 | 3540 |
| ctg caa ctg ctg ctc ctc ctg ggc ctg ccg ccc cgg ccg cag cct caa<br>Leu Gln Leu Leu Leu Leu Leu Gly Leu Pro Pro Arg Pro Gln Pro Gln<br>               1125               1130              1135 | 3588 |
| gtc ctc gtc cac gcc tct cgc cgc ctc tga gcaccctgcc ccaccccacc<br>Val Leu Val His Ala Ser Arg Arg Leu<br>               1140               1145 | 3638 |
| tccactccca cctcacccgg cctcttcgcc tttcccaccc tcctgcccca cactcccgc | 3698 |
| cttagagcct cgtccctccc tcactgaagg acctgagctg gccaggccct gagagtctgg | 3758 |
| tctgcgcctt gggatgggga gtcccaaagc gggacgccgc aggtgtttgg cacccaaatc | 3818 |
| acatctcacc tccgaactgt tcaagtgtcc ccagacccct cttgcctgct gggctccccc | 3878 |
| cagtgggatg ggacagggag gccacacgca ctggtgccaa accaggcct ctgctgccgc | 3938 |
| ccttcctgga ggctgcctat gttggggggg accctgcctc agctgacccg gcctctctgc | 3998 |
| cccacccaag cccaaacttg gtttctgtga aatagtgga ggaaggtgag atggccagtt | 4058 |
| tgaagcctgt gcctcccagc ttaaatccta gcaggagaga ggctctgggg cagccccat | 4118 |
| gggctcctgc cccttcagg cctacagcca tccccaag cccaccaggt gtcaggatag | 4178 |
| tcacagtgat accagttcag acactacccc atatacacct ggaacattga ggatggaaac | 4238 |
| tggactcaca ttcgacatac cccactgggc acacgcacaa acacacacac tatgggtgg | 4298 |
| ggtgggtgta gggcttaca aagccttaca caggggcgagg ggttggtggg agggttggca | 4358 |
| cctgcacact ccatctcctg ctcaccacct gcctctaatc tgagctgcag cctggctggt | 4418 |
| cctcccattt ctaaagctga atgtcaaaca gtgccaaatg ctggggcagg gggtgaagaa | 4478 |
| ccctctgtcc caccctagc caccagtgtc ctccaagtgc cccctcacct tccaggtgc | 4538 |
| tcattgtaac catttctcac tagtgtcagg ccccagtgg gaccacatgc cactgcctgc | 4598 |
| acctttcggc agaggaaccc ccaccagaca tcacccttg ccttagcagg ggtgactttg | 4658 |
| tctctcctgg ctgggccatc cttccgccaa tctggcccatt acacactcag gcctgtgccc | 4718 |
| actccctatc tccttcccac ccctacacac acactccctg cttgcaggag gccaaactgt | 4778 |
| ccctccttg ctgaacacac acacacacac acacacacag gtggggactg gcacagctc | 4838 |
| ttcacaccat tcattctggt catttccccc aaaggcatcc cagcctgggg gccagtgggg | 4898 |
| aactgagggc aagggggatat agtgatgggg ctcagatgga ctgggaggag ggggaggggtg | 4958 |
| atgcattaat taatggcttc gttaattaat gtcatgttgc ttgtcgcttt ctcagtgtgt | 5018 |

-continued

```
gtgtgtggtc catgcccact gctggtgcca gggtgggtgt ccatgtgcac ccggcctgga    5078
tgccagctgt gtccttcggg ggcgtgcgtg taactgtagt gtagtcaggt gctcaatgga    5138
gaatataaac atatacagaa aaatatatat tttaagttta aaaaacagaa aaacagacaa    5198
aacaatcccc atcaggtagc tgtctaaccc ccagctgggt ctaatccttc tcattaccca    5258
cccgacctgg ctgcccctca ccttgggctg ggggactggg gggccatttc cttttctctg    5318 ccctttttt gttgttctat tttgtacaga caagttggaa aaacaacagc gacaaaaaag    5378
tcaagaaact ttgtaaaata tcgtgtgtgt gattccttgt aaaatatttt caaatggttt    5438
attacagaag atcagttatt aaataatgtt catattttca cttc                    5482
```

<210> SEQ ID NO 4
<211> LENGTH: 1145
<212> TYPE: PRT
<213> ORGANISM: Homo sapiens

<400> SEQUENCE: 4

```
Met Ala Val Pro Ala Arg Thr Cys Gly Ala Ser Arg Pro Gly Pro Ala
 1               5                  10                  15

Arg Thr Ala Arg Pro Trp Pro Gly Cys Gly Pro His Pro Gly Pro Gly
             20                  25                  30

Thr Arg Arg Pro Thr Ser Gly Pro Pro Arg Pro Leu Trp Leu Leu Leu
         35                  40                  45

Pro Leu Leu Pro Leu Leu Ala Ala Pro Gly Ala Ser Ala Tyr Ser Phe
     50                  55                  60

Pro Gln Gln His Thr Met Gln His Trp Ala Arg Arg Leu Glu Gln Glu
 65                  70                  75                  80

Val Asp Gly Val Met Arg Ile Phe Gly Gly Val Gln Gln Leu Arg Glu
                 85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
```

-continued

```
                290                 295                 300
Leu Thr Leu Lys Leu Met Lys Thr Ser Val Cys Glu Met Leu Asp Thr
305                 310                 315                 320

Leu Ser Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
                340                 345                 350

Lys Lys Val Phe Lys Glu Ala Val Gln Gly Met Val Ala Lys Gly Thr
                355                 360                 365

Thr Gly Tyr Lys Ala Gly Phe Glu Tyr Ala Phe Asp Gln Leu Gln Asn
370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
                420                 425                 430

Tyr Asp Val Thr Pro Leu Gln Trp Met Ala Cys Ala Asn Lys Gly Tyr
                435                 440                 445

Tyr Phe Glu Ile Pro Ser Ile Gly Ala Ile Arg Ile Asn Thr Gln Glu
                450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
                500                 505                 510

Pro Gly Glu Lys Lys Asn Gln Leu Ile Leu Gly Val Met Gly Ile Asp
                515                 520                 525

Val Ala Leu Asn Asp Ile Lys Arg Leu Thr Pro Asn Tyr Thr Leu Gly
                530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
                580                 585                 590

Arg Arg Ser Met Ile Asp Gly Asn Lys Gly His Lys Gln Ile Arg Thr
                595                 600                 605

Leu Val Lys Ser Leu Asp Glu Arg Tyr Ile Asp Glu Val Thr Arg Asn
                610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
                660                 665                 670

Ser Glu Gly His Val Phe Ile Ala Pro Arg Glu Tyr Cys Lys Asp Leu
                675                 680                 685

Asn Ala Ser Asp Asn Asn Thr Glu Phe Leu Lys Asn Phe Ile Glu Leu
                690                 695                 700

Met Glu Lys Val Thr Pro Asp Ser Lys Gln Cys Asn Asn Phe Leu Leu
705                 710                 715                 720
```

-continued

```
His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
            740                 745                 750

Ala Ala Thr Asp Gly Gly Ile Thr Arg Val Phe Pro Asn Lys Ala Ala
            755                 760                 765

Glu Asp Trp Thr Glu Asn Pro Glu Pro Phe Asn Ala Ser Phe Tyr Arg
            770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
                820                 825                 830

Ala Val Val Gly Val Lys Leu Asp Leu Glu Ala Trp Ala Glu Lys Phe
                835                 840                 845

Lys Val Leu Ala Ser Asn Arg Thr His Gln Asp Gln Pro Gln Lys Cys
                850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
                900                 905                 910

Ala Asn Leu Met Leu Ala Leu Tyr Asn Asn Ser Phe Tyr Thr Arg Lys
                915                 920                 925

Glu Ser Tyr Asp Tyr Gln Ala Ala Cys Ala Pro Gln Pro Pro Gly Asn
                930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Trp Ser Leu Phe Gln
                965                 970                 975

Gln Leu Leu Tyr Gly Leu Ile Tyr His Ser Trp Phe Gln Ala Asp Pro
                980                 985                 990

Ala Glu Ala Glu Gly Ser Pro Glu Thr Arg Gly Ser Ser Cys Val Met
                995                 1000                1005

Lys Gln Thr Gln Tyr Tyr Phe Gly Ser Val Asn Ala Ser Tyr Asn Ala
    1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
                1045                1050                1055

Gln Cys Glu Ala Gly Arg Leu Leu Gln Lys Glu Thr His Cys Pro Ala
            1060                1065                1070

Asp Gly Pro Glu Gln Cys Glu Leu Val Gln Arg Pro Arg Tyr Arg Arg
            1075                1080                1085

Gly Pro His Ile Cys Phe Asp Tyr Asn Ala Thr Glu Asp Thr Ser Asp
    1090                1095                1100

Cys Gly Arg Gly Ala Ser Phe Pro Pro Ser Leu Gly Val Leu Val Ser
1105                1110                1115                1120

Leu Gln Leu Leu Leu Leu Gly Leu Pro Pro Arg Pro Gln Pro Gln
                1125                1130                1135
```

```
Val Leu Val His Ala Ser Arg Arg Leu
        1140                1145

<210> SEQ ID NO 5
<211> LENGTH: 5279
<212> TYPE: DNA
<213> ORGANISM: Homo sapiens
<220> FEATURE:
<221> NAME/KEY: CDS
<222> LOCATION: (185)..(3415)

<400> SEQUENCE: 5
atccgcggcg aagcgagtgg ctgcagaggg ctgcatcctg ccgtcccag ccccccacaa      60 ccgtacagcc gtgcccaggt ttccgcttag ggaaccagga ggtccaggcc ctttctgcca    120
gcagccgggc gtgcaagccc ccgacagaga gaaatcttaa agatagctag agccacgggg    180 gctg atg cag cac tgg gcc cgg cgt ctg gag cag gag gtc gac ggc gtg    229
     Met Gln His Trp Ala Arg Arg Leu Glu Gln Glu Val Asp Gly Val
     1               5                  10                  15 atg cgg att ttt gga ggc gtc cag cag ctc cgt gag att tac aag gac    277
Met Arg Ile Phe Gly Gly Val Gln Gln Leu Arg Glu Ile Tyr Lys Asp
            20                  25                  30 aac cgg aac ctg ttc gag gta cag gag aat gag cct cag aag ttg gtg    325
Asn Arg Asn Leu Phe Glu Val Gln Glu Asn Glu Pro Gln Lys Leu Val
        35                  40                  45 gag aag gtg gca ggg gac att gag agc ctt ctg gac agg aag gtg cag    373
Glu Lys Val Ala Gly Asp Ile Glu Ser Leu Leu Asp Arg Lys Val Gln
    50                  55                  60 gcc ctg aag aga ctg gct gat gct gca gag aac ttc cag aaa gca cac    421
Ala Leu Lys Arg Leu Ala Asp Ala Ala Glu Asn Phe Gln Lys Ala His
65                  70                  75 cgc tgg cag gac aac atc aag gag gaa gac atc gtg tac tat gac gcc    469
Arg Trp Gln Asp Asn Ile Lys Glu Glu Asp Ile Val Tyr Tyr Asp Ala
 80                  85                  90                  95 aag gct gac gct gag ctg gac gac cct gag agt gag gat gtg gaa agg    517
Lys Ala Asp Ala Glu Leu Asp Asp Pro Glu Ser Glu Asp Val Glu Arg
                100                 105                 110 ggg tct aag gcc agc acc cta agg ctg gac ttc atc gag gac cca aac    565
Gly Ser Lys Ala Ser Thr Leu Arg Leu Asp Phe Ile Glu Asp Pro Asn
            115                 120                 125 ttc aag aac aag gtc aac tat tca tac gcg gct gta cag atc cct acg    613
Phe Lys Asn Lys Val Asn Tyr Ser Tyr Ala Ala Val Gln Ile Pro Thr
        130                 135                 140 gac atc tac aaa ggc tcc act gtc atc ctc aat gag ctc aac tgg aca    661
Asp Ile Tyr Lys Gly Ser Thr Val Ile Leu Asn Glu Leu Asn Trp Thr
145                 150                 155 gag gcc ctg gag aat gtg ttc atg gaa aac cgc aga caa gac ccc aca    709
Glu Ala Leu Glu Asn Val Phe Met Glu Asn Arg Arg Gln Asp Pro Thr
160                 165                 170                 175 ctg ctg tgg cag gtc ttc ggc agc gcc aca gga gtc act cgc tac tac    757
Leu Leu Trp Gln Val Phe Gly Ser Ala Thr Gly Val Thr Arg Tyr Tyr
                180                 185                 190 ccg gcc acc ccg tgg cga gcc ccc aag aag atc gac ctg tac gat gtc    805
Pro Ala Thr Pro Trp Arg Ala Pro Lys Lys Ile Asp Leu Tyr Asp Val
            195                 200                 205 cga agg aga ccc tgg tat atc cag ggg gcc tcg tca ccc aaa gac atg    853
Arg Arg Arg Pro Trp Tyr Ile Gln Gly Ala Ser Ser Pro Lys Asp Met
        210                 215                 220 gtc atc atc gtg gat gtg agt ggc agt gtg agc ggc ctg acc ctg aag    901
Val Ile Ile Val Asp Val Ser Gly Ser Val Ser Gly Leu Thr Leu Lys
225                 230                 235
```

-continued

```
ctg atg aag aca tct gtc tgc gag atg ctg gac acg ctg tct gat gat       949
Leu Met Lys Thr Ser Val Cys Glu Met Leu Asp Thr Leu Ser Asp Asp
240             245                 250                 255 gac tat gtg aat gtg gcc tcg ttc aac gag aag gca cag cct gtg tca       997
Asp Tyr Val Asn Val Ala Ser Phe Asn Glu Lys Ala Gln Pro Val Ser
            260                 265                 270 tgc ttc aca cac ctg gtg cag gcc aat gtg cgc aac aag aag gtg ttc      1045
Cys Phe Thr His Leu Val Gln Ala Asn Val Arg Asn Lys Lys Val Phe
        275                 280                 285 aag gaa gct gtg cag ggc atg gtg gcc aag ggc acc aca ggc tac aag      1093
Lys Glu Ala Val Gln Gly Met Val Ala Lys Gly Thr Thr Gly Tyr Lys
    290                 295                 300 gcc ggc ttt gag tat gcc ttt gac cag ctg cag aac tcc aac atc act      1141
Ala Gly Phe Glu Tyr Ala Phe Asp Gln Leu Gln Asn Ser Asn Ile Thr
305                 310                 315 cgg gcc aac tgc aac aag atg atc atg atg ttc acg gat ggt ggt gag      1189
Arg Ala Asn Cys Asn Lys Met Ile Met Met Phe Thr Asp Gly Gly Glu
320             325                 330                 335 gac cgc gtg cag gac gtc ttt gag aag tac aat tgg cca aac cgg acg      1237
Asp Arg Val Gln Asp Val Phe Glu Lys Tyr Asn Trp Pro Asn Arg Thr
            340                 345                 350 gtg cgc gtg ttt act ttc tcc gtg ggg cag cat aac tat gac gtc aca      1285
Val Arg Val Phe Thr Phe Ser Val Gly Gln His Asn Tyr Asp Val Thr
        355                 360                 365 ccg ctg cag tgg atg gcc tgt gcc aac aaa ggc tac tat ttt gag atc      1333
Pro Leu Gln Trp Met Ala Cys Ala Asn Lys Gly Tyr Tyr Phe Glu Ile
    370                 375                 380 cct tcc atc gga gcc atc cgc atc aac aca cag gaa tat cta gat gtg      1381
Pro Ser Ile Gly Ala Ile Arg Ile Asn Thr Gln Glu Tyr Leu Asp Val
385                 390                 395 ttg ggc agg ccc atg gtg ctg gca ggc aag gag gcc aag cag gtt cag      1429
Leu Gly Arg Pro Met Val Leu Ala Gly Lys Glu Ala Lys Gln Val Gln
400             405                 410                 415 tgg acc aac gtg tat gag gat gca ctg gga ctg ggg ttg gtg gta aca      1477
Trp Thr Asn Val Tyr Glu Asp Ala Leu Gly Leu Gly Leu Val Val Thr
            420                 425                 430 ggg acc ctc cct gtt ttc aac ctg aca cag gat ggc cct ggg gaa aag      1525
Gly Thr Leu Pro Val Phe Asn Leu Thr Gln Asp Gly Pro Gly Glu Lys
        435                 440                 445 aag aac cag ctg atc ctg ggc gtg atg ggc att gac gtg gct ctg aat      1573
Lys Asn Gln Leu Ile Leu Gly Val Met Gly Ile Asp Val Ala Leu Asn
    450                 455                 460 gac atc aag agg ctg acc ccc aac tac acg ctt gga gcc aac ggc tat      1621
Asp Ile Lys Arg Leu Thr Pro Asn Tyr Thr Leu Gly Ala Asn Gly Tyr
465                 470                 475 gtg ttt gcc att gac ctg aac ggc tac gtg ttg ctg cac ccc aat ctc      1669
Val Phe Ala Ile Asp Leu Asn Gly Tyr Val Leu Leu His Pro Asn Leu
480             485                 490                 495 aag ccc cag acc acc aac ttc cgg gag cct gtg act ctg gac ttc ctg      1717
Lys Pro Gln Thr Thr Asn Phe Arg Glu Pro Val Thr Leu Asp Phe Leu
            500                 505                 510 gat gcg gag cta gag gat gag aac aag gaa gag atc cgt cgg agc atg      1765
Asp Ala Glu Leu Glu Asp Glu Asn Lys Glu Glu Ile Arg Arg Ser Met
        515                 520                 525 att gat ggc aac aag ggc cac aag cag atc aga acg ttg gtc aag tcc      1813
Ile Asp Gly Asn Lys Gly His Lys Gln Ile Arg Thr Leu Val Lys Ser
    530                 535                 540 ctg gat gag agg tac ata gat gag gtg aca cgg aac tac acc tgg gtg      1861
Leu Asp Glu Arg Tyr Ile Asp Glu Val Thr Arg Asn Tyr Thr Trp Val
```

-continued

```
           545                 550                 555
cct ata agg agc act aac tac agc ctg ggg ctg gtg ctc cca ccc tac      1909
Pro Ile Arg Ser Thr Asn Tyr Ser Leu Gly Leu Val Leu Pro Pro Tyr
560                 565                 570                 575 agc acc ttc tac ctc caa gcc aat ctc agt gac cag atc ctg cag gtc      1957
Ser Thr Phe Tyr Leu Gln Ala Asn Leu Ser Asp Gln Ile Leu Gln Val
                580                 585                 590 aag tat ttt gag ttc ctg ctc ccc agc agc ttt gag tct gaa gga cac      2005
Lys Tyr Phe Glu Phe Leu Leu Pro Ser Ser Phe Glu Ser Glu Gly His
            595                 600                 605 gtt ttc att gct ccc aga gag tac tgc aag gac ctg aat gcc tca gac      2053
Val Phe Ile Ala Pro Arg Glu Tyr Cys Lys Asp Leu Asn Ala Ser Asp
        610                 615                 620 aac aac acc gag ttc ctg aaa aac ttt att gag ctc atg gag aaa gtg      2101
Asn Asn Thr Glu Phe Leu Lys Asn Phe Ile Glu Leu Met Glu Lys Val
    625                 630                 635 act cca gac tcc aag cag tgc aac aac ttc ctt ctg cac aac ctg atc      2149
Thr Pro Asp Ser Lys Gln Cys Asn Asn Phe Leu Leu His Asn Leu Ile
640                 645                 650                 655 ttg gac acg ggc atc acg cag cag ctg gta gag cgt gtg tgg agg gac      2197
Leu Asp Thr Gly Ile Thr Gln Gln Leu Val Glu Arg Val Trp Arg Asp
                660                 665                 670 cag gat ctc aac acg tac agc cta ctg gcc gtg ttc gct gcc aca gac      2245
Gln Asp Leu Asn Thr Tyr Ser Leu Leu Ala Val Phe Ala Ala Thr Asp
            675                 680                 685 ggt ggc atc acc cga gtc ttc ccc aac aag gca gct gag gac tgg aca      2293
Gly Gly Ile Thr Arg Val Phe Pro Asn Lys Ala Ala Glu Asp Trp Thr
        690                 695                 700 gag aac cct gag ccc ttc aat gcc agc ttc tac cgc cgc agc ctg gat      2341
Glu Asn Pro Glu Pro Phe Asn Ala Ser Phe Tyr Arg Arg Ser Leu Asp
    705                 710                 715 aac cac ggt tat gtc ttc aag ccc cca cac cag gat gcc ctg tta agg      2389
Asn His Gly Tyr Val Phe Lys Pro Pro His Gln Asp Ala Leu Leu Arg
720                 725                 730                 735 ccg ctg gag ctg gag aat gac act gtg ggc atc ctc gtc agc aca gct      2437
Pro Leu Glu Leu Glu Asn Asp Thr Val Gly Ile Leu Val Ser Thr Ala
                740                 745                 750 gtg gag ctc agc cta ggc agg cgc aca ctg agg cca gca gtg gtg ggc      2485
Val Glu Leu Ser Leu Gly Arg Arg Thr Leu Arg Pro Ala Val Val Gly
            755                 760                 765 gtc aag ctg gac cta gag gct tgg gct gag aag ttc aag gtg cta gcc      2533
Val Lys Leu Asp Leu Glu Ala Trp Ala Glu Lys Phe Lys Val Leu Ala
        770                 775                 780 agc aac cgt acc cac caa gac cag cct cag aag tgc ggc ccc aac agc      2581
Ser Asn Arg Thr His Gln Asp Gln Pro Gln Lys Cys Gly Pro Asn Ser
    785                 790                 795 cac tgt gag atg gac tgc gag gtt aac aat gag gac tta ctc tgt gtc      2629
His Cys Glu Met Asp Cys Glu Val Asn Asn Glu Asp Leu Leu Cys Val
800                 805                 810                 815 ctc att gat gat gga gga ttc ctg gtg ctg tca aac cag aac cat cag      2677
Leu Ile Asp Asp Gly Gly Phe Leu Val Leu Ser Asn Gln Asn His Gln
                820                 825                 830 tgg gac cag gtg ggc agg ttc ttc agt gag gtg gat gcc aac ctg atg      2725
Trp Asp Gln Val Gly Arg Phe Phe Ser Glu Val Asp Ala Asn Leu Met
            835                 840                 845 ctg gca ctc tac aat aac tcc ttc tac acc cgc aag gag tcc tat gac      2773
Leu Ala Leu Tyr Asn Asn Ser Phe Tyr Thr Arg Lys Glu Ser Tyr Asp
        850                 855                 860 tat cag gca gcc tgt gcc cct cag ccc cct ggc aac ctg ggt gct gca      2821
Tyr Gln Ala Ala Cys Ala Pro Gln Pro Pro Gly Asn Leu Gly Ala Ala
```

-continued

| | | |
|---|---|---|
| Tyr Gln Ala Ala Cys Ala Pro Gln Pro Pro Gly Asn Leu Gly Ala Ala<br>865                     870                     875 | | |
| ccc cgg ggt gtc ttt gtg ccc acc gtt gca gat ttc ctt aac ctg gcc<br>Pro Arg Gly Val Phe Val Pro Thr Val Ala Asp Phe Leu Asn Leu Ala<br>880                     885                     890                     895 | 2869 | |
| tgg tgg acc tct gct gcc gcc tgg tcc ctg ttc cag cag ctt ctc tac<br>Trp Trp Thr Ser Ala Ala Ala Trp Ser Leu Phe Gln Gln Leu Leu Tyr<br>                     900                     905                     910 | 2917 | |
| ggc ctc atc tac cac agc tgg ttc caa gca gac ccc gcg gag gcc gag<br>Gly Leu Ile Tyr His Ser Trp Phe Gln Ala Asp Pro Ala Glu Ala Glu<br>               915                     920                     925 | 2965 | |
| ggg agc ccc gag acg cgc gag agc agc tgc gtc atg aaa cag acc cag<br>Gly Ser Pro Glu Thr Arg Glu Ser Ser Cys Val Met Lys Gln Thr Gln<br>        930                     935                     940 | 3013 | |
| tac tac ttc ggc tcg gta aac gcc tcc tac aac gcc atc atc gac tgc<br>Tyr Tyr Phe Gly Ser Val Asn Ala Ser Tyr Asn Ala Ile Ile Asp Cys<br>945                     950                     955 | 3061 | |
| gga aac tgc tcc agg ctg ttc cac gcg cag aga ctg acc aac acc aat<br>Gly Asn Cys Ser Arg Leu Phe His Ala Gln Arg Leu Thr Asn Thr Asn<br>960                     965                     970                     975 | 3109 | |
| ctt ctc ttt gtg gtg gcc gag aag ccg ctg tgc agc cag tgc gag gct<br>Leu Leu Phe Val Val Ala Glu Lys Pro Leu Cys Ser Gln Cys Glu Ala<br>                     980                     985                     990 | 3157 | |
| ggc cgg ctg ctg cag aag gag acg cac tgc cca gcg gac ggc ccg gag<br>Gly Arg Leu Leu Gln Lys Glu Thr His Cys Pro Ala Asp Gly Pro Glu<br>        995                     1000                    1005 | 3205 | |
| cag tgt gag cta gtg cag aga ccg cga tac cgg aga ggc ccg cac atc<br>Gln Cys Glu Leu Val Gln Arg Pro Arg Tyr Arg Arg Gly Pro His Ile<br>1010                     1015                    1020 | 3253 | |
| tgc ttc gac tac aac gcg aca gaa gat acc tca gac tgt ggc cgc ggg<br>Cys Phe Asp Tyr Asn Ala Thr Glu Asp Thr Ser Asp Cys Gly Arg Gly<br>     1025                    1030                    1035 | 3301 | |
| gcc tcc ttc ccg ccg tcg ctg ggc gtc ctg gtc tcc ctg caa ctg ctg<br>Ala Ser Phe Pro Pro Ser Leu Gly Val Leu Val Ser Leu Gln Leu Leu<br>1040                     1045                    1050                    1055 | 3349 | |
| ctc ctc ctg ggc ctg ccg ccc cgg ccg cag cct caa gtc ctc gtc cac<br>Leu Leu Leu Gly Leu Pro Pro Arg Pro Gln Pro Gln Val Leu Val His<br>                    1060                    1065                    1070 | 3397 | |
| gcc tct cgc cgc ctc tga gcaccctgcc ccaccccacc tccactccca<br>Ala Ser Arg Arg Leu<br>             1075 | 3445 | |
| cctcacccgg cctcttcgcc tttcccaccc tcctgcccca cactcccgc cttagagcct | 3505 | |
| cgtccctccc tcactgaagg acctgagctg gccaggccct gagagtctgg tctgcgcctt | 3565 | |
| gggatgggga gtcccaaagc gggacgccgc aggtgtttgg cacccaaatc acatctcacc | 3625 | |
| tccgaactgt tcaagtgtcc ccagaccctt cttgcctgct gggctccccc cagtgggatg | 3685 | |
| ggacagggag gccacacgca ctggtgccaa accaggcct ctgctgccgc ccttcctgga | 3745 | |
| ggctgcctat gttgggggg accctgcctc agctgacccg gcctctctgc cccacccaag | 3805 | |
| cccaaacttg gtttctgtga gaatagtgga ggaaggtgag atggccagtt tgaagcctgt | 3865 | |
| gcctcccagc ttaaatccta gcaggagaga ggctctgggg cagcccccat gggctcctgc | 3925 | |
| cccttt cagg cctacagcca catccccaag cccaccaggt gtcaggatag tcacagtgat | 3985 | |
| accagttcag acactacccc atatacacct ggaacattga ggatggaaac tggactcaca | 4045 | |
| ttcgacatac cccactgggc acacgcacaa acacacacac tatggggtgg ggtgggtgta | 4105 | |
| ggggcttaca aagccttaca cagggcgagg ggttggtggg agggttggca cctgcacact | 4165 |

```
ccatctcctg ctcaccacct gcctctaatc tgagctgcag cctggctggt cctcccattt    4225
ctaaagctga atgtcaaaca gtgccaaatg ctggggcagg gggtgaagaa ccctctgtcc    4285
caccactagc caccagtgtc ctccaagtgc cccctcacct ctccaggtgc tcattgtaac    4345
catttctcac tagtgtcagg cccccagtgg gaccacatgc cactgcctgc acctttcggc    4405
agaggaaccc ccaccagaca tcacccttg ccttagcagg ggtgactttg tctctcctgg    4465
ctgggccatc cttccgccaa tctggcccctt acacactcag gcctgtgccc actccctatc    4525
tccttcccac ccctacacac acactccctg cttgcaggag gccaaactgt ccctcccttg    4585
ctgaacacac acacacacac acacacacag gtggggactg ggcacagctc ttcacaccat    4645
tcattctggt catttccccc aaaggcatcc cagcctgggg gccagtgggg aactgagggc    4705 aagggatat agtgatgggg ctcagatgga ctgggaggag gggagggtg atgcattaat    4765 taatggcttc gttaattaat gtcatgttgc ttgtcgcttt ctcagtgtgt gtgtgtggtc    4825 catgccact gctggtgcca gggtgggtgt ccatgtgcac ccggcctgga tgccagctgt    4885
gtccttcggg ggcgtgcgtg taactgtagt gtagtcaggt gctcaatgga gaatataaac    4945
atatacagaa aaatatatat tttaagttta aaaaacagaa aaacagacaa aacaatcccc    5005
atcaggtagc tgtctaaccc ccagctgggt ctaatccttc tcattaccca cccgacctgg    5065
ctgcccctca ccttgggctg ggggactggg gggccatttc cttttctctg cccttttttt    5125
gttgttctat tttgtacaga caagttggaa aaacaacagc gacaaaaaag tcaagaaact    5185
ttgtaaaata tcgtgtgtgt gattccttgt aaaatatttt caaatggttt attacagaag    5245
atcagttatt aaataatgtt catattttca cttc                                5279

<210> SEQ ID NO 6
<211> LENGTH: 1076
<212> TYPE: PRT
<213> ORGANISM: Homo sapiens

<400> SEQUENCE: 6

Met Gln His Trp Ala Arg Arg Leu Glu Gln Glu Val Asp Gly Val Met
 1               5                  10                  15

Arg Ile Phe Gly Gly Val Gln Gln Leu Arg Glu Ile Tyr Lys Asp Asn
                20                  25                  30

Arg Asn Leu Phe Glu Val Gln Glu Asn Glu Pro Gln Lys Leu Val Glu
            35                  40                  45

Lys Val Ala Gly Asp Ile Glu Ser Leu Leu Asp Arg Lys Val Gln Ala
        50                  55                  60

Leu Lys Arg Leu Ala Asp Ala Glu Asn Phe Gln Lys Ala His Arg
    65                  70                  75                  80

Trp Gln Asp Asn Ile Lys Glu Glu Asp Ile Val Tyr Tyr Asp Ala Lys
                85                  90                  95

Ala Asp Ala Glu Leu Asp Asp Pro Glu Ser Glu Asp Val Glu Arg Gly
            100                 105                 110

Ser Lys Ala Ser Thr Leu Arg Leu Asp Phe Ile Glu Asp Pro Asn Phe
        115                 120                 125

Lys Asn Lys Val Asn Tyr Ser Tyr Ala Ala Val Gln Ile Pro Thr Asp
    130                 135                 140

Ile Tyr Lys Gly Ser Thr Val Ile Leu Asn Glu Leu Asn Trp Thr Glu
145                 150                 155                 160

Ala Leu Glu Asn Val Phe Met Glu Asn Arg Arg Gln Asp Pro Thr Leu
                165                 170                 175
```

-continued

```
Leu Trp Gln Val Phe Gly Ser Ala Thr Gly Val Thr Arg Tyr Tyr Pro
                180                 185                 190

Ala Thr Pro Trp Arg Ala Pro Lys Lys Ile Asp Leu Tyr Asp Val Arg
            195                 200                 205

Arg Arg Pro Trp Tyr Ile Gln Gly Ala Ser Ser Pro Lys Asp Met Val
        210                 215                 220

Ile Ile Val Asp Val Ser Gly Ser Val Ser Gly Leu Thr Leu Lys Leu
225                 230                 235                 240

Met Lys Thr Ser Val Cys Glu Met Leu Asp Thr Leu Ser Asp Asp Asp
                245                 250                 255

Tyr Val Asn Val Ala Ser Phe Asn Glu Lys Ala Gln Pro Val Ser Cys
            260                 265                 270

Phe Thr His Leu Val Gln Ala Asn Val Arg Asn Lys Lys Val Phe Lys
        275                 280                 285

Glu Ala Val Gln Gly Met Val Ala Lys Gly Thr Thr Gly Tyr Lys Ala
290                 295                 300

Gly Phe Glu Tyr Ala Phe Asp Gln Leu Gln Asn Ser Asn Ile Thr Arg
305                 310                 315                 320

Ala Asn Cys Asn Lys Met Ile Met Met Phe Thr Asp Gly Gly Glu Asp
                325                 330                 335

Arg Val Gln Asp Val Phe Glu Lys Tyr Asn Trp Pro Asn Arg Thr Val
            340                 345                 350

Arg Val Phe Thr Phe Ser Val Gly Gln His Asn Tyr Asp Val Thr Pro
        355                 360                 365

Leu Gln Trp Met Ala Cys Ala Asn Lys Gly Tyr Tyr Phe Glu Ile Pro
        370                 375                 380

Ser Ile Gly Ala Ile Arg Ile Asn Thr Gln Glu Tyr Leu Asp Val Leu
385                 390                 395                 400

Gly Arg Pro Met Val Leu Ala Gly Lys Glu Ala Lys Gln Val Gln Trp
                405                 410                 415

Thr Asn Val Tyr Glu Asp Ala Leu Gly Leu Gly Leu Val Val Thr Gly
            420                 425                 430

Thr Leu Pro Val Phe Asn Leu Thr Gln Asp Gly Pro Gly Glu Lys Lys
        435                 440                 445

Asn Gln Leu Ile Leu Gly Val Met Gly Ile Asp Val Ala Leu Asn Asp
450                 455                 460

Ile Lys Arg Leu Thr Pro Asn Tyr Thr Leu Gly Ala Asn Gly Tyr Val
465                 470                 475                 480

Phe Ala Ile Asp Leu Asn Gly Tyr Val Leu Leu His Pro Asn Leu Lys
                485                 490                 495

Pro Gln Thr Thr Asn Phe Arg Glu Pro Val Thr Leu Asp Phe Leu Asp
            500                 505                 510

Ala Glu Leu Glu Asp Glu Asn Lys Glu Glu Ile Arg Arg Ser Met Ile
        515                 520                 525

Asp Gly Asn Lys Gly His Lys Gln Ile Arg Thr Leu Val Lys Ser Leu
        530                 535                 540

Asp Glu Arg Tyr Ile Asp Glu Val Thr Arg Asn Tyr Thr Trp Val Pro
545                 550                 555                 560

Ile Arg Ser Thr Asn Tyr Ser Leu Gly Leu Val Leu Pro Pro Tyr Ser
                565                 570                 575

Thr Phe Tyr Leu Gln Ala Asn Leu Ser Asp Gln Ile Leu Gln Val Lys
            580                 585                 590

Tyr Phe Glu Phe Leu Leu Pro Ser Ser Phe Glu Ser Glu Gly His Val
```

-continued

```
              595                 600                 605
Phe Ile Ala Pro Arg Glu Tyr Cys Lys Asp Leu Asn Ala Ser Asp Asn
    610                 615                 620

Asn Thr Glu Phe Leu Lys Asn Phe Ile Glu Leu Met Glu Lys Val Thr
625                 630                 635                 640

Pro Asp Ser Lys Gln Cys Asn Asn Phe Leu Leu His Asn Leu Ile Leu
                645                 650                 655

Asp Thr Gly Ile Thr Gln Gln Leu Val Glu Arg Val Trp Arg Asp Gln
            660                 665                 670

Asp Leu Asn Thr Tyr Ser Leu Leu Ala Val Phe Ala Ala Thr Asp Gly
        675                 680                 685

Gly Ile Thr Arg Val Phe Pro Asn Lys Ala Ala Glu Asp Trp Thr Glu
    690                 695                 700

Asn Pro Glu Pro Phe Asn Ala Ser Phe Tyr Arg Arg Ser Leu Asp Asn
705                 710                 715                 720

His Gly Tyr Val Phe Lys Pro Pro His Gln Asp Ala Leu Leu Arg Pro
                725                 730                 735

Leu Glu Leu Glu Asn Asp Thr Val Gly Ile Leu Val Ser Thr Ala Val
            740                 745                 750

Glu Leu Ser Leu Gly Arg Arg Thr Leu Arg Pro Ala Val Val Gly Val
        755                 760                 765

Lys Leu Asp Leu Glu Ala Trp Ala Glu Lys Phe Lys Val Leu Ala Ser
770                 775                 780

Asn Arg Thr His Gln Asp Gln Pro Gln Lys Cys Gly Pro Asn Ser His
785                 790                 795                 800

Cys Glu Met Asp Cys Glu Val Asn Asn Glu Asp Leu Leu Cys Val Leu
                805                 810                 815

Ile Asp Asp Gly Gly Phe Leu Val Leu Ser Asn Gln Asn His Gln Trp
            820                 825                 830

Asp Gln Val Gly Arg Phe Phe Ser Glu Val Asp Ala Asn Leu Met Leu
        835                 840                 845

Ala Leu Tyr Asn Asn Ser Phe Tyr Thr Arg Lys Glu Ser Tyr Asp Tyr
850                 855                 860

Gln Ala Ala Cys Ala Pro Gln Pro Gly Asn Leu Gly Ala Ala Pro
865                 870                 875                 880

Arg Gly Val Phe Val Pro Thr Val Ala Asp Phe Leu Asn Leu Ala Trp
                885                 890                 895

Trp Thr Ser Ala Ala Ala Trp Ser Leu Phe Gln Gln Leu Leu Tyr Gly
            900                 905                 910

Leu Ile Tyr His Ser Trp Phe Gln Ala Asp Pro Ala Glu Ala Glu Gly
        915                 920                 925

Ser Pro Glu Thr Arg Glu Ser Ser Cys Val Met Lys Gln Thr Gln Tyr
930                 935                 940

Tyr Phe Gly Ser Val Asn Ala Ser Tyr Asn Ala Ile Ile Asp Cys Gly
945                 950                 955                 960

Asn Cys Ser Arg Leu Phe His Ala Gln Arg Leu Thr Asn Thr Asn Leu
                965                 970                 975

Leu Phe Val Val Ala Glu Lys Pro Leu Cys Ser Gln Cys Glu Ala Gly
            980                 985                 990

Arg Leu Leu Gln Lys Glu Thr His Cys Pro Ala Asp Gly Pro Glu Gln
        995                 1000                1005

Cys Glu Leu Val Gln Arg Pro Arg Tyr Arg Arg Gly Pro His Ile Cys
    1010                1015                1020
```

```
Phe Asp Tyr Asn Ala Thr Glu Asp Thr Ser Asp Cys Gly Arg Gly Ala
1025                1030                1035                1040

Ser Phe Pro Pro Ser Leu Gly Val Leu Val Ser Leu Gln Leu Leu Leu
            1045                1050                1055

Leu Leu Gly Leu Pro Pro Arg Pro Gln Pro Gln Val Leu Val His Ala
        1060                1065                1070

Ser Arg Arg Leu
        1075
```

<210> SEQ ID NO 7
<211> LENGTH: 1070
<212> TYPE: DNA
<213> ORGANISM: Homo sapiens

<400> SEQUENCE: 7

```
cttaaagata gctagagcca cgggggctgt aagttcagca tgcctccttt tctggtctcc      60
gctgaagctg tcactccacc attaaacctg tgactctagg ccttaagcct gttgaaggtc     120
gagcccccaa aagggtcaca tatgctcctg ccttgggccg cggggcccgg gactcttccc     180
gcgggtgggg tggggaggag cggcaggggtc tgaggtgtgg gggcgggggc gcacccgggg     240
cgctcgggta gcagctgggg cgcaggacgc ccgagccagt agggcaggat tcgggctgcg     300
cggggacgag aggcgcgcgg gcacggggtgg gcgcgtggcc gcggcggggg cgcgcggggg     360
cgggccagcc cgggaagaga gagggaggga gggagagaag agggcggtgc cggcaggttg     420
gcggcggctg ctatttgagc gcaggtcccg ggccgggcgc tcagagcgct tggagccagc     480
gctgcaggga gatagcagcg cgcagcccgc agaggcgctg cggcccgtgc agccccggag     540
gccctcgcg gagaaggcgg cggcggagga gaggccgagt taccgcccgc cgcccgcgcc      600
ccccaaccc cgccgccgcc gccgccgccg ccactgcccc ccctcccgc ggcgccgcat      660
cttgaatgga aacatggcgg tgccggctcg gacctgcggc gcctctcggc ccggcccagc     720
gcggactgcg cgcccctggc ccggctgcgg ccccaccct ggccccggca ccggcgccc      780
gacgtccggg cccccgcgcc cgctgtggct gctgctgccg cttctaccgc tgctcgccgc     840
ccccggcgcc tctgcctaca gcttccccca gcagcacacg taagtggcct cggccggccg     900
cgagaccccg gccgagcctt gcgccccgct ctgcccccgg tccgcgctac tccttccctg     960
cgctccgcgc cagggcagag gcgctgggtc cggctgcccg ctgcgcccgg gggcgacggc    1020
cccaagcccc gaaggctggc agccgcggtc ccggcgctct ggctgcgtca                1070
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 8

```
ctctacaacc caattcacca t                                                21
```

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 9

-continued

```
tagatggcac tggccttct                                              19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 10
actcaccacc ctactgttc                                              19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 11
agctgcctgt ttggtgcta                                              19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 12
ctgagagtga ggatgtggaa                                             20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
gtgcatcctc atacacgttg                                             20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 14
gacaagccac cccttaccta c                                           21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 15
gcagagccca gttctggctg                                             20

<210> SEQ ID NO 16
<211> LENGTH: 20
<212> TYPE: DNA
<213> ORGANISM: Artificial Sequence
```

```
<220> FEATURE:
<223> OTHER INFORMATION: Description of Artificial Sequence: Synthetic

<400> SEQUENCE: 16
ccagcataga gtggtcagtg                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 17
agtaccctgt ccattgcctg                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 18
ggcaggtagc actgatggtc                                                     20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 19
ttggagccac tgagtggaag                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 20
gtggcttacg gtcctcactc                                                     20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 21
tgtgctggga gtcgcggctg                                                     20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 22
accactggac tgcctgcggt g                                                   21
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 23
cagggctggc agtgctacac                                            20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 24
actgccagcc ctgtgaccat g                                          21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 25
ccatctccag tccaggcatc                                            20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 26
ttcgacagga cacagcccag                                            20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 27
tgctgggtag acagggaca g                                           21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 28
agcccagtcg cctctgcaag                                            20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 29
tggatacagc tggctgcgcc                                                  20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 30
ccttacccta acagaggcat c                                                21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 31
aacctcacgt gttctcctgc                                                  20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 32
tgggcaggag aacacgtgag                                                  20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 33
ctggtgatgg tcacaggagc                                                  20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 34
aggccactca ccaccctact g                                                21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 35
tcctgggtac accaagccag                                                  20

<210> SEQ ID NO 36

```
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 36
ggagggctga gagctgcctg                                                    20

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 37
ttgaggttac tgctgtggcc ac                                                 22

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 38
ctggtggcca cagcagtcac                                                    20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 39
ggatggccag ttgaacatac g                                                  21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 40
ttcgacagga cacagcccag                                                    20

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 41
gtgctgggta gacaggggac agg                                                23

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 42
```

-continued

```
tgggcaggag aacacgtgag                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 43
ctggtgatgg tcacaggagc                                              20

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 44
acccctggct tctgcttcct t                                            21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 45
acactgccct catggtacag                                              20

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 46
acctccctgt gctctgtccc tca                                          23

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 47
aatccacgca tggatgggca                                              20

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 48
tgagcagcta gtgctgaggc ctct                                         24

<210> SEQ ID NO 49
<211> LENGTH: 23
<212> TYPE: DNA
```

```
<213> ORGANISM: Artificial Sequence
<220> FEATURE:
<223> OTHER INFORMATION: Description of Artificial Sequence: Synthetic

<400> SEQUENCE: 49
cagcaaggag gtgtggctca gga                                        23

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 50
actccaagca gtgtgagtgc                                            20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 51
gaaggaagtt gttgcctgga a                                          21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 52
caggtgtgga aataagcagg                                            20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 53
catcttcttg cagctccttg                                            20

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 54
tgcccttgtt acagtcatct cca                                        23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 55
taagatgaaa agccagccag ctg                                        23
```

```
<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 56
gtctcctctt tggacagatt ctg                                           23

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 57
tggagatgac tgtaacaagg gcac                                          24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 58
aagaggagac ttcccagtct cttg                                          24

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 59
ctgcatacag gatgcagcac tg                                            22

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 60
gctcacctca cggagctgct gcga                                          24

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 61
tgttcagccc agggaagcga agc                                           23

<210> SEQ ID NO 62
<211> LENGTH: 23
<212> TYPE: DNA
<213> ORGANISM: Artificial Sequence
<220> FEATURE:
```

<223> OTHER INFORMATION: Description of Artificial Sequence: Synthetic

<400> SEQUENCE: 62
acttacagcc cccgtggctc tag                                   23

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 63
cctggctctg gaagaatcta                                       20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 64
cagaaaagga ggcatgctga                                       20

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 65
aagcgagtgg ctgcagag                                         18

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 66
ctaagcggaa acctgggca                                        19

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 67
gcatcttgaa tggaaacatg gc                                    22

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 68
tcgacctcct gctccaga                                         18

```
<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 69
agcacacgat gcagcactg                                              19

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 70
cttctccacc aacttctgag                                             20

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 71
acaaccggaa cctgttcga                                              19

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 72
cgtcatagta cacgatgtct tc                                          22

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 73
atgctgcaga gaacttccag                                             20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 74
tgaagtttgg gtcctcgatg                                             20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 75
ctgagagtga ggatgtggaa                                               20

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 76
aagacctgcc acagcagtg                                                19

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 77
gtgttcatgg aaaaccgcag                                               20

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 78
ccactcacat ccacgatgat g                                             21

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 79
ctgtacgatg tccgaaggag ac                                            22

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 80
tgtgaagcat gacacaggct g                                             21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 81
atctgtctgc gagatgctgg                                               20

<210> SEQ ID NO 82
<211> LENGTH: 19
```

```
<212> TYPE: DNA
<213> ORGANISM: Artificial Sequence
<220> FEATURE:
<223> OTHER INFORMATION: Description of Artificial Sequence: Synthetic

<400> SEQUENCE: 82
ttctgcagct ggtcaaagg                                                       19

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 83
cgcaacaaga aggtgttcaa g                                                    21

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 84
gccccacgga gaaagtaaac                                                      20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 85
tgttcacgga tggtggtgag                                                      20

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 86
ttcctgtgtg ttgatgcgg                                                       19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 87
ttgagatccc ttccatcgg                                                       19

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 88
```
gctggttctt cttttcccca g                               21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 89
gtggtaacag ggaccctccc t                               21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 90
agattggggt gcagcaacac                                 20

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 91
gctatgtgtt tgccattgac c                               21

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 92
ctatgtacct ctcatccagg gac                             23

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 93
catgattgat ggcaacaagg                                 20

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 94
ggggagcagg aactcaaaat ac                              22

<210> SEQ ID NO 95
<211> LENGTH: 22
<212> TYPE: DNA
<213> ORGANISM: Artificial Sequence

```
<220> FEATURE:
<223> OTHER INFORMATION: Description of Artificial Sequence: Synthetic

<400> SEQUENCE: 95
gccaatctca gtgaccagat cc                                              22

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 96
aggttgtgca gaaggaagtt g                                               21

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 97
agaaagtgac tccagactcc aag                                             23

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 98
ttgaagggct cagggttctc                                                 20

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 99
ggatctcaac acgtacagcc tac                                             23

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 100
ggatgcccac agtgtcattc                                                 20

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 101
cccttcaatg ccagcttcta c                                               21
```

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 102
aacttctcag cccaagcctc                                          20

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 103
aatgacactg tgggcatcct c                                        21

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 104
ttaacctcgc agtccatctc ac                                       22

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 105
accaagacca gcctcagaag tg                                       22

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 106
ataggactcc ttgcgggtgt ag                                       22

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 107
aggtggatgc caacctgatg                                          20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 108
cgtagagaag ctgctggaac ag                                            22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 109
caccgttgca gatttcctta ac                                            22

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 110
agtttccgca gtcgatgatg                                               20

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 111
gaaacagacc cagtactact tc                                            22

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 112
gcgttgtagt cgaagcagat                                               20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 113
agcagtgtga gctagtgcag                                               20

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 114
agggtgggaa aggcgaaga                                                19